United States Patent
Subramanian et al.

(10) Patent No.: US 9,181,572 B2
(45) Date of Patent: *Nov. 10, 2015

(54) METHODS TO MODULATE LYSINE VARIANT DISTRIBUTION

(71) Applicant: ABBVIE INC., North Chicago, IL (US)

(72) Inventors: Kartik Subramanian, Northborough, MA (US); Mayda Perez, Worcester, MA (US); Xiaobei Zeng, Carolina, PR (US); Chee Furng Wong, Singapore (SG); Christopher Chumsae, North Andover, MA (US)

(73) Assignee: AbbVie, Inc., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/830,976

(22) Filed: Mar. 14, 2013

(65) Prior Publication Data

US 2013/0280274 A1    Oct. 24, 2013

Related U.S. Application Data

(60) Provisional application No. 61/636,469, filed on Apr. 20, 2012, provisional application No. 61/696,207, filed on Sep. 2, 2012.

(51) Int. Cl.

| C12P 21/08 | (2006.01) |
|---|---|
| C12P 21/00 | (2006.01) |
| C07K 16/00 | (2006.01) |
| C07K 16/28 | (2006.01) |
| C12N 5/00 | (2006.01) |

(52) U.S. Cl.
CPC ............... *C12P 21/00* (2013.01); *C07K 16/00* (2013.01); *C07K 16/2803* (2013.01); *C12N 5/0018* (2013.01); *C07K 2317/14* (2013.01); *C07K 2317/40* (2013.01); *C07K 2317/526* (2013.01); *C12N 2500/22* (2013.01); *C12N 2500/32* (2013.01); *C12N 2511/00* (2013.01)

(58) Field of Classification Search
None
See application file for complete search history.

(56) References Cited

U.S. PATENT DOCUMENTS

| RE30,985 E | 6/1982 | Cartaya |
|---|---|---|
| 4,399,216 A | 8/1983 | Axel et al. |
| 4,510,245 A | 4/1985 | Cousens et al. |
| 4,560,655 A | 12/1985 | Baker |
| 4,634,665 A | 1/1987 | Axel et al. |
| 4,657,866 A | 4/1987 | Kumar |
| 4,767,704 A | 8/1988 | Cleveland et al. |
| 4,801,687 A | 1/1989 | Ngo |
| 4,816,397 A | 3/1989 | Boss et al. |
| 4,877,608 A | 10/1989 | Lee et al. |
| 4,927,762 A | 5/1990 | Darfler |
| 4,933,435 A | 6/1990 | Ngo |
| 4,968,615 A | 11/1990 | Koszinowski et al. |
| 5,045,468 A | 9/1991 | Darfler |
| 5,096,816 A | 3/1992 | Maiorella |
| 5,110,913 A | 5/1992 | Coan et al. |
| 5,118,796 A | 6/1992 | Prior et al. |
| 5,122,469 A | 6/1992 | Mather et al. |
| 5,126,250 A | 6/1992 | McDonough et al. |
| 5,168,062 A | 12/1992 | Stinski |
| 5,179,017 A | 1/1993 | Axel et al. |
| 5,231,024 A | 7/1993 | Moeller et al. |
| 5,328,985 A | 7/1994 | Sano et al. |
| 5,378,612 A | 1/1995 | Nakashima et al. |
| 5,429,746 A | 7/1995 | Shadle et al. |
| 5,530,101 A | 6/1996 | Queen et al. |
| 5,545,403 A | 8/1996 | Page |
| 5,545,806 A | 8/1996 | Lonberg et al. |
| 5,545,807 A | 8/1996 | Surani et al. |
| 5,561,053 A | 10/1996 | Crowley |
| 5,569,825 A | 10/1996 | Lonberg et al. |
| 5,625,126 A | 4/1997 | Lonberg et al. |
| 5,633,162 A | 5/1997 | Keen et al. |
| 5,633,425 A | 5/1997 | Lonberg et al. |
| 5,644,036 A | 7/1997 | Ramage et al. |
| 5,654,407 A | 8/1997 | Boyle et al. |
| 5,656,272 A | 8/1997 | Le et al. |
| 5,661,016 A | 8/1997 | Lonberg et al. |
| 5,672,347 A | 9/1997 | Aggarwal et al. |
| 5,672,502 A | 9/1997 | Birch et al. |
| 5,698,195 A | 12/1997 | Le et al. |
| 5,705,364 A | 1/1998 | Etcheverry et al. |
| 5,721,121 A | 2/1998 | Etcheverry et al. |
| 5,770,429 A | 6/1998 | Lonberg et al. |
| 5,789,650 A | 8/1998 | Lonberg et al. |

(Continued)

FOREIGN PATENT DOCUMENTS

| CN | 1299370 A | 6/2001 |
|---|---|---|
| CN | 1563090 A | 1/2005 |

(Continued)

OTHER PUBLICATIONS

Feng et al., mAbs 2:5, 466-477; Sep./Oct. 2010.*
Barnes et al., Biotechnology and Bioengineering, vol. 81, No. 6, Mar. 20, 2003, pp. 631-639.*
Wolff et al., J. Biol. Chem. 1962, 237:3094-3099.*
ICH Topic Q6B "Specifications: Test Procedures and Acceptance Criteria for Biotechnological/Biological Products," Sep. 1999, pp. 1-17.*

(Continued)

*Primary Examiner* — Zachary Skelding
(74) *Attorney, Agent, or Firm* — McCarter & English, LLP; Maria Laccotripe Zacharakis; Deborah L. Nagle

(57) ABSTRACT

The instant invention relates to the field of protein production and purification, and in particular to compositions and processes for controlling the distribution or amount of lysine variants expressed by host cells, as well as to compositions and processes for controlling the amount of lysine variants present in purified preparations.

30 Claims, 28 Drawing Sheets

(56) References Cited

U.S. PATENT DOCUMENTS

| | | |
|---|---|---|
| 5,795,967 A | 8/1998 | Aggarwal et al. |
| 5,811,299 A | 9/1998 | Renner et al. |
| 5,859,205 A | 1/1999 | Adair et al. |
| 5,876,961 A | 3/1999 | Crowe et al. |
| 5,877,293 A | 3/1999 | Adair et al. |
| 5,929,212 A | 7/1999 | Jolliffe et al. |
| 5,945,098 A | 8/1999 | Sarno et al. |
| 5,976,833 A | 11/1999 | Furukawa et al. |
| 5,994,510 A | 11/1999 | Adair et al. |
| 6,024,938 A | 2/2000 | Corbo et al. |
| 6,036,978 A | 3/2000 | Gombotz et al. |
| 6,048,728 A | 4/2000 | Inlow et al. |
| 6,066,719 A | 5/2000 | Zapata |
| 6,075,181 A | 6/2000 | Kucherlapati et al. |
| 6,090,382 A | 7/2000 | Salfeld et al. |
| 6,113,898 A | 9/2000 | Anderson et al. |
| 6,150,584 A | 11/2000 | Kucherlapati et al. |
| 6,171,586 B1 | 1/2001 | Lam et al. |
| 6,255,458 B1 | 7/2001 | Lonberg et al. |
| 6,258,562 B1 | 7/2001 | Salfeld et al. |
| 6,270,766 B1 | 8/2001 | Feldman et al. |
| 6,300,129 B1 | 10/2001 | Lonberg et al. |
| 6,339,142 B1 | 1/2002 | Basey et al. |
| 6,399,381 B1 | 6/2002 | Blum et al. |
| 6,406,909 B1 | 6/2002 | Shibuya et al. |
| 6,410,270 B1 | 6/2002 | Strittmatter et al. |
| 6,413,746 B1 | 7/2002 | Field |
| 6,436,397 B1 | 8/2002 | Baker et al. |
| 6,448,380 B2 | 9/2002 | Rathjen et al. |
| 6,451,983 B2 | 9/2002 | Rathjen et al. |
| 6,489,447 B1 | 12/2002 | Basey et al. |
| 6,498,237 B2 | 12/2002 | Rathjen et al. |
| 6,509,015 B1 | 1/2003 | Salfeld et al. |
| 6,528,286 B1 | 3/2003 | Ryll |
| 6,593,458 B1 | 7/2003 | Rathjen et al. |
| 6,673,986 B1 | 1/2004 | Kucherlapati et al. |
| 6,680,181 B2 | 1/2004 | Castan |
| 6,870,034 B2 | 3/2005 | Breece et al. |
| 6,872,549 B2 | 3/2005 | Van Ness et al. |
| 6,890,736 B1 | 5/2005 | Reddy et al. |
| 6,900,056 B2 | 5/2005 | Lee et al. |
| 6,914,128 B1 | 7/2005 | Salfeld et al. |
| 6,924,124 B1 | 8/2005 | Singh |
| 6,974,681 B1 | 12/2005 | McGrew |
| 7,070,775 B2 | 7/2006 | Le et al. |
| 7,084,260 B1 | 8/2006 | Lonberg et al. |
| 7,122,641 B2 | 10/2006 | Vedantham et al. |
| 7,189,820 B2 | 3/2007 | Ruben |
| 7,192,584 B2 | 3/2007 | Le et al. |
| 7,223,394 B2 | 5/2007 | Salfeld et al. |
| 7,250,165 B2 | 7/2007 | Heavner et al. |
| 7,276,239 B2 | 10/2007 | Le et al. |
| 7,323,553 B2 | 1/2008 | Fahrner et al. |
| 7,332,303 B2 | 2/2008 | Schilling et al. |
| 7,390,660 B2 | 6/2008 | Behrendt et al. |
| 7,429,491 B2 | 9/2008 | Luan et al. |
| 7,504,485 B2 | 3/2009 | Salfeld et al. |
| 7,521,206 B2 | 4/2009 | Heavner et al. |
| 7,521,210 B2 | 4/2009 | Knudsen |
| 7,541,031 B2 | 6/2009 | Salfeld et al. |
| 7,588,761 B2 | 9/2009 | Salfeld et al. |
| 7,645,609 B2 | 1/2010 | Follstad |
| 7,714,112 B2 | 5/2010 | Engstrand et al. |
| 7,750,129 B2 | 7/2010 | Johansson et al. |
| 7,767,207 B2 | 8/2010 | Ghayer et al. |
| 7,863,426 B2 | 1/2011 | Wan et al. |
| 7,883,704 B2 | 2/2011 | Salfeld et al. |
| 7,919,264 B2 | 4/2011 | Maksymowych et al. |
| 7,947,471 B2 | 5/2011 | Knudsen |
| 7,972,810 B2 | 7/2011 | Crowell et al. |
| 8,067,182 B2 | 11/2011 | Kelley et al. |
| 8,093,045 B2 | 1/2012 | Pla et al. |
| 8,192,951 B2 | 6/2012 | Wang et al. |
| 8,197,813 B2 | 6/2012 | Salfeld et al. |
| 8,206,714 B2 | 6/2012 | Salfeld et al. |
| 8,209,132 B2 | 6/2012 | Bosques et al. |
| 8,231,876 B2 | 7/2012 | Wan et al. |
| 8,361,797 B2 | 1/2013 | Osborne et al. |
| 8,372,400 B2 | 2/2013 | Salfeld et al. |
| 8,372,401 B2 | 2/2013 | Salfeld et al. |
| 8,414,894 B2 | 4/2013 | Salfeld et al. |
| 8,420,081 B2 | 4/2013 | Fraunhofer et al. |
| 8,436,149 B2 | 5/2013 | Borhani et al. |
| 8,470,552 B2 | 6/2013 | Croughan et al. |
| 8,663,945 B2 | 3/2014 | Pla et al. |
| 8,753,633 B2 | 6/2014 | Salfeld et al. |
| 8,821,865 B2 | 9/2014 | Neu et al. |
| 8,883,146 B2 | 11/2014 | Fraunhofer et al. |
| 8,883,156 B2 | 11/2014 | Wan et al. |
| 8,895,009 B2 | 11/2014 | Wan et al. |
| 8,895,709 B2 | 11/2014 | Hickman et al. |
| 8,906,372 B2 | 12/2014 | Wan et al. |
| 8,906,646 B2 | 12/2014 | Pla et al. |
| 8,911,964 B2 | 12/2014 | Pla et al. |
| 8,916,153 B2 | 12/2014 | Wan et al. |
| 8,921,526 B2 | 12/2014 | Chumsae et al. |
| 8,946,395 B1 | 2/2015 | Herigstad et al. |
| 9,017,687 B1 | 4/2015 | Wang et al. |
| 2002/0045207 A1 | 4/2002 | Krummen et al. |
| 2002/0132299 A1 | 9/2002 | Field |
| 2002/0187526 A1 | 12/2002 | Ruben et al. |
| 2003/0012786 A1 | 1/2003 | Teoh et al. |
| 2003/0049725 A1 | 3/2003 | Heavner et al. |
| 2003/0096414 A1 | 5/2003 | Ciccarone et al. |
| 2003/0125247 A1 | 7/2003 | Rosen et al. |
| 2003/0153735 A1 | 8/2003 | Breece et al. |
| 2003/0157108 A1 | 8/2003 | Presta |
| 2003/0161828 A1 | 8/2003 | Abdelghany et al. |
| 2003/0166869 A1 | 9/2003 | Vedantham et al. |
| 2003/0175884 A1 | 9/2003 | Umana et al. |
| 2003/0178368 A1 | 9/2003 | van Reis |
| 2003/0206898 A1 | 11/2003 | Fischkoff et al. |
| 2003/0219438 A1 | 11/2003 | Salfeld et al. |
| 2003/0229212 A1 | 12/2003 | Fahrner et al. |
| 2003/0235585 A1 | 12/2003 | Fischkoff et al. |
| 2004/0009172 A1 | 1/2004 | Fischkoff et al. |
| 2004/0029229 A1 | 2/2004 | Reeves et al. |
| 2004/0033228 A1 | 2/2004 | Krause et al. |
| 2004/0033535 A1 | 2/2004 | Boyle et al. |
| 2004/0038878 A1 | 2/2004 | Tanikawa et al. |
| 2004/0101939 A1 | 5/2004 | Santora et al. |
| 2004/0120952 A1 | 6/2004 | Knight et al. |
| 2004/0126372 A1 | 7/2004 | Banerjee et al. |
| 2004/0126373 A1 | 7/2004 | Banerjee et al. |
| 2004/0131614 A1 | 7/2004 | Banerjee et al. |
| 2004/0132140 A1 | 7/2004 | Satoh et al. |
| 2004/0136989 A1 | 7/2004 | Banerjee et al. |
| 2004/0136990 A1 | 7/2004 | Banerjee et al. |
| 2004/0136991 A1 | 7/2004 | Banerjee et al. |
| 2004/0151722 A1 | 8/2004 | Banerjee et al. |
| 2004/0162414 A1 | 8/2004 | Santora et al. |
| 2004/0166111 A1 | 8/2004 | Kaymakcalan et al. |
| 2004/0171152 A1 | 9/2004 | Price et al. |
| 2004/0191243 A1 | 9/2004 | Chen et al. |
| 2004/0214289 A1 | 10/2004 | deVries et al. |
| 2004/0219142 A1 | 11/2004 | Banerjee et al. |
| 2005/0004354 A1 | 1/2005 | Salfeld et al. |
| 2005/0100965 A1 | 5/2005 | Ghayur et al. |
| 2005/0123541 A1 | 6/2005 | Heavner et al. |
| 2005/0175611 A1 | 8/2005 | Mahler et al. |
| 2005/0249735 A1 | 11/2005 | Le et al. |
| 2005/0271654 A1 | 12/2005 | Rinderknecht et al. |
| 2005/0272124 A1 | 12/2005 | Chen et al. |
| 2006/0009385 A1 | 1/2006 | Hoffman et al. |
| 2006/0018907 A1 | 1/2006 | Le et al. |
| 2006/0024293 A1 | 2/2006 | Salfeld et al. |
| 2006/0083741 A1 | 4/2006 | Hoffman et al. |
| 2006/0149042 A1 | 7/2006 | Konstantinov et al. |
| 2006/0153846 A1 | 7/2006 | Krause et al. |
| 2006/0246073 A1 | 11/2006 | Knight et al. |
| 2006/0252672 A1 | 11/2006 | Betenbaugh et al. |
| 2006/0269479 A1 | 11/2006 | Colton et al. |
| 2006/0287432 A1 | 12/2006 | Christensen et al. |
| 2007/0003548 A1 | 1/2007 | Heavner et al. |

(56) References Cited

U.S. PATENT DOCUMENTS

| | | |
|---|---|---|
| 2007/0004009 A1 | 1/2007 | Dixit et al. |
| 2007/0041905 A1 | 2/2007 | Hoffman et al. |
| 2007/0060741 A1 | 3/2007 | Kelley et al. |
| 2007/0071747 A1 | 3/2007 | Hoffman et al. |
| 2007/0081996 A1 | 4/2007 | Hoffman et al. |
| 2007/0110743 A1 | 5/2007 | Drapeau et al. |
| 2007/0111284 A1 | 5/2007 | Ryll |
| 2007/0161084 A1 | 7/2007 | Crowell et al. |
| 2007/0172475 A1 | 7/2007 | Matheus et al. |
| 2007/0172897 A1 | 7/2007 | Maksymowych et al. |
| 2007/0184045 A1 | 8/2007 | Doctor et al. |
| 2007/0184529 A1 | 8/2007 | Etcheverry et al. |
| 2007/0190057 A1 | 8/2007 | Wu et al. |
| 2007/0196373 A1 | 8/2007 | Le et al. |
| 2007/0202051 A1 | 8/2007 | Schuschnig |
| 2007/0202104 A1 | 8/2007 | Banerjee et al. |
| 2007/0269463 A1 | 11/2007 | Donovan |
| 2007/0292442 A1 | 12/2007 | Wan et al. |
| 2007/0298040 A1 | 12/2007 | Le et al. |
| 2008/0025976 A1 | 1/2008 | Le et al. |
| 2008/0112953 A1 | 5/2008 | McAuley et al. |
| 2008/0118496 A1 | 5/2008 | Medich et al. |
| 2008/0131374 A1 | 6/2008 | Medich et al. |
| 2008/0160577 A1 | 7/2008 | Dell'Orco et al. |
| 2008/0166348 A1 | 7/2008 | Kupper et al. |
| 2008/0193466 A1 | 8/2008 | Banerjee et al. |
| 2008/0219952 A1 | 9/2008 | Fischer et al. |
| 2008/0227136 A1 | 9/2008 | Pla et al. |
| 2008/0269132 A1 | 10/2008 | Gomes et al. |
| 2008/0269468 A1 | 10/2008 | Vogel et al. |
| 2008/0274507 A1 | 11/2008 | Gomes et al. |
| 2008/0292642 A1 | 11/2008 | Borhani et al. |
| 2008/0305114 A1 | 12/2008 | Salfeld et al. |
| 2008/0311043 A1 | 12/2008 | Hoffman et al. |
| 2009/0017472 A1 | 1/2009 | Stuhlmuller et al. |
| 2009/0028794 A1 | 1/2009 | Medich et al. |
| 2009/0053786 A1 | 2/2009 | Kao et al. |
| 2009/0060910 A1 | 3/2009 | Johnson et al. |
| 2009/0068172 A1 | 3/2009 | Kaymakcalan et al. |
| 2009/0068705 A1 | 3/2009 | Drapeau et al. |
| 2009/0110679 A1 | 4/2009 | Li et al. |
| 2009/0123378 A1 | 5/2009 | Wong et al. |
| 2009/0142828 A1 | 6/2009 | Bucciarelli et al. |
| 2009/0148513 A1 | 6/2009 | Fraunhofer et al. |
| 2009/0155205 A1 | 6/2009 | Salfeld et al. |
| 2009/0175857 A1 | 7/2009 | Salfeld et al. |
| 2009/0202546 A1 | 8/2009 | Harris et al. |
| 2009/0202557 A1 | 8/2009 | Argiriadi et al. |
| 2009/0203055 A1 | 8/2009 | Ngantung et al. |
| 2009/0208500 A1 | 8/2009 | Joly et al. |
| 2009/0226530 A1 | 9/2009 | Lassner et al. |
| 2009/0239259 A1 | 9/2009 | Hsieh |
| 2009/0258018 A1 | 10/2009 | Medich et al. |
| 2009/0269302 A1 | 10/2009 | Salfeld et al. |
| 2009/0271164 A1 | 10/2009 | Peng et al. |
| 2009/0280065 A1 | 11/2009 | Willian et al. |
| 2009/0291062 A1 | 11/2009 | Fraunhofer et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0016557 A1 | 1/2010 | Salfeld et al. |
| 2010/0021451 A1 | 1/2010 | Wong |
| 2010/0034823 A1 | 2/2010 | Borhani et al. |
| 2010/0040604 A1 | 2/2010 | Salfeld et al. |
| 2010/0040630 A1 | 2/2010 | Elden et al. |
| 2010/0135987 A1 | 6/2010 | Hickman et al. |
| 2010/0136025 A1 | 6/2010 | Hickman et al. |
| 2010/0160894 A1 | 6/2010 | Julian et al. |
| 2010/0221823 A1 | 9/2010 | McCoy et al. |
| 2010/0256336 A1 | 10/2010 | Yuk et al. |
| 2010/0278822 A1 | 11/2010 | Fraunhofer et al. |
| 2010/0297697 A1 | 11/2010 | Ambrosius et al. |
| 2011/0002935 A1 | 1/2011 | Wan et al. |
| 2011/0003338 A1 | 1/2011 | Bayer et al. |
| 2011/0053223 A1 | 3/2011 | Bayer et al. |
| 2011/0053265 A1 | 3/2011 | Follstad et al. |
| 2011/0054414 A1 | 3/2011 | Shang et al. |
| 2011/0081679 A1 | 4/2011 | Jing et al. |
| 2011/0081700 A1 | 4/2011 | Hasslacher et al. |
| 2011/0086798 A1 | 4/2011 | Sethuraman et al. |
| 2011/0097336 A1 | 4/2011 | Wu et al. |
| 2011/0123544 A1 | 5/2011 | Salfeld et al. |
| 2011/0130544 A1 | 6/2011 | Ram et al. |
| 2011/0171227 A1 | 7/2011 | Okun et al. |
| 2011/0207676 A1 | 8/2011 | Callewaert et al. |
| 2011/0300151 A1 | 12/2011 | Okun et al. |
| 2012/0014956 A1 | 1/2012 | Kupper et al. |
| 2012/0015438 A1 | 1/2012 | Schilling et al. |
| 2012/0039900 A1 | 2/2012 | Stuhlmuller et al. |
| 2012/0039908 A1 | 2/2012 | Combs et al. |
| 2012/0077213 A1 | 3/2012 | Pla et al. |
| 2012/0107783 A1 | 5/2012 | Julian et al. |
| 2012/0123688 A1 | 5/2012 | Ramasubramanyan et al. |
| 2012/0129185 A1 | 5/2012 | Maksymowych et al. |
| 2012/0171123 A1 | 7/2012 | Medich et al. |
| 2012/0177596 A1 | 7/2012 | Fischkoff et al. |
| 2012/0178107 A1 | 7/2012 | Salfeld et al. |
| 2012/0183997 A1 | 7/2012 | Alley et al. |
| 2012/0190005 A1 | 7/2012 | Schaub et al. |
| 2012/0201831 A1 | 8/2012 | Salfeld et al. |
| 2012/0213792 A1 | 8/2012 | Salfeld et al. |
| 2012/0219564 A1 | 8/2012 | Salfeld et al. |
| 2012/0238730 A1 | 9/2012 | Dong et al. |
| 2012/0244168 A1 | 9/2012 | Salfeld et al. |
| 2012/0251550 A1 | 10/2012 | Borhani et al. |
| 2012/0258114 A1 | 10/2012 | Salfeld et al. |
| 2012/0263731 A1 | 10/2012 | Fraunhofer et al. |
| 2012/0264920 A1 | 10/2012 | Wang et al. |
| 2012/0277165 A1 | 11/2012 | Collins et al. |
| 2012/0282262 A1 | 11/2012 | Okun et al. |
| 2012/0282270 A1 | 11/2012 | Krause et al. |
| 2012/0288494 A1 | 11/2012 | Borhani et al. |
| 2012/0308514 A1 | 12/2012 | Salfeld et al. |
| 2013/0004507 A1 | 1/2013 | Fischkoff et al. |
| 2013/0028903 A1 | 1/2013 | Wan et al. |
| 2013/0065219 A1 | 3/2013 | Tsang et al. |
| 2013/0084605 A1 | 4/2013 | Zhou et al. |
| 2013/0096283 A1 | 4/2013 | Khetan et al. |
| 2013/0115224 A1 | 5/2013 | Salfeld et al. |
| 2013/0122011 A1 | 5/2013 | Hoffman et al. |
| 2013/0122018 A1 | 5/2013 | Salfeld et al. |
| 2013/0156760 A1 | 6/2013 | Fraunhofer et al. |
| 2013/0195888 A1 | 8/2013 | Wang et al. |
| 2013/0205604 A1 | 8/2013 | Esenwein et al. |
| 2013/0243786 A1 | 9/2013 | Banerjee et al. |
| 2013/0273059 A1 | 10/2013 | Wan et al. |
| 2013/0280267 A1 | 10/2013 | Wan et al. |
| 2013/0280274 A1 | 10/2013 | Subramanian et al. |
| 2013/0309242 A1 | 11/2013 | Wan et al. |
| 2013/0323261 A1 | 12/2013 | Wan et al. |
| 2013/0330356 A1 | 12/2013 | Salfeld et al. |
| 2013/0330357 A1 | 12/2013 | Salfeld et al. |
| 2013/0336957 A1 | 12/2013 | Wang et al. |
| 2013/0338344 A1 | 12/2013 | Ramasubramanyan et al. |
| 2013/0344084 A1 | 12/2013 | Subramanian et al. |
| 2014/0010820 A1 | 1/2014 | Wang et al. |
| 2014/0065710 A1 | 3/2014 | Rives et al. |
| 2014/0072585 A1 | 3/2014 | Herigstad et al. |
| 2014/0120583 A1 | 5/2014 | Prentice |
| 2014/0134674 A1 | 5/2014 | Pla et al. |
| 2014/0134675 A1 | 5/2014 | Pla et al. |
| 2014/0141007 A1 | 5/2014 | Fraunhofer et al. |
| 2014/0141008 A1 | 5/2014 | Fraunhofer et al. |
| 2014/0142286 A1 | 5/2014 | Prentice |
| 2014/0154270 A1 | 6/2014 | Wang et al. |
| 2014/0178984 A1 | 6/2014 | Jerums et al. |
| 2014/0206038 A1 | 7/2014 | Pla et al. |
| 2014/0234905 A1 | 8/2014 | Pla et al. |
| 2014/0255423 A1 | 9/2014 | Hickman et al. |
| 2014/0271623 A1 | 9/2014 | Parren et al. |
| 2014/0271626 A1 | 9/2014 | Chumsae et al. |
| 2014/0271632 A1 | 9/2014 | Hossler et al. |
| 2014/0271633 A1 | 9/2014 | Hossler |
| 2014/0275494 A1 | 9/2014 | Wang et al. |

(56) References Cited

U.S. PATENT DOCUMENTS

| | | |
|---|---|---|
| 2014/0288278 A1 | 9/2014 | Nti-gyabaah et al. |
| 2014/0314745 A1 | 10/2014 | Rives et al. |
| 2014/0377275 A1 | 12/2014 | Neu et al. |
| 2015/0023977 A1 | 1/2015 | Fraunhofer et al. |
| 2015/0050693 A1 | 2/2015 | Bengea et al. |
| 2015/0110775 A1 | 4/2015 | Subramanian et al. |
| 2015/0110799 A1 | 4/2015 | Ramasubramanyan et al. |
| 2015/0110803 A1 | 4/2015 | Wang et al. |

FOREIGN PATENT DOCUMENTS

| | | | |
|---|---|---|---|
| DE | 3631229 | A1 | 3/1988 |
| EP | 0101681 | A1 | 3/1984 |
| EP | 0173177 | A1 | 3/1986 |
| EP | 0186833 | A2 | 7/1986 |
| EP | 0212489 | A2 | 3/1987 |
| EP | 0351789 | A2 | 1/1990 |
| EP | 0366043 | A1 | 5/1990 |
| EP | 0460426 | B1 | 12/1991 |
| EP | 0481791 | A2 | 4/1992 |
| EP | 0492448 | A1 | 7/1992 |
| EP | 0523949 | A1 | 1/1993 |
| EP | 0612251 | A1 | 8/1994 |
| EP | 0614984 | A2 | 9/1994 |
| EP | 0659766 | A1 | 6/1995 |
| EP | 0746398 | A1 | 12/1996 |
| EP | 0764719 | A2 | 3/1997 |
| EP | 0956873 | A2 | 11/1999 |
| EP | 0956875 | A2 | 11/1999 |
| EP | 1075488 | A1 | 2/2001 |
| EP | 1174148 | A1 | 1/2002 |
| EP | 1221476 | A2 | 7/2002 |
| EP | 1254666 | A1 | 11/2002 |
| EP | 1308455 | A2 | 5/2003 |
| EP | 1308456 | A2 | 5/2003 |
| EP | 1418967 | A2 | 5/2004 |
| EP | 1568388 | A1 | 8/2005 |
| EP | 1745141 | A1 | 1/2007 |
| EP | 1851305 | A1 | 11/2007 |
| EP | 2080809 | A1 | 7/2009 |
| EP | 2144929 | A1 | 1/2010 |
| EP | 2152856 | A1 | 2/2010 |
| EP | 2213726 | A1 | 8/2010 |
| EP | 2357250 | A2 | 8/2011 |
| EP | 2495307 | A1 | 9/2012 |
| EP | 2528002 | A2 | 11/2012 |
| EP | 2574677 | A1 | 4/2013 |
| GB | 2160530 | A | 12/1985 |
| GB | 2279077 | A | 12/1994 |
| JP | 7289288 | A | 11/1995 |
| WO | WO-87/00195 | A1 | 1/1987 |
| WO | WO-90/03430 | A1 | 4/1990 |
| WO | WO-90/05144 | A1 | 5/1990 |
| WO | WO-91/02078 | A1 | 2/1991 |
| WO | WO-91/09967 | A1 | 7/1991 |
| WO | WO-92/01047 | A1 | 1/1992 |
| WO | WO-92/11383 | A1 | 7/1992 |
| WO | WO-92/16553 | A1 | 10/1992 |
| WO | WO-93/06213 | A1 | 4/1993 |
| WO | WO-94/02602 | A1 | 2/1994 |
| WO | WO-94/08619 | A1 | 4/1994 |
| WO | WO-94/25585 | A1 | 11/1994 |
| WO | WO-94/26910 | A1 | 11/1994 |
| WO | WO-94/29347 | A1 | 12/1994 |
| WO | WO-9511317 | A1 | 4/1995 |
| WO | WO-95/23813 | A1 | 9/1995 |
| WO | WO-96/33208 | A1 | 10/1996 |
| WO | WO-96/33735 | A1 | 10/1996 |
| WO | WO-96/34096 | A1 | 10/1996 |
| WO | WO-9704801 | A1 | 2/1997 |
| WO | WO-97/13852 | A1 | 4/1997 |
| WO | WO-97/29131 | A1 | 8/1997 |
| WO | WO-98/23645 | A1 | 6/1998 |
| WO | WO-98/24883 | A2 | 6/1998 |
| WO | WO-98/24884 | A1 | 6/1998 |
| WO | WO-98/24893 | A2 | 6/1998 |
| WO | WO-9823645 | A1 | 6/1998 |
| WO | WO-98/50433 | A2 | 11/1998 |
| WO | WO-9856418 | A1 | 12/1998 |
| WO | WO-99/32605 | A1 | 7/1999 |
| WO | WO-99/57134 | A1 | 11/1999 |
| WO | WO-9957246 | A1 | 11/1999 |
| WO | WO-0003000 | A2 | 1/2000 |
| WO | WO-01-44442 | A1 | 6/2001 |
| WO | WO-0147554 | A1 | 7/2001 |
| WO | WO-01-59069 | A1 | 8/2001 |
| WO | WO-0177362 | A1 | 10/2001 |
| WO | WO-02/12502 | A2 | 2/2002 |
| WO | WO-0212501 | A2 | 2/2002 |
| WO | WO-03045995 | A2 | 6/2003 |
| WO | WO-03/059935 | A2 | 7/2003 |
| WO | WO-03/066662 | A2 | 8/2003 |
| WO | WO-2004008100 | A2 | 1/2004 |
| WO | WO-2004/058944 | A2 | 7/2004 |
| WO | WO-2004058800 | A2 | 7/2004 |
| WO | WO-2004/097006 | A1 | 11/2004 |
| WO | WO-2005042569 | A1 | 5/2005 |
| WO | WO-2005/082483 | A1 | 9/2005 |
| WO | WO-2006/043895 | A1 | 4/2006 |
| WO | WO-2006045438 | A1 | 5/2006 |
| WO | WO-2006/099308 | A2 | 9/2006 |
| WO | WO-2006/110277 | A1 | 10/2006 |
| WO | WO-2007/087384 | A2 | 8/2007 |
| WO | WO-2007/117490 | A2 | 10/2007 |
| WO | WO-2008/033517 | A2 | 3/2008 |
| WO | WO-2008-057240 | A2 | 5/2008 |
| WO | WO 2008057240 | A2 * | 5/2008 |
| WO | WO-2008068879 | A1 | 6/2008 |
| WO | WO-2008087184 | A2 | 7/2008 |
| WO | WO-2008121616 | A2 | 10/2008 |
| WO | WO-2008135498 | A2 | 11/2008 |
| WO | WO-2009/017491 | A1 | 2/2009 |
| WO | WO-2009023562 | A2 | 2/2009 |
| WO | WO-2009/027041 | A1 | 3/2009 |
| WO | WO-2009058769 | A1 | 5/2009 |
| WO | WO-2009/073569 | A2 | 6/2009 |
| WO | WO-2009135656 | A1 | 11/2009 |
| WO | WO-2010036443 | A1 | 4/2010 |
| WO | WO-2010043703 | A1 | 4/2010 |
| WO | WO-2010122460 | A1 | 10/2010 |
| WO | WO-2010/129469 | A1 | 11/2010 |
| WO | WO-2010127069 | A1 | 11/2010 |
| WO | WO-2011005773 | A2 | 1/2011 |
| WO | WO-2011009623 | A1 | 1/2011 |
| WO | WO-2011-019619 | A1 | 2/2011 |
| WO | WO-2011015926 | A1 | 2/2011 |
| WO | WO-2011024025 | A1 | 3/2011 |
| WO | WO-2011044180 | A1 | 4/2011 |
| WO | WO-2011/073235 | A1 | 6/2011 |
| WO | WO-2011069056 | A2 | 6/2011 |
| WO | WO-2011098526 | A1 | 8/2011 |
| WO | WO-2011110598 | A1 | 9/2011 |
| WO | WO-2011/133886 | A2 | 10/2011 |
| WO | WO-2011127322 | A1 | 10/2011 |
| WO | WO-2011134919 | A2 | 11/2011 |
| WO | WO-2011134920 | A1 | 11/2011 |
| WO | WO-2012019160 | A1 | 2/2012 |
| WO | WO-2012030512 | A1 | 3/2012 |
| WO | WO-2012050175 | A1 | 4/2012 |
| WO | WO-2012051147 | A1 | 4/2012 |
| WO | WO-2012/065072 | A2 | 5/2012 |
| WO | WO-2012062810 | A2 | 5/2012 |
| WO | WO-2012120500 | A2 | 9/2012 |
| WO | WO-2012140138 | A1 | 10/2012 |
| WO | WO-2012145682 | A1 | 10/2012 |
| WO | WO-2012/149197 | A2 | 11/2012 |
| WO | WO-2012147048 | A1 | 11/2012 |
| WO | WO-2012147053 | A1 | 11/2012 |
| WO | WO-2012158551 | A1 | 11/2012 |
| WO | WO-2013/011076 | A2 | 1/2013 |
| WO | WO-2013006461 | A1 | 1/2013 |
| WO | WO-2013006479 | A2 | 1/2013 |
| WO | WO-2013009648 | A2 | 1/2013 |

(56) References Cited

FOREIGN PATENT DOCUMENTS

| WO | WO-2013013013 A2 | 1/2013 |
|---|---|---|
| WO | WO-2013-158273 A1 | 10/2013 |
| WO | WO-2013-158279 A1 | 10/2013 |
| WO | WO-2013158275 A1 | 10/2013 |
| WO | WO-2013-176754 A1 | 11/2013 |
| WO | WO-2013-177115 A2 | 11/2013 |
| WO | WO-2013-177118 A2 | 11/2013 |
| WO | WO-2013-181585 A2 | 12/2013 |

OTHER PUBLICATIONS

Worthington Biochemical Corporation, porcine pancreas carboxypeptidase B, one page, Feb. 25, 2012, downloaded from Waybackmachine Internet Archive.*

Folk et al., J. Biol. Chem. 1960, 235:2272-2277.*

"Genentech unveils production capacity hikes," in-Pharma Technologist.com Jun. 28, 2005, pp. 1-2.

Abraham, E., et al., "Efficacy and Safety of Monoclonal Antibody to Human Tumor Necrosis Factor α in Patients with Sepsis Syndrome," *JAMA*, vol. 273(12):934-941 (1995).

Adams, et al. J. Am. Acad. Dermatol 2004;51 :660-2.

Altamirano, C., et al., "Strategies for fed batch cultivation of t-PA producing CHO cells: substitution of glucose and glutamine and rational design of culture medium", *J. Biotechn.* 110:171-179, 2004.

Antes et al. "Analysis of lysine clipping of a humanized Lewis-Y specific IgG antibody and its relation to Fc-mediated effector function" Journal of Chromatography B:Biomedical Sciences and Applications, Elsevier, Amsterdam, NL, vol. 852, No. 1-2, May 31, 2007, 250-256.

Avgerinos et al. (GAb '04 Abstracts—GE Healthcare Life Sciences, France Oct 3-5, 2004, pp. 15-16 published 2005).

Azevedo et al., "Integrated Process for the Purification of Antibodies Combining Aqueous Two-Phase Extraction, Hydrophobic Interaction Chromatography and Size-Exclusion Chromatography", *Journal of Chromatography* (2008) 1213(2): 154-161.

Ballez, J.S. et al., "Plant protein hydrolysates support CHO-320 cells proliferation and recombinant IFN-[gamma] production in suspension and inside microcarriers in protein-free media", *Cytotechnology* 44:3, 103-114, 2004.

Barbuto, J. et al. "Production of Neutralizing Antibodies to Tumor Necrosis Factor by Human Tumor-Infiltrating B Lymphocytes" *Proc. Am. Assoc. Cancer Res,.* 34:487, Abstr. 2904 (1993).

Biblia, T.A. et al., "In Pursuit of the Optimal Fed-Batch Process for Monoclonal Antibody Production", Biotechnol. Prog 11(1):1-13, Jan.-Feb. 1995.

Birch, Jr. et al., "Antibody production", Adv. Drug Delivery Reviews 58:671-685, 2006.

Blaker, GJ, et al., "The Glucose, Insulin and Glutamine Requirements of Suspension Cultures of HeLa Cells in a Defined Culture Medium", J. Cell Sci. 9:529-537, 1971.

Boekstegers, P., et al., "Repeated administration of a F(ab')2 fragment of an anti-tumor necrosis factor alpha monoclonal antibody in patients with severe sepsis: effects on the cardiovascular system and cytokine levels," *Shock*, vol. 1(4):237-245 (1994).

Bollati-Fogolin M., et al., "Temperature Reduction in Cultures of hGM-CSF-expressing CHO Cells: Effects on Productivity and Product Quantity", Biotechnol. Prog. 21:17-21, 2005.

Bonafede et al. "Cost per treated patient for etanercept, adalimumab, and infliximab across adult indications: a claims analysis" Advances in Therapy, Springer Healthcare Communications, Heidelberg, vol. 29, No. 3, Mar. 9, 2012, 234-249.

Boyle, P. et al. "A Novel Monoclonal Human IgM Autoantibody which Binds Recombinant Human and Mouse Tumor Necrosis Factor-α" *Cell. Immunol.*, 152:556-68 (1993).

Boyle, P. et al. "The B5 Monoclonal Human Autoantibody Binds to Cell Surface TNFα on Human Lymphoid Cells and Cell Lines and Appears to Recognize a Novel Epitope" *Cell. Immunol.*, 152:569-81 (1993).

Brekke, O. et al., "Therapeutic Antibodies for Human Diseases at the Dawn of the Twenty-first Century," *Nature*, vol. 2:52-62 (2002).

Brorson et al., "Bracketed Generic Inactivation of Rodent Retroviruses by Low pH Treatment; for Monoclonal Antibodies and Recombinant Proteins," Biotechnology and Bioengineering,; vol. 82(3): 321-329 (2003).

Bruggemann et al., "Production of human antibody repertoires in transgenic mice" Cur. Op. Biotechnol. ;455-458 (1997).

Bruggemann, M., Neuberger, M.S., "Strategies for expressing human antibody repertoires in transgenic mice," *Immunol. Today* 17:391-397 (1996).

Cai B, et al. "C-Terminal Lysine Processing of Human; Immunoglobulin G2 Heavy Chain in Vivo" Biotechnol. Bioeng. 2011;108: 404-412.

Cambridge Antibody Technology, advertisement of phage display services, Science vol. 253, No. 5018 (1991).

Carter et al., "Humanization of an anti-p185HER2 antibody for human cancer therapy," *Proc. Nat. Acad. Sci*89:4285-4289 (1992).

Chang KH, et al., "N-Acetylcysteine Increases the Biosynthesis of Recombinant EPO in Apoptotic Chinese Hamster Ovary Cells", Free Radic Res. 30(2):85-91, 1999.

Choo et al. "High-level production of a monoclonal antibody in murine myeloma cells by perfusion culture using a gravity settler" Biotechnology Progress, vol. 23, No. 1, Jan. 1, 2007, 225-231.

Chow, A. et al. "Effect of monoclonal antibody on human tumor necrosis factor (TNF MAb) on TNFα, IL-1β, and IL-6 levels in patients with sepsis syndrome" *Clinical Research*, 42:2 299A (1994).

Chua, FKF et al., "Hyper-stimulation of monoclonal antibody production by high osmolarity stress in eRDF medium", J. Biotechnology 37(3):265-275, Nov. 15, 1994.

Chung et al., "Utilization of Lysozyme Charge Ladders to Examine the Effects of Protein Surface; Charge Distribution on Binding Affinity in Ion Exchange Systems," Langmuir 26(2):759-768 (2010).

Chung et al., "Cetuximab-Induced Anaphylaxis and IgE Specific for Galactose-α-1, 3-Galactose", *N. Engl. J. Med.*, 358:11, pp. 1109-1117 (2008).

Cleland, J. et al., "A Specific Molar Ratio of Stabilizer to Protein is Required for Storage Stability of a Lyophilized Monoclonal Antibody," *Journal of Pharmaceutical Sciences*, vol. 90(3):310-321 (2001).

Cohen, J., et al., "Intersept: An international, multicenter, placebo-controlled trial of monoclonal anitbody to human tumor necrosis factor-α in patients with sepsis," *Crit Care Med*, vol. 24(9):1431-1440 (1996).

Cox, J. et al. "A directory of human germ-line Vκ segments reveals a strong bias in their usage" *Eur. J. Immunol.*, 24(2):827-36 (1994).

Cromwell (GAB'04 Abstracts—GE Healthcare Life Sciences, Franc Oct. 3-5, 2004, pp. 17-18 published 2005).

Daugherty, et al. Formulation and Delivery Issues for Monoclonal Antibody Therapeutics. Advanced Drug Delivery Reviews, 2006. vol. 58, pp. 686-706.

Davies et al., "Antibody VH domains as small recognition units." *Biotechnology*, 13:475-479 (1995).

Department of Surgery, University of Toronto, Annual Report (1998-1999)(348 pages).

DePhillips et al., "Determinants of protein retention characteristics on cation-exchange adsorbents,"; Journal of Chromatograph A, 933:57-72 (2001).

deZongotita et al., "Phosphate feeding improves high-cell-concentration NS0 myeloma cell culture performance for monoclonal antibody production" Biotechnology and Bioengineering. 2000, 69: 566-576.

Dick et al: "C-terminal lysine variants in fully human monoclonal antibodies: Investigation of test methods; and possible causes", Biotechnology and Bioengineering, vol. 100, No. 6, Aug. 15, 2008, pp. 1132-1143.

Dolezal, et al., "*Escherichia coli* Expression of a Bifunctional Fab-peptide Epitope Reagent for the Rapid Diagnosis of HIV-1 and HIV-2", *Immunotechnology*, 1:197-209 (1995).

Doring, E., "Identification and Characterization of a TNFa Antagonist Derived from a Monoclonal Antibody" (1994) *Mol. Immunol* .31(14): 1059-1067.

(56) References Cited

OTHER PUBLICATIONS

Elliot et al., "Repeated therapy with monoclonal antibody to tumour necrosis factor α (cA2) in patients with rheumatoid arthritis" (1994) *Lancet*, 344:1125-1127.

Elliot, "Treatment of rheumatoid arthritis with chimeric monoclonal antibodies to tumor necrosis factor α" (1993) *Arthritis & Rheumatism*, 36(12):1681-1690.

Emery, P. "Adalimumab therapy: Clinical findings and implications for integration into clinical guidelines for rheumatoid arthritis." *Drugs of Today*, 41(3): p. 155-153. (2005).

Ewert et al., "Biophysical Properties of Human Antibody Variable Domains," J. Mol. Biol. 324: 531-; 553 (2003).

Exhibit dated Aug. 1, 2013 and cited by plaintiff in Civil Action No. 09-40089-FDS providing Declaration by Jochen Salfeld, dated Jan. 17, 2013.

FDA Package insert for Adalimumab, Sep. 26, 2003, pp. 1-18.

Feldmann, "Anti-TNF-alpha Therapy of Rheumatoid Arthritis: What Have We Learned?" (2001) *Annu. Rev. Immunol.*, 19:163-196.

Figini, "In Vitro assembly of Repertoires of Antibody Chains on the Surface of Phage by Renaturation" (1994) *J. Mol. Biol.*, 239:68-78.

Fishwild et al., "High-avidity human IgG kappa monoclonal antibodies from a novel strain of minilocus transgenic mice" (1996) *Nature Biotechnology*, 14:845-851.

Fomsgaard, "Auto-antibodies to Tumor Necrosis Factor α in Healthy Humans and Patients with Inflammatory Diseases and Gram-Negative Bacterial Infections" (1989) *Scand. J. Immunol.* 30:219-23.

Foote, J., "Antibody framework residues affecting the conformation of the hypervariable loops" (1992) *J. Mol. Biol.*, 224(2):487-499.

Freitag et al., "Displacement chromatography in biotechnological downstream processing," J. Chromatography, (1995) 691(1):101-112.

Gagnon et al., "A Systematic Approach to the Purification of Monoclonal Antibodies," *LC-GC* 11 (1):26-34 (1993).

Gatto, B. "Biologics targeted at TNF: design, production and challenges", Reumatismo 58(2):94-103, 2006.

Genbank Entry for CHO Cathepsin L., EGW13555, Aug. 25, 2011, pp. 1-2.

Ghaderi, et al., "Implications of the Presence of N-glycolylneuraminic acid in Recombinant Therapeutic Glycoproteins", *Nature Biotechnology*, 28(8):863-868 (2010).

Ghaderi, et al., "Production platforms for biotherapeutic glycoproteins. Occurrence, impact, and challenges of non-human sialylation", *Biotechnology and Genetic Engineering Reviews*, 28:147-176 (2012).

Gonzalez et al. "Purification of Lactic Acid from Fermentation Broths by Ion-Exchange Resins" Ind. Eng. Chem. Res. 45:3243 (2006).

Graf et al., "Ion exchange resins for the purification of monoclonal antibodies from animal cell culture" Bioseparation 4 (1) :7-20 (Feb. 1994). ;4 (1) :7-20 (Feb. 1994).

Gram et al., "In vitro selection and affinity maturation of antibodies from a naive combinatorial immunoglobulin library" (1992) *PNAS*, 89:3576-3580.

Gramer et al., "Glycosidase Activities of the 293 and NS0 Cell Lines, and of an Antibody-Producing Hybridoma Cell Line", *Biotechnology and Bioengineering*, 43:423-428 (1994).

Green et al., "Antigen-specific human monoclonal antibodies from mice engineered with human Ig heavy and light chain YACs" (1994) *Nature Genetics*, 7:13-21.

Griffiths et al., "Isolation of high affinity human antibodies directly from large synthetic repertoires" (1994) *EMBO J.*, 13:3245-3260.

Griffiths, "Human anti-self antibodies with high specificity from phage display libraries" (1993) *The EMBO J.* 12(2):725-34.

Grunberg, J. et al., "High-Yield Production of Recombinant Antibody Fragments in HEK-293 Cells Using Sodium Butyrate", BioTechniques 34(5):968-972, May 2003.

Han, Kyu Oh et al., "Effect of N-Acetylcystein on Butyrate-Treated Chinese Hamster Ovary Cells to Improve the Production of Recombinant Human Interferon-β-1a", Biotechnol. Prog. 21(4):1154-1164, 2005.

Harlow and Lane, Antibodies a Laboratory Manual, Purification of Antibodies by using a; Deae-matrix (Batch), Storing and Purifying Antibodies; Chapter 8: 302-303 (1988).

Harris et al. "Processing of C-terminal lysine and argnine residues of proteins isolated from mammalian cell culture" Journal of Chromatography, (1995) 705; 129-123.

Harrison et al., "Protein N-Glycosylation in the Baculovirus-Insect Cell Expression System and; Engineering of Insect Cells to Produce "Mammalianized" Recombinant Glycoproteins," Advances in; Virus Research, 68:159-191 (2006).

Hawkins, "Selection of Phage Antibodies by Binding Affinity Mimicking Affinity Maturation" (1992) *J. Mol. Biol.*, 226:889-896.

Heidemann, R. et al., "The use of peptones as medium additives for the production of a recombinant therapeutic protein in high density perfusion cultures of mammalian cells", Cytotechnology 32:157-167, 2000.

Helms et al., "Destabilizing loop swaps in the CDRs of an immunoglobulin VL domain," Protein; Science 4:2073-2081 (1995).

Hiatt et al., "Characterization and Applications of Antibodies Produced in Plants", *Intern. Rev. Immunol.*, 10:139-152 (1993).

Hiatt et al., "Production of Antibodies in Transgenic Plants", *Nature*, 342:76-78 (1989).

Hillgren, A. et al., "Protection mechanism of Tween 80 during freeze-thawing of a model protein LDH," *International Journal of Pharmaceutics*, vol. 237:57-69 (2002).

Hokke et al., "Sialylated Carbohydrate Chains of Recombinant Human Glycoproteins Expressed in Chinese Hamster Ovary Cells Contain Traces of N-glycolylneuraminic acid", *FEBS*, 275:9-14 (1990).

Holler, "Modulation of Acute Graft-Versus-Host Disease After Allogeneic Bone Marrow Transplantation by Tumor Necrosis Factor -alpha (TNF-alpha) Release in the Course of Pretransplant Conditioning: Role of Conditioning Regimens and Prophylactic Application of a Monoclonal Antibody Neutralizing Human TNF-alpha (MAK 195F)" (1995) *Blood*, 86(3):890-899.

Holt, L. et al., "Domain antibodies: proteins for therapy," Trends in Biotechnology, vol. 21(11):484-490 (2003).

Hoogenboom et al., "By-passing immunisation : Human antibodies from synthetic repertoires of germline VH gene segments rearranged in vitro" (1992) *J. Mol. Biol.*, 227:381-388.

Hoogenboom, "Converting rodent into human antibodies by guided selection" (1996) *Antibody Engineering*, Oxford University Press, pp. 169-185.

Horvath et al: "Characterization of a Monoclonal Antibody Cell Culture Production Process Using a Quality by; Design Approach", Molecular Biotechnology, vol. 45, No. 3, Jul. 1, 2010, pp. 203-206.

Huang et al. "Effects of anti-TNF monoclonal antibody infusion in patients with hairy cell leukaemia" (1992) *Br. J. Haematol.*, 81(2):231-234.

Hui et al., "Recovery and purification process development for monoclonal antibody production," MABS (2010) 2(5):480-499.

Huse, "Generation of a large combinatorial library of the immunoglobulin repertoire in phage lambda" (1989) *Science*, 246:1275-81.

Jakobovits, A., "Production of fully human antibodies by transgenic mice" (1995) *Curr. Op. Biotechnol.*, 6:561-566.

Jespers, "Guiding the Selection of Human Antibodies from Phage Display Repertoires to a Single Epitope of an Antigen" (1994) *Bio/Technology*, 12:899-903.

Johnson et al. (Archives of Biochemistry and Biophysics 444 (2005) 7-14).

Kalyanpur, M., "Downstream Processing in the Biotechnology Industry" Molecular Biotechnology, vol. 22:87-98 (2002).

Karampetsou et al. (Q J Med 2010; 103:917-928).

Kaschak et al: "Characterization of the basic charge variants of a human IgGl: Effect of copper concentration in cell culture media", MABS, vol. 3, No. 6, Nov. 1, 2011, pp. 577-583.

Kazuaki, F. et al., "Enhancement of productivity of recombinant α-amidating enzyme by low temperature culture", Cytotechnology 31:85-94, 1999.

Kempeni, "Update on D2E7: a fully human anti-tumour necrosis factor -alpha monoclonal antibody" (2000) *Ann. Rheum. Dis.*, 59(Suppl. I)144-145.

(56) References Cited

OTHER PUBLICATIONS

Kempeni, J, "Preliminary results of early clinical trials with the fully human anti-TNFα monoclonal antibody D2E7", Ann. Rheum. Dis., 1999, pp. 170-172, vol. 58, (Suppl. I).

Kempf, C, et al. "Virus inactivation during production of intravenous immunoglobulin." *Transfusion* 1991; vol. 31: p. 423-427.

Khawli et al, "Charge variants in IgGI: Isolation, characterization, in vitro binding properties and pharmacokinetics in rats", MABS, vol. 2, No. 6, Nov. 1, 2010, pp. 613-624.

Kim, NS. et al., "Inhibition of sodium butyrate-induced apoptosis in recombinant Chinese hamster ovary cells by constitutively expressing antisense RNA of caspase-3", Biotechn. & Bioengin. 78(2):217-228, 2002.

Knight et al., "Construction and initial characterization of a mouse-human chimeric anti-TNF antibody" (1993) *Mol. Immunol.*, 30(16):1443-1453.

Kopaciewicz et al., "Retention Model for High-Performance Ion-Exchange Chromatography,"; Journal of Chromatography, 266:3-21 (1983).

Lerner, "Antibodies without immunization" (1992) *Science*, 258:1313-1314.

Lewis, "Use of alanine scanning mutagenesis to improve the affinity of an anti gp120 (HIV) antibody" (1994) *J. Cell. Biochem.*, 18D:215.

Li, F. et al., "Current Therapeutic Antibody Production and Process Optimization" BioProcessing Journal, vol. 4(5):23-30 (2005).

Lifely et al., "Glycosylation and Biological Activity of CAMPATH-1H Expressed in Different Cell Lines and Grown Under Different Culture Conditions", *Glycobiology*, 5(8):813-822 (1995).

Logan, John S. "Transgenic Animals: Beyond 'Funny Milk'", *Current Opinion in Biotechnology*, 4:591-595 (1993).

Lonberg et al., "Antigen-specific human antibodies from mice comprising four distinct genetic modifications" (1994) *Nature*, 368:856-859.

Lonberg et al., "Human Antibodies from Transgenic Mice" (1995) *Int. Rev. Immunol.*, 13:65-93.

Low, "Mimicking Somatic Hypermutation: Affinity Maturation of Antibodies Displayed on Bacteriophage Using a Bacterial Mutator Strain" (1996) *J. Mol. Biol.*, 260:359-368.

Luo et al: "Probing of C-terminal lysine variation in a recombinant monoclonal antibody production using Chinese hamster ovary cells with chemically defined media", Biotechnology and Bioengineering, vol. 109, No. 9, Apr. 11, 2012, pp. 2306-2315.

Ma, et al., "Generation and Assembly of Secretory Antibodies in Plants", *Science*, 268:716-719 (1995).

Maeda, et al., "Analysis of Nonhuman N-Glycans as the Minor Constituents in Recombinant Monoclonal Antibody Pharmaceuticals", *Anal. Chem.*, 84:2373-2379 (2012).

Mahler, et al. Induction and analysis of aggregates in a liquid IgG1-antibody formulation. Eur J Pharm Biopharm. 2005, 59(3):407-17; p. 408; col. 1-2; p. 409; col. 2, "2.2.2 Stirring stress".

Marks et al., "Human antibody fragments specific for human blood group antigens from a phage display library" (1993) *Bio/Technology*, 11:1145-1150.

Marks et al., "Molecular evolution of proteins on filamentous phage. Mimicking the strategy of the immune system" (1992) *J. Biol. Chem.* 267:16007-16010.

Marks, "By-passing immunization: Human antibodies from V-gene libraries displayed on phage" (1991) *J. Mol. Biol.*, 222:581-597.

Marks, "Human Monoclonal Antibodies from V-gene Repertoires Expressed on Bacteriophage." in *Antibody Engineering*, Second Edition, edited by Carl A.K. Borrebaeck (1995), pp. 53-88. New York: Oxford Univ. Press.

Marks, JD., "By-Passing Immunization: Building High Affinity Human Antibodies by Chain Shuffling" (1992) *Biotechnology*, 10:779-783.

Martin, A.C.R. "Accessing the Kabat antibody sequence database by computer" (1996)*PROTEINS: Structure, Function and Genetics*, 25:130-133.

Medynski, "Phage Display: All Dressed Up and Ready to Role" (1994) *Bio/Technology*, 12:1134-1136.

Mendez et al., "Functional transplant of megabase human immunoglobulin loci recapitulates human antibody response in mice" (1997) *Nature Genetics*, 15:146-156.

Meuwly, F. et al., "Conversion of a CHO cell culture process from perfusion to fed-batch technology without altering product quality", J.Biotechn. 123:106-116, 2006.

Miller et al. "Characterization of site-specific glycation during process development of a human therapeutic monoclonal antibody" Journal of Pharmaceutical Sciences, vol. 100, No. 7, Jul. 2011, 2543-2550.

Millipore, "Pellicon 2 Filters and Holders," 2003, pp. 1-8.

Moore, A., et al., "Effects of temperature shift on cell cycle, apoptosis and nucleotide pools in CHO cell batch cultures", Cytotechnology, 23:47-54, 1997.

Möller, Monoclonal antibodies to human tumor necrosis factor α: in vitro and in vivo application (1990) *Cytokine*, 2(3):162-169.

Neuberger M. et al., "Mice perform a human repertoire" (1997) *Nature*, 386:25-26.

Ngo et al., "Kosmotropes enhance the yield of antibody purified by affinity chromatography using immobilized bacterial immunoglobulin binding proteins," Journal of Immunoassay & Immunochemistry, (2008) 29(1):105-115.

Nilsson, "Antibody engineering" (1995) *Current Opinion in Structural Biology*, 5:450-456.

Nogal, B., Chhiba, K. and Emery, J. C. (2012), Select host cell proteins coelute with monoclonal antibodies in protein a chromatography. Biotechnol Progress, 28: 454-458.

Noguchi et al., "Failure of Human Immunoresponse to N-Glycolylneuraminic Acid Epitope Contained in Recombinant Human Erythropoietin", *Nephron*, 72:599-603 (1996).

Noguchi et al., "Immunogenicity of N-Glycolylneuraminic Acid-Containing Carbohydrate Chains of Recombinant Human Erythropoietin Expressed in Chinese Hamster Ovary Cells", *J. Biochem.*, 117:59-62 (1995).

Oh, D-K. et al., "Increased erythritol production in fed-batch cultures of *Torula* sp. by controlling glucose concentration", J. Industrial Microb. & Biotechn. 26(4): 248-252, 2001.

Oh, SKW, et al., "Substantial Overproduction of Antibodies by Applying Osmotic Pressure and Sodium Butyrate", Biotechn. Bioengin. 42(5):601-610, 1993.

Osbourn, "From rodent reagents to human therapeutics using antibody guided selection" (2005) *Methods*, 36(1):61-68.

Perchiacca et al., "Aggregation-resistance domain antibodies engineered with charged mutations; near the edges of the complementarity-determining regions," Protein Engineering Design & Selection, 25: 10 (591-601) 2012.

Pietersz et al., "In vitro and in vivo Antitumor Activity of a Chimeric anti-CD19 Antibody", *Cancer Immunol. Immunother.*, 41:53-60 (1995).

Potter et al., "Antibody Production in the Baculovirus Expression System", *Intern. Rev. Immunol.*, 10:103-112 (1993).

Poul et al., "Design of Cassette Baculovirus Vectors for the Production of Therapeutic Antibodies in Insect Cells", *Immunotechnology*, 1:189-196 (1995).

Queen, C., "A humanized antibody that binds to the interleukin 2 receptor" (1989) *Proc. Natl. Acad. Sci. USA*, 86(24):10029-10033.

Rader et al. "A phage display approach to rapid antibody humanization: Designed combinatorial V gene libraries" (1998) *Proc Natl Acad Sci USA*, 95:8910-8915.

Raju, TS. "Glycosylation Variations with Expression Systems and Their Impact on Biological Activity of Therapeutic Immunoglobulins", *BioProcess International.*, 44-53 (2003).

Reichert JM., et al., "Monoclonal antibody successes in the clinic", Nature Biotech. 23(9):1073-1078, 2005.

Reinhart, "Assessment of the safety and efficacy of the monoclonal anti-tumor necrosis factor antibody-fragment, MAK 195F, in patients with sepsis and septic shock: a multicenter, randomized, placebo-controlled, dose-ranging study" (1996) *Crit. Care Med.*, 24(5):733-742.

Rheinwald JG, et al., "Growth of Cultured Mammalian Cells on Secondary Glucose Sources", Cell, 287-293, 1974.

(56) References Cited

OTHER PUBLICATIONS

Ridder et al., "Generation of Rabbit Monoclonal Antibody Fragments from a Combinatorial Phage Display Library and Their Production in Yeast *Pichia pastoris*", *Biotechnology*, 13:255-260 (1995).
Riechmann, "Phage display and selection of a site-directed randomized single-chain antibody Fv fragment for its affinity improvement" (1993) *Biochemistry*, 32(34):8848-8855.
Rube et al. (Int. J. Radiation Oncology Biol. Phys., vol. 56, No. 5, pp. 1414-1425,2003).
Rudikoff et al., "Single amino acid substitution altering antigen-binding specificity" (1982) *Proc. Natl. Acad. Sci. USA*, 70:1979-1983.
Salfeld, "Development of a Fully Human Antibody to TNF by Phage Display Technology," IBC Conference, *Antibody Engineering*, San Diego (Dec. 1996), pp. 1-36.
Sandadi, S. et al., "Heuristic Optimization of Antibody Production by Chinese Hamster Ovary Cells", Biotech. Progress, American Institute of Chem. Engineers: 21(5): 1537-1542, 2005.
Sandhu, J. "Protein engineering of antibodies" (1992) *Critical Reviews in Biotechnology*, 12:437-462.
Santora et al., "Characterization of recombinant human monoclonal tissue necrosis factor-alpha antibody using cation exchange HPLC and capillary isoelectric focusing," Analytical Biochemistry, (1999) 275:98-108.
Santora, "Characterization of Noncovalent Complexes of Recombinant Human Monoclonal Antibody and Antigen Using Cation Exchange, Size Exclusion Chromatography, and BIAcore" (2001) *Analytical Biochemistry*, 299:119-129.
Sato et al, "Stimulation of monoclonal antibody production by human-human hybridoma cells with an elevated concentration of potassium or sodium phosphate in serum-free medium," Cytotechnology 2:63-67, 1989.
Seresht et al., "The impact of phosphate scarcity on pharmaceutical protein production in *S. cerevisiae*: linking transcriptomic insights to phenotypic responses" Microbial Cell Factories. 2011, 10: 104.
Sheeley et al., "Characterization of Monoclonal Antibody Glycosylation: Comparison of Expression Systems and Identification of Terminal α-Linked Galactose", *Anal. Biochem.*, 247(1):102-110 (1997).
Sheikh et al., "Studies of the digestion of bradykinin, lysyl bradykinin, and kinin-degradation products by carboxypeptidases A, B, and N;". Biochemical Pharmacology. 1986, 35: 1957-1963.
Shih, "Effects of Anions on the Deamidation of Soy Protein". Journal of Food Science. 1991, 56: 452-454.
Shukla et al., "Host cell protein clearance during protein A chromatography: development of an improved column wash step," Biotechnology Progress, (2008) 24(5):1115-1121.
Shukla et al., "Recent advances in large-scale production of monoclonal antibodies and related proteins," Trends in Biotechnology, (2010) 28(5):253-261.
Sioud et al., "Characterization of naturally occurring autoantibodies against tumour necrosis factor-alpha (TNF-α): in vitro function and precise epitope mapping by phage epitope library" (1994) *Clin. Exp. Immunol.*, 98:520-525.
Sung, Y.H. et al., "Yeast hydrolysate as a low-cost additive to serum-free medium for the production of human thrombpoietin in suspension cultures of Chinese hamster ovary cells", *Applied Microbilolgy and Biotechnology* 63:5, 527-536, 2004.
Takagi, M. et al., "The effect of osmolarity on metabolism and morphology in adhesion and suspension chinese hamster ovary cells producing tissue plasminogen activator", Cytochnology 32:171-179, 2000.
Tamura et al., "Structural correlates of an anticarcinoma antibody: identification of specificity-determining residues (SDRs) and development of a minimally immunogenic antibody variant by retention of SDFs only," *J. Immun.* (2000) 164:1432-1441.
Tan et al. (Biotechnol. Appl. Biochem. (1999) 30, 59-64).
Taylor et al.,"Human immunoglobulin transgenes undergo rearrangement, somatic mutation and class switching in mice that lack endogenous IgM" (1994) *Int. Immunol.*, 6:579-591.

The pI Calculator available at the Sequence Manipulation Suite (see <http://bioinformatics.org/sms2/index.html>), downloaded Feb. 25, 2014, p. 1).
Thompson, "Affinity maturation of a high-affinity human monoclonal antibody against the third hypervariable loop of human immunodeficiency virus: use of phage display to improve affinity and broaden strain reactivity" (1996) *J. Mol. Biol.*, 256(1):77-88.
Thorp, "Tumour Necrosis Factor Induction of ELAM-1 and ICAM-1 on Human Umbilical Vein Endothelial Cells—Analysis of Tumour Necrosis Factor Receptor Interaction" (1992) *Cytokine*, 4(4): 313-319.
Tomiya et al., "Comparing N-glycan processing in mammalian cell lines to native and engineered; lepidopteran insect cell lines," Glycoconjugate Journal 21 :343-360 (2004).
Tomlinson, "The repertoire of human germline VH sequences reveals about fifty groups of VH segments with different hypervariable loops" (1992) *J. Mol. Biol.*, 227:776-98.
Tomlinson, "The structural repertoire of the human Vk domain" (1995) *The Embo J.*, 14(18):4628-38.
Tracey, "Tumor necrosis factor: A pleiotropic cytokine and therapeutic target" (1994) *Annu. Rev. Med.*, 45:491-503.
Tsuchiyama et al., "Comparison of anti-TNF alpha autoantibodies in plasma and from EBV transformed lymphocytes of autoimmune and normal individuals" (1995) *Hum. Antibod. Hybridomas*, 6(2):73-76.
Vallee B et al. "The role of zinc in carboxypeptidase" The Journal of Biological Chemistry, (1960) 235, 1; 64-69.
Valliere-Douglass et al., "Glutamine-linked and Non-consensus Asparagine-linked Oligosaccharides Present in Human Recombinant Antibodies Define Novel Protein Glycosylation Motifs", *J. Biol. Chem.*, 285:16012-16022 (2010).
Van Der Poll, "Effect of postponed treatment with an anti-tumour necrosis factor (TNF) F(ab')2 fragment on endotoxin-induced cytokine and neutrophil responses in chimpanzees" (1995) *Clin. Exp. Immunol.*, 100:21-25.
Van Lent PL, et al. "The impact of protein size and charge on its retention in articular cartilage" J Rheumatol. Aug. 1987;14(4):798-805.
Varasteh et al. Optimization of Anti-Rh D Immunoglobulin Stability in the Lyphiliization Process. Iranian Journal of Basic Medical Sciences, Spring 2008, vol. 11, No. 1. pp. 55-61.
Vaughan, "Human antibodies by design" (1998) *Nature Biotechnology*, 16:535-539.
Wagner et al., "Antibodies generated from human immunoglobulin miniloci in transgenic mice" (1994) *Nucl. Acids Res.* 22:1389-1393.
Wagner et al., "The diversity of antigen-specific monoclonal antibodies from transgenic mice bearing human immunoglobulin gene miniloci" (1994) *Eur. J. Immunol.*, 24:2672-2681.
Ward, "Binding activities of a repertoire of single immunoglobulin variable domains secreted from *Escherichia coli*" (1989) Nature, 341:544-546.
Wedemayer et al., "Structural insights into the evolution of an antibody combining site" (1997) *Science*, 276:1665-1669.
Wiendl et al. (BioDrugs. 2002;16(3):183-200).
Williams et al., "Kinetic analysis by stopped-flow radiationless energy transfer studies: effect of anions on the activity of carboxypeptidase A". Biochemistry. 1986, 25, 94-100.
Winter, "Humanized antibodies" (1993) *Immunol. Today*, 14(6):243-246.
Winter, "Making antibodies by phage display technology" (1994) *Annu. Rev. Immunol.*, 12:433-455.
Wurm, FM, "Production of recombinant protein therapeutics in cultivated mammalian cells", Nature Biotechnology 22(11):1393-1398, 2004.
Yigzaw et al., "Exploitation of the adsorptive properties of depth filters for host cell protein removal during monoclonal antibody purification," Biotechnology Progress, (2006) 22(1):288-296.
Yumioka et al., "Screening of effective column rinse solvent for Protein-A chromatography," Protein Expression and Purification, (2010) 70(2): 218-223.
Zatarain-Rios E and Mannik M, "Charge-charge interactions between articular cartilage and cationic antibodies, antigens, and immune complexes," Arthritis Rheum. Nov. 1987;30(1 1):1265-73.

(56) References Cited

OTHER PUBLICATIONS

Zhang et al., "Isolation and characterization of charge variants using cation exchange displacement chromatography," 1218(31): 5079-5086, 2011.
Zou et al., "Dominant expression of a 1.3 Mb human Ig kappa locus replacing mouse light chain production" (1996) *FASEB J.*, 10:1227-1232.
Boswell et al. "Effects of Charge on Antibody Tissue Distribution and Pharmacokinetics" Bioconjugate Chem.(21) 2153-2163 (2010).
Schiestl et al. "Acceptable changes in quality attributes of glycosylated biopharmaceuticals" Nature Biotechnology, 29(4), 310-312 (2011).
Senczuk et al. "Hydrophobic interaction chromatography in dual salt system increases protein binding capacity" Biotechnology and Bioengineering, 103(5), 930-935 (2009).
U.S. Appl. No. 14/575,691, filed Dec. 18, 2014.
U.S. Appl. No. 14/584,492, filed Dec. 29, 2014.
U.S. Appl. No. 14/584,619, filed Dec. 29, 2014.
"Memorandum in Support of Centocor's Motion for Summary Judgment No. 1 that All Asserted Claims Are Invalid for Lack of Written Description", dated Aug. 1, 2013 and submitted by defendant in Civil Action No. 09-40089-FDS, 28 pages.
"Memorandum in Support of Centocor's Motion for Summary Judgment No. 2 that All Asserted Claims Are Invalid for Lack of Enablement", dated Aug. 1, 2013 and submitted by defendant in Civil Action No. 09-40089-FDS, 22 pages.
"Memorandum in Support of Centocor's Motion for Summary Judgment No. 4 that Claims Encompassing Non-recombinant Human Antibodies Are Invalid for Failing to Meet the Requirements of 35 U.S.C. § 112", dated Aug. 1, 2013 and submitted by defendant in Civil Action No. 09-40089-FDS, 21 pages.
"Memorandum in Support of Centocor's Motion No. 3 for Summary Judgment that the 394 and 031 Patents Are Invalid for Under 35 U.S.C. § 102(f) for Failing to Name the Proper Inventors", dated Aug. 1, 2013 and submitted by defendant in Civil Action No. 09-40089-FDS, 13 pages.
"Memorandum in Support of Centocor's Motion No. 6 for Summary Judgment that References Dated Before Feb. 10, 1997 Qualify as Prior Art to the 394 and 031 Patents", dated Aug. 1, 2013 and submitted by defendant in Civil Action No. 09-40089-FDS, 16 pages.
"Plaintiffs' Memorandum in Support of Their Motion for Partial Summary Judgment", dated Aug. 1, 2013 and submitted by plaintiff in Civil Action No. 09-40089-FDS, 49 pages.
"Plaintiffs' Rule 56.1 Statement of Undisputed Material Facts in Support of Their Motion for Partial Summary Judgment", dated Aug. 1, 2013 and submitted by plaintiff in Civil Action No. 09-40089-FDS, 13 pages.
Abbott Laboratories Press Release, "Abbott Laboratories Receives FDA Approval Earlier Than Expected for HUMIRA (adalimumab) for the Treatment of Rheumatoid Arthritis," Dec. 31, 2002, pp. 1-4.
Andersen DC, Goochee CF. The effect of cell-culture conditions on the oligosaccharide structures of secreted glycoproteins. Curr Opin Biotechnol. Oct. 1994;5(5):546-9.
Anonymous, "SACHEM Displacement Chromatography," Aug. 29, 2012, Retrieved from the internet: <http://www.displacementchromatography.com>, retrieved on Jul. 30, 2014.
Averginos, Gab '04 Abstracts—GE Healthcare Life Sciences, "HUMIRA manufacturing: challenges and the path taken", France, Oct. 3-5, 2004, published 2005, pp. 14-16.
Barnes et al., "Stability of Protein Production from Recombinant Mammalian Cells," Biotechnology and Bioengineering, 81:6, Mar. 20, 2003, pp. 631-639.
BD Bioscience Product Description for BBL Phytone Peptone (Advanced Processing, Third Edition) (Sep. 23, 2010) (www.bdbiosciences.com/external_files/Doc_Recon_2.0/ab/others/Phytone_Soytone.pdf), (last accessed Jan. 8, 2015), 4 pages.
Burteau et al. (in Vitro Cell Dev Biol—Animal, Jul. / Aug. 2003. 39-291-296).

Byun, et al. Archives of Biochemistry and Biophysics, "Transport of anti-IL-6 binding fragments into cartilage and the effects of injury," 532 (2013), pp. 15-22.
Canghai, Lu et al.: "A T-flask based screening platform for evaluating and identifying plant hydrolysates for a fed-batch cell culture process", Cytotechnology, Kluwer Academic Publishers, DO, vol. 55, No. 1, Aug. 18, 2007, pp. 15-29.
Charter, Edward A., "A New Process for the Separation and Purification of Egg Yolk; Antibodies," BASc., The University of British Columbia; A Thesis; Apr. 1993, 163 pages.
Chumsae, Chris et al.: "Arginine modifications by methylglyoxal: discovery in a recombinant monoclonal antibody and contribution to acidic species.", Analytical Chemistry Dec. 3, 2013, vol. 85, No. 23, Dec. 3, 2013, pp. 11401-11409.
Clincke, M. et al., "Effect of surfactant pluronic F-68 on CHO cell growth, metabolism, production, and glycosylation of human recombinant IFN-γ in mild operating conditions," Biotechnol. Prog. 27(1): 180-190, 2011.
Crowell, C.K., et al., Amino acid and manganese supplementation modulates the glycosylation state of erythropoietin in a CHO culture system. Biotechnology and bioengineering, Feb. 15, 2007; 96(3):538-549.
Du et al., "Chromatographic analysis of the acidic and basic species of recombinant monoclonal antibodies" *MAbs*, (2012) Sept-Oct.; 4(5):578-85.
Ellison, Jay W. et al., "The Nucleotide Sequence of a Human Immunoglobulin C $\gamma_1$ Gene," Nucleic Acids Research, vol. 10, No. 13 (1982), 9 pages.
Erbitux (cetuximab) label, *Revised* Aug. 2013, 8 pages.
Exhibit dated Aug. 1, 2013 and cited by defendant in Civil Action No. 09-40089-FDS providing the Jun. 23, 2009 trial transcript of the PM session in the matter of *Centocor, et al.* v. *Abbott Laboratories*, 50 pages.
Exhibit dated Aug. 1, 2013 and cited by defendant in Civil Action No. 09-40089-FDS providing the trial transcript in the matter of *Abbott Laboratories, et al.* v. *The Mathilda and Terrance Kennedy Institute*, S.D.N.Y., 90 pages.
Exhibit dated Aug. 1, 2013 and cited by plaintiff in Civil Action No. 09-40089-FDS providing excerpts from the File History of U.S. Appl. No. 12/578,487, 5 pages.
Exhibit dated Aug. 1, 2013 and cited by defendant in Civil Action No. 09-40089-FDS providing the Jun. 24, 2009 trial transcript of the AM session in the matter of *Centocor, et al.* v. *Abbott Laboratories*, E.D. TX., 42 pages.
Exhibit dated Aug. 1, 2013 and cited by defendant in Civil Action No. 09-40089-FDS providing the Sep. 20, 2012 Day 8 trial transcript in the matter of *Abbott* v. *Centocor Ortho Biotech Inc.*, D. MA., 71 pages.
Exhibit dated Aug. 1, 2013 and cited by plaintiff in Civil Action No. 09-40089-FDS providing Declaration by Jochen Salfeld, dated Jan. 17, 2013, 40 pages.
Feng et al., "Cell Culture Processes for Monoclonal Antibody Production," mAbs, 2:5, 466-477, Sep./Oct. 2010.
Fleisher B., Mechanism of glycosylation in the Golgi apparatus. J Histochem Cytochem, Aug. 1983; 31(8):1033-1040.
Folk et al., "Carboxypeptidase B, Purification and Characterization of the Porcine Enzyme," J. Biological Chem, 1960, 235:2272-2277.
Goochee CF The Oligosaccharides of Glycoproteins: Bioprocess Factors Affecting Oligosaccharide Structure and their Effect on Glycoprotein Properties. Nature Biotechnology Dec. 1991 1346-1355.
Gramer M Jet Al: "Modulation of Antibody Galactosylation Through Feeding of Uridine, Manganese Chloride, and Galactose",Biotechnology and Bioengineering, Wiley & Sons, Hoboken, NJ, US,vol. 108, No. 7, Jul. 1, 2011, pp. 1591-1682.
Gramer, M.J., et al., "Manipulation of Antibody Glycoforms in a High-Yield GS-CHO Process to Meet Comparability Requirements", *Biotechnology and Bioengineering*, vol. 108, No. 7, Jul. 2011, pp. 1591-1602.
Gu, X. et al: "Improvement of interferon-gamma sialylation in Chinese hamster ovary cell culture by feeding of N-acetylmannosamine",Biotechnology and Bioengineering, Wiley & Sons, Hoboken, NJ, US, vol. 58, No. 6, Jun. 20, 1998, pp. 642-648.

(56) References Cited

OTHER PUBLICATIONS

Harlow et al., Eds ("Antibodies: A Laboratory Manual" 1988. Cold Spring Harbor Laboratory Press, Chapter 7, pp. 245, 247,and 253).
Harris, Reed J. et al., "Structural Characterization of a Recombinant CD4-IgG Hybrid Molecule," Eur. J. Biochem. 194:611-620 (1990).
Hills, A.E. et al., Metabolic control of recombinant monoclonal antibody N-glycosylation in GS-NS0 cells, Biotechnology and Bioengineering, Oct. 20, 2001; 75(2):239-251.
Hossler et al.; "Improvement of mammalian cell culture performance through surfactant enabled concentrated feed media"; Biotechnology Progress; 29(4):1023-1033 (2013).
Hossler et al., (Glycobiology. 2009; 19 (9): 936-949).
Humira (adalimumab) label, *Revised* Sep. 2013, 87 pages.
Humira (adalimumab) prescribing information, Dec. 20, 2002, pp. 1-16.
HyClone™ CDM4CHO Catalog listing (last accessed Jan. 22, 2015), 1 page.
ICH Topic Q6B "Specifications:Test Procedures and Acceptance Criteria for Biotechnological/Biological Products," Sep. 1999, pp. 1-17.
International Preliminary Report on Patentability for Application No. PCT/US07/08359, dated Dec. 12, 2011, 5 pages.
International Preliminary Report on Patentability for Application No. PCT/US2011/060388, dated May 30, 2012, 9 pages.
International Preliminary Report on Patentability for Application No. PCT/US2013/031389, dated Oct. 21, 2014, pp. 1-10.
International Preliminary Report on Patentability for Application No. PCT/US2013/031485, dated Oct. 21, 2014, pp. 1-8.
International Preliminary Report on Patentability for Application No. PCT/US2013/031681, dated Oct. 21, 2014, pp. 1-8.
International Preliminary Report on Patentability for Application No. PCT/US2013/041958, dated Dec. 4, 2014, pp. 1-2.
International Preliminary Report on Patentability for Application No. PCT/US2013/031352 dated Nov. 25, 2014, pp. 1-10.
International Preliminary Report on Patentability for Application No. PCT/US2013/041954, dated Nov. 25, 2014, pp. 1-14.
International Search Report and Written Opinion for Application No. PCT/US2008/085066, dated May 12, 2009, 5 pages.
International Search Report and Written Opinion for Application No. PCT/US2010/033387, dated Aug. 7, 2012, 10 pages.
International Search Report and Written Opinion for Application No. PCT/US2013/031380, dated Feb. 5, 2014, 162 pages.
International Search Report and Written Opinion for Application No. PCT/US2013/041954, dated Dec. 17, 2013, 21 pages.
International Search Report and Written Opinion for Application No. PCT/US2013/041958, dated Dec. 17, 2013, 21 pages.
International Search Report and Written Opinion for Application No. PCT/US2013/065720, dated Dec. 16, 2013, 14 pages.
International Search Report and Written Opinion for Application No. PCT/US2013/065797, dated Nov. 26, 2013, 14 pages.
International Search Report and Written Opinion for PCT/US2012/035266, dated Feb. 7, 2013 (corresponds to U.S. Appl. No. 13/547,020), 4 pages.
International Search Report and Written Opinion from PCT/US2013/065749 dated Mar. 18, 2014, 18 pages.
International Search Report and Written Opinion from PCT/US2014/024151 dated Aug. 7, 2014, pp. 1-16.
International Search Report for Application No. PCT/IB03/04502, dated May 26, 2004, 6 pages.
International Search Report for Application No. PCT/US2011/060388 dated May 30, 2012, 6 pages.
International Search Report for Application No. PCT/US2013/031352, Dated Apr. 25, 2013, 6 pages.
International Search Report for Application No. PCT/US2013/031389, Dated Jun. 3, 2013, 4 pages.
International Search Report for Application No. PCT/US2013/031485, Dated Jun. 25, 2013, 4 pages.
International Search Report for Application No. PCT/US2013/031681, Dated Jun. 14, 2013, 6 pages.
International Search Report from PCT/US2014/024256 dated Jul. 30, 2014, pp. 1-15.
Invitation to Pay Additional Fees for International Application No. PCT/US2013/031380, Dated Nov. 28, 2013, 5 pages.
Invitation to Pay Additional Fees for International Application No. PCT/US2013/065749, Dated May 27, 2014, pp. 1-8.
Invitation to Pay Additional Fees for International Application No. PCT/US2014/026606, Dated Jul. 8, 2014, pp. 1-8.
Jayapal, Karthik P., et al., "Recombinant Protein Therapeutics from CHO Cells—20 Years and Counting," CHO Consortium, SBE Special Section, 40-47 (2007).
Jayme et al.; "Media formulation options and manufacturing process controls to safeguard against introduction of animal origin contaminants in animal cell culture"; Cytotechnology; 33:27-36 (2000).
Kwon et al., (Enzyme Microb Technol. 200; 26: 209-215).
Li, Feng, et al., "Cell Culture Processes for Monoclonal Antibody Production," mAbs 2:5, 466-477 (Sep.-Oct. 2010).
Luo et al., "Understanding of C-terminal lysine variants in antibody production using mammalian cells" Abstract of papers, ACS, Anaheim, CA, US, Mar. 2011, 1 page.
Luo, Ying et al.: "Development toward rapid and efficient screening for high performance hydrolysate lots in a recombinant monoclonal antibody manufacturing process.", Biotechnology Progress Jul. 2012, vol. 28, No. 4, Jul. 2012, pp. 1061-1068.
Martinelle, K. et al., Cells and Culture, Proceedings of the 20th ESACT Meeting v4 819-822, Jun. 17-20, 2007.
McAtee et al., "Isolation of monoclonal antibody charge variants by displacement chromatography," Current Protocols in Protein Science, 14 pages.
Parekh RB N-glycosylation and the production of recombinant glycoproteins vol. 7, Issue 5, p. 117-122, May 1989 Trends in Biotechnology.
Patel, T. P. et al.: "Different culture methods lead to differences in glycosylation of a murine IgG monoclonal antibody", Biochemical journal, The Biochemical Society, London, GB, vol. 285, No. 3, Jan. 1, 1992, pp. 839-845.
Pink, T. et al.: "Regulation of S-layer protein synthesis of bacillus stearothermophilus PV72 through variation of continuous cultivation conditions", Journal of Biotechnology, Elsevier Science Publishers, Amsterdam, NL, vol. 50, No. 2, Oct. 1, 1996, pp. 189-200.
Rea, J. C. et al.: "Validation of a pH gradient-based ion-exchange chromatography method for high-resolution monoclonal antibody charge variant separations", Journal of Pharmaceutical and Biomedical Analysis, New York, NY, US, vol. 54, No. 2, Jan. 25, 2011, pp. 317-323.
Routier, F. H. et al.: "The glycosylation pattern of a humanized IgGI antibody(D1.3) expressed in CHO cells", Glycoconjugate Journal, Chapman & Hall, GB, vol. 14, No. 2, Jan. 1, 1997, pp. 201-207.
Sakai et al.; "Use of nonionic surfactants for effective supply of phosphatidic acid in serum-free culture of Chinese hamster ovary cells"; Journal of Bioscience and Bioengineering; 92(3):256-261 (2001).
Satoh, Mitsuo et al.: "Non-Fucosylated therapeutic antibodies as next-generation therapeutic antibodies", Expert opinion on biological therapy, Ashley, London, GB, vol. 6, No. 11, Nov. 1, 2006, pp. 1161-1173.
Schwieterman, "Immunosuppression in Combination with Monoclonal Antibodies" in Biologic Agents in Autoimmune Disease (Mar. 2-4, 1995).
Shen, Amy Y. et al., "Recombinant DNA Technology and Cell Line Development," from "Cell Culture Technology for Pharmaceutical and Cell-Based Therapies," CRC Press, 2006, 15-40.
Sigma Catalog "RPMI1640" (last accessed Jan. 22, 2015), 3 pages.
Sigma MSDS for RMPI1640 (last accessed Jan. 22, 2015), 6 pages.
Sundaram et al., "An innovative approach for the characterization of the isoforms of a monoclonal antibody product," Mabs, 3(6):505-512, 2011.
Sung, Hyun Kim et al.: "Development of serum-free medium supplemented with hydrolysates for the production of therapeutic antibodies in CHO cell cultures using design of experiments", Applied Microbiology and Biotechnology, Springer, Berlin, DE, vol. 83, No. 4, Mar. 6, 2009, pp. 639-648.

(56) References Cited

OTHER PUBLICATIONS

Teichmann, S. Declaration dated Dec. 7, 2010 from opposition proceedings in EP 0929578, 6 pages.
Tess database "Hyclone" Trademark #76244963. Filing date Apr. 23, 2001. Live mark. Last accessed Jan. 21, 2015, 2 pages.
Tess database "Hyclone" Trademark #85769283. Filing date Sep. 30, 2012. Live mark. Last accessed Jan. 21, 2015, 2 pages.
Tharmalingam et al.; "Pluronic Enhances the Robustness and Reduces the Cell Attachment of Mammalian Cells"; Molecular Biotechnology; 39(2):167-177 (2008).
The Kennedy Institute of Rheumatology, 1995 Annual Scientific Report, "Anti-TNF trials and studies of mechanisms of action" 4 pages.
The MW Calculator available at the Sequence Manipulation Suite (see http://bioinformatics.org/sms2/index.html), downloaded Feb. 25, 2014, 2 pages.
The Statement on a Nonproprietary Name Adopted by the USAN Council for Adalimumab, p. 1, downloaded on May 19, 2011 from http://www.ama-assn.org/resources/doc/usan/adalimumab.doc. 1 page.
Wolff et al., "The Kinetics of Carboxypeptidase B Activity," J. Biological Chem, 1962, 237:3094-3099.
Wong N.S.C. et al: "An investigation of intracellular glycosylation activities in CHO cells: Effects of nucleotide sugar precursor feeding" Biotechnology and Bioengineering, vol. 187, No. 2,Oct. 1, 2010, pp. 321-336.
Worthington Biochemical Corporation, porcine pancreas carboxypeptidase B, one page, Feb. 25, 2012.
www.cygnustechnologies.com/product_detail/host-cell-protein-antibodies/anti-cho-h . . . Cygnus Technologies, Anti-CHO HCP (Apr. 18, 2012), 1 page.
Low, Nigel: thesis extract (1996) *Cambridge University*, 11 pages.
Ahmed, M. U.et al.; N-(Carboxyethyl)lysine, a product of the chemical modification of proteins by methylglyoxal, increases with age in human lens proteins; Biochem. J. 1997, 324, 565-570.
Ahmed, N. & Thornalley, P. J.; Peptide Mapping of Human Serum Albumin Modified Minimally by Methylglyoxal in Vitro and in Vivo; Ann. N.Y. Acad. Sci. 2005, 1043,260-266.
Ahmed, N. et al.; Peptide Mapping Identifies Hotspot Site of Modification in Human Serum Albumin by Methylglyoxal Involved in Ligand Binding and Esterase Activity; J. Biol. Chem. 2005, 280, 5724-5732.
Ahmed, N.; Thornalley, P. J.; Advanced glycation endproducts: what is their relevance to diabetic complications?; Diabetes, Obes. Metab. 2007, 9, 233-245.
Alfaro, J. F.; Chemo-Enzymatic Detection of Protein Isoaspartate Using Protein Isoaspartate Methyltransferase and Hydrazine Trapping; Anal. Chem. 2008, 80, 3882-3889.
Alfaro, J. F.; Synthesis of LuxS Inhibitors Targeting Bacterial Cell-Cell Communication; Org. Lett. 2004, 6, 3043-3046.
Awdeh, Z.L., A.R. Williamson, and B.A. Askonas, One cell-one immunoglobulin. Origin of limited heterogeneity of myeloma proteins. Biochem J, 1970. 116(2): p. 241-8.
Bendtzen, K. et al. "Auto-antibodies to IL-1α and TNFα in Normal Individuals and in Infectious and Immunoinflammatory Disorders" *The Physiological and Pathological Effects of Cytokines*, 447-52 (1990).
Biastoff, S.; et al.; Colorimetric Activity Measurement of a Recombinant Putrescine N-Methyltransferase from *Datura stramonium*; Planta Med. 2006, 72, 1136.
Chang, T. & Wu, L., Methylglyoxal, oxidative street, and hypertension, Can. J. Physiol.Pharmacol. 84: 1229-1238 (2006).
Chaplen, F.W.R., et al., Effect of endogenous methylgiyoxal on Chinese hamster ovary celis grown in culture Cytotechnology 1996, vol. 22, Issue 1-3, Abstract and references, 6 pages.
Chaplen, F.W.R., Incidence and potential implications of the toxic metabolite methylglyoxal in cell culture: A review, Cytotechnology 26: 173-183, 1998.

Chaplen, FWR; A dissertation entitled Analysis of Methylglyoxal Metabolism in Mammalian Cell Culture; Univ. of Wisconsin-Madison 1996, 218 pages.
Chelius, D. et al.; Identification and Characterization of Deamidation Sites in the Conserved Regions of Human Immunoglobulin Gamma Antibodies, Anal. Chem. 2005, 77,6004-6011.
Chumsae, C., et al., Comparison of methionine oxidation in thermal stability and chemically stressed samples of a fully human monoclonal antibody. Journal of Chromatography B, 2007. 850(1-2): p. 285-294.
Chumsae, C., Gaza-Bulseco, G., & Liu, H., Identification and localization of unpaired cysteine residues in monoclonal antibodies by fluorescence labeling and mass spectrometry. Anal Chem, 2009.81(15): p. 6449-57.
Chung et al. "Cetuximab-induced anaphylaxis and IgE specific for galactose-a-1,3-galactose" NEJM 358:11, 1109-1117 (2008).
Cordoba, A.J., et al., Non-enzymatic hinge region fragmentation of antibodies in solution. Journal of Chromatography B, 2005. 818(2): p. 115-121.
Dai, S.; An Integrated Proteomic Analysis of Major Isoaspartyl-Containing Proteins in the Urine of Wild Type and Protein Llsoaspartate O-Methyltransferase-Deficient Mice; Anal. Chem. 2013, 85, 2423-2430.
Dionex Application Note 125 (Monitoring Protein Deamidation by Cation-Exchange Chromatography. 2009; pp. 1-7).
Dobo, A. & Kaltashov, I. A.; Detection of Multiple Protein Conformational Ensembles in Solution via Deconvolution of Charge-State Distributions in ESI MS; Anal. Chem. 2001,73, 4763-4773.
Emery, P. "Adalimumab therapy: Clinical findings and implications for integration into clinical guidelines for rheumatoid arthritis." *Drugs of Today*, 41(3): p. 155-163. (2005).
European Medicines Agency (EMA Europe), "2004 Report on Scientific Discussion for the Approval of Humira™ (adalimumab)," Last accessed Nov. 12, 2014 at www.ema.europa.eu/docs/en_GB/document_library/EPAR_Scientific_Discussion/human/000481/WC500050867.pdf; 25 pages.
Fahrner et al., "Industrial purification of pharmaceutical antibodies: development, operation, and validation of chromatography processes" Biotechnology and Genetic Engineering Reviews, 18, 2001, pp. 301-327.
Gagnon, P., "Polishing methods for monoclonal IgG purification" Chapter 17, Taylor & Francis Group, LLC, pp. 491-505, 2007.
Gauthier, M. A.& Klok, H.-A. Arginine-Specific Modification of Proteins with Polyethylene Glycol Biomacromolecules; 2011, 12, 482-493.
Gaza-Bulseco, G., et al., Characterization of the glycosylation state of a recombinant monoclonal antibody using weak cation exchange chromatography and mass spectrometry. J Chromatogr B Analyt Technol Biomed Life Sci, 2008. 862(1-2): p. 155-60. Epub Dec. 8, 2007.
Goswami et al., "Developments and Challenges for mAb-Based Therapeutics," *Antibodies*, 2:452-500, 2013.
Harding et al., "Class switching in human immunoglobulin transgenic mice" (1995) *Ann. NY Acad. Sci.*, 764:536-547.
Harris, R.J., et al., Identification of multiple sources of charge heterogeneity in a recombinant antibody. Journal of Chromatography B: Biomedical Sciences and Applications, 2001. 752(2): p. 233-245.
Hipkiss, A.; Can the beneficial effects of methionine restriction in rats be explained in part by decreased methylglyoxal generation resulting from suppressed carbohydrate metabolism?; Biogerontology 2012, 13, 633-636.
Huang, L., et al., In Vivo Deamidation Characterization of Monoclonal Antibody by LC/MS/MS. Analytical Chemistry, 2005. 77(5): p. 1432-1439.
International Preliminary Report on Patentability for Application No. PCT/US2013/031365, dated Mar. 3, 2015, 9 pages.
International Search Report for Application No. PCT/US2014/026606, Dated Dec. 8, 2014, 8 pages.
International Search Report for Application No. PCT/US2014/026636, Dated Jul. 29, 2014, 5 pages.

(56) References Cited

OTHER PUBLICATIONS

Jack, M.; Wright, D.; The Role of Advanced Glycation Endproducts and Glyoxalase I in Diabetic Peripheral Sensory Neuropathy; Transl. Res. 2012, 159, 355-365.
Jakubowski, H., Protein N-homocysteinylation: implications for atherosclerosis. Biomedicine; Pharmacotherapy, 2001. 55(8): p. 443-447.
Jefferis, R., Glycosylation of Recombinant Antibody Therapeutics. Biotechnology Progress, 2005.21(1): p. 11-16.
Johnson, K.A., et al., Cation exchange HPLC and mass spectrometry reveal C-terminal amidation of an IgG1 heavy chain. Analytical Biochemistry, 2007. 360(1): p. 75-83.
Kanda, et al.: "Comparison of biological activity among nonfucosylated therapeutic IgG1 antibodies with three different N-linked Fc oligosaccharides: the high-mannose, hybrid, and complex types", Glycobiology, Oxford University Press, US, vol. 17, No. 1, Sep. 2006, pp. 104-118.
Kazuaki F et al "Enhancment of productivity of recombinant a-amidating enzyme by low temperature culture" Cytotechnology 31:85-94, 1999.
Kingkeohoi, S., Analysis of methylglyoxal metabolism in CHO celis grown in culture, Cytotechnology (2005) 48:1-13.
Leusch, "Failure to demonstrate TNFα-specific autoantibodies in human sera by ELISA and Western blot" (1991) *J. Immunol. Methods*, 139:145-47.
Liu et al. "Recovery and purificaiton process development for monoclonal antibody production" MABS, 2(5), pp. 480-499 (2010).
Liu, H., Assessment of antibody fragmentation by reversed-phase liquid chromatography and mass spectrometry. J Chromatogr B Analyt Technol Biomed Life Sci, 2008. 876(1): p. 13-23. Epub Oct 15, 2008.
Liu, H., et al., Heterogeneity of monoclonal antibodies. Journal of Pharmaceutical Sciences, 2008. 97(7): p. 2426-2447.
Liu, M, et al.; Discovery of Undefined Protein Cross-Linking Chemistry: A Comprehensive Methodology Utilizing 18O—Labeling and Mass Spectrometry; Anal. Chem. 2013, 5900-5908.
Liu, M.et al.; Protein Isoaspartate Methyltransferase-Mediated 18O-Labeling of Isoaspartic Acid for Mass Spectrometry Analysis; Anal. Chem. 2011, 84, 1056-1062.
Lo, T.W. et al., Binding and modification of proteins by methylglyoxal under physiological conditions. A kinetic and mechanistic study with N alpha-acetylarginine, N alpha-acetyilysine, and N alpha-acetyllysine, and bovine serum albumin, Dec. 23, 1994, The Journal of Biological Chemistry, 269, 32299-32305.
Manning, M., et al., *Stability of Protein Pharmaceuticals: An Update*. Pharmaceutical Research, 2010.27(4): p. 544-575.
Matthews, R. G.; et al.; Cobalamin-Dependent and Cobalamin-Independent Methionine Synthases: Are There Two Solutions to the Same Chemical Problem?; Helv. Chim. Acta 2003, 86, 3939-3954.
Mizuochi, T., et al., Structural and numerical variations of the carbohydrate moiety of immunoglobulin G. J Immunol, 1982. 129(5): p. 2016-20.
Moorhouse, K.G., et al., Validation of an HPLC method for the analysis of the charge heterogeneity of the recombinant monoclonal antibody IDEC-C2B8 after papain digestion. Journal of Pharmaceutical and Biomedical Analysis, 1997. 16(4): p. 593-603.
Mostafa, A et al.; Plasma protein advanced glycation end products, carboxymethyl cysteine, and carboxyethyl cysteine, are elevated and related to nephropathy in patients with diabetes Mol. Cell. Biochem. 2007, 302, 35-42.
Ni, W.; Analysis of Isoaspartic Acid by Selective Proteolysis with Asp-N and Electron Transfer Dissociation Mass Spectrometry; Anal. Chem. 2010, 82,7485-7491.
Ouellette, D.; Studies in serum support rapid formation of disulfide bond between unpaired cysteine residues in the VH domain of an immunoglobulin G1 molecule; Anal. Biochem. 2010, 397, 37.
Oya, T. et al. Methylglyoxal Modification of Protein: Chemical and Immunochemical Characterization of Methylglyoxal-Arginine Adducts. J. Bioi Chem. Jun. 25, 1999; vol. 274, No. 26, pp. 18492-19502.

Pacis, et al.: "Effects of cell culture conditions on antibody N-linked glycosylation—what affect high mannose 5 glycoform", Biotechnology and Bioengineering vol. 108, No. 10 Oct. 2011, pp. 2348-2358.
Paoli, T. et al., A Study of D-Lactate and Extracellular Methylglyoxal Production in Lactate ReUtilizing CHO Cultures, Biotechnology and Bioengineering, vol. 107, No. 1, Sep. 1, 2010, pp. 182-189.
Parekh, R.B., et al., Association of rheumatoid arthritis and primary osteoarthritis with changes in the glycosylation pattern of total serum IgG. Nature, 1985. 316(6027): p. 452-7.
PCT/US2013/069702 International Search Report & Written Opinion mailed Jan. 31, 2014, 13 pages.
Perkins, M.; et. Al. Determination of the Origin of Charge Heterogeneity in a Murine Monoclonal Antibody; M. Pharm. Res. 2000, 17, 1110-1117.
Quan, C., et al., A study in glycation of a therapeutic recombinant humanized monoclonal antibody: Where it is, how it got there, and how it affects charge-based behavior. Analytical Biochemistry, 2008. 373(2): p. 179-191.
Rabbani, N.; Thornalley, P. J.; Glyoxalase in diabetes, obesity and related disorders; Semin. Cell Dev. Biol. 2011, 22, 309-317.
Ren, D., et al., Reversed-phase liquid chromatography-mass spectrometry of site-specific chemical modifications in intact immunoglobulin molecules and their fragments. Journal of Chromatography A, 2008. 1179(2): p. 198-204.
Roy, B.M., et al., Toxic concentrations of exogenously supplied methy!glyoxal in hybridoma cell culture, Cytotechnology (2004) 46:97-107.
Saxena, R. K. et al.; Microbial production and applications of 1 ,2-propanediol; Indian J. Microbiol. 2010,50,2-11.
Shubert et al. "Comparison of ceramic hydroxy- and fluoroapatite versus Protein A/G-based resins in the isiolation of a recombinant human antibody from cell culture supernatant" J. Chromatography A, 114 (2007) 106-113.
The Kennedy Institute of Rheumatology, 1995 Annual Scientific Report, "Anti-TNF trials and studies of mechanisms of action".
United States Food and Drug Administration (FDA) Biological Licensing Application File No. 125057 (Adalimumab) (Dec. 31, 2002) (Last Accessed Mar. 4, 2015 at <http://www.fda.gov/Drugs/DevelopmentApprovalProcess/HowDrugsareDevelopedandApproved/ApprovalApplications/TherapeuticBiologicApplications/ucm080610.htm>), 1 page.
Van Herreweghe, et al.; Tumor necrosis factor-induced modulation of glyoxalase I activities through phosphorylation by PKA results in cell death and is accompanied by the formation of a specific methylglyoxal-derived AGE; Proc. Natl. Acad. Sci. 2002, 99, 949-954.
Vasilli, P. et al., The Pathophysiology of Tumor Necrosis Factors, Annu. Rev. Immunol. 10:411-452 (1992).
Vlasak, J. & Ionescu, R., *Heterogeneity of Monoclonal Antibodies Revealed by Charge-Sensitive Methods*. Current Pharmaceutical Biotechnology, 2008. 9(6): p. 468-481.
Walsh, et al.: "Post-translational modifications in the context of therapeutic proteins", Nature Biotechnology, vol. 24, No. 10, Oct. 2006, pp. 1241-1252.
Wang, Z.; et al. Desulfurization of Cysteine-Containing Peptides Resulting from Sample Preparation for Protein Characterization by MS; Rapid Commun. Mass Spectrom. 2010, 24, 267-275.
Watt, S.; et al.; Effect of Protein Stabilization on Charge State Distribution in Positive- and Negative-Ion Electrospray Ionization Mass Spectra; J. Am. Soc. Mass. Spectrom. 2007, 18, 1605-1611.
Williams, A. et al., Ion-Exchange Chromatography, Oct. 1998, Supplement 44, pp. 10-10-1-10-10-30.
Xiang, T., Chumsae, C. & Liu, H., Localization and Quantitation of Free Sulfhydryl in Recombinant Monoclonal Antibodies by Differential Labeling with 12C and 13C Iodoacetic Acid and LC-MS Analysis. Analytical Chemistry, 2009. 81(19): p. 8101-8108.
Yuk, I.H. et al., Controlling Glycation of Recombinant Antibody in Fed Batch Cell Cultures, Nov. 2011, Biotechnology and Bioengineering, vol. 108, No. 11 pp. 2600-2610.

(56) References Cited

OTHER PUBLICATIONS

Zang, T.; et al.; Chemical Methods for the Detection of Protein N-Homocysteinylation via Selective Reactions with Aldehydes; Anal. Chem. 2009, 81, 9065-9071.

Zhang, B., et al., Unveiling a Glycation Hot Spot in a Recombinant Humanized Monoclonal Antibody. Analytical Chemistry, 2008. 80(7): p. 2379-2390.

Zhang, T.; Identification and Characterization of Buried Unpaired Cysteines in a Recombinant Monoclonal IgG1 Antibody; Anal. Chem. 2012, 84, 7112-7123.

Zhang, W. and Czupryn, M.J., Free Sulfhydryl in Recombinant Monoclonal Antibodies. Biotechnology Progress, 2002. 18(3): p. 509-513.

Zhao, G.; Chemical Synthesis of S-Ribosyl-L-homocysteine and Activity Assay as a LuxS Substrate; Bioorg. Med. Chem. Lett. 2003,13,3897-3900.

Zhou, Z. et al.; An Antibody-Catalyzed Allylic Sulfoxide-Sulfenate Rearrangement; J. Org. Chem. 1999,64,8334-8341.

Zhou, Z. S. et al. An Antibody-Catalyzed Selenoxide Elimination; J. Am. Chem. Soc. 1997, 119, 3623-3624.

\* cited by examiner

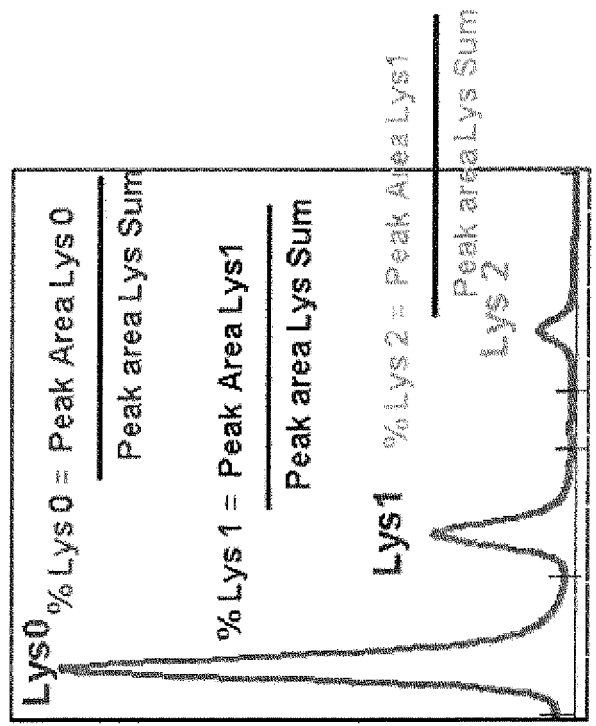
Figure 1) Representation of the lysine variants in a sample WCX-10 chromatogram and quantification scheme of each of the variants

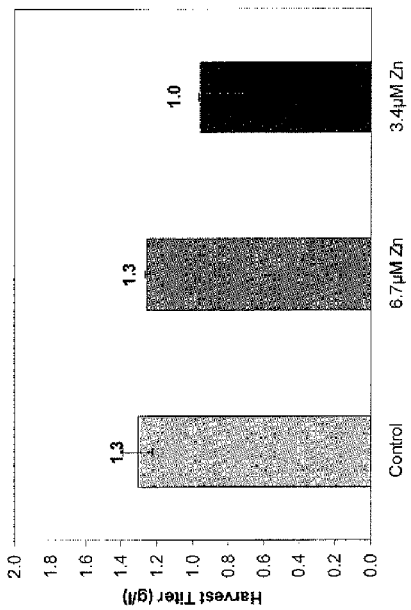

Figure 2) Effect of zinc modulation in adalimumab producing cell line 1, media 1 on viable cell density (n=2)

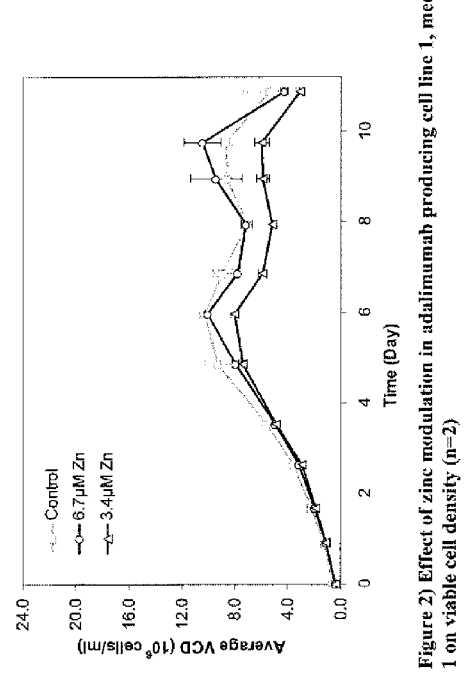

Figure 4) Effect of zinc modulation in adalimumab producing cell line 1, media 1 on harvest titer (n=2)

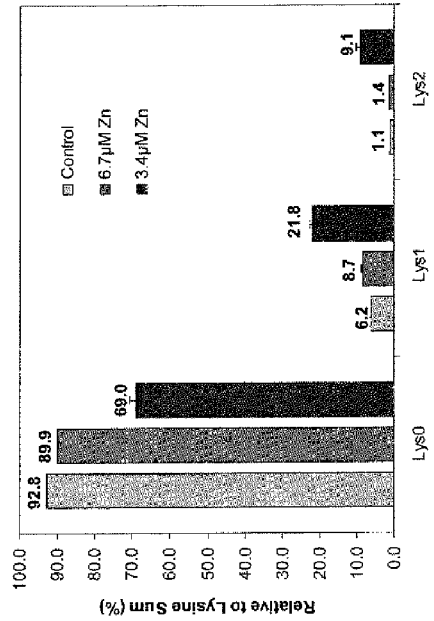

Figure 3) Effect of zinc modulation in adalimumab producing cell line 1, media 1 on viability (n=2)

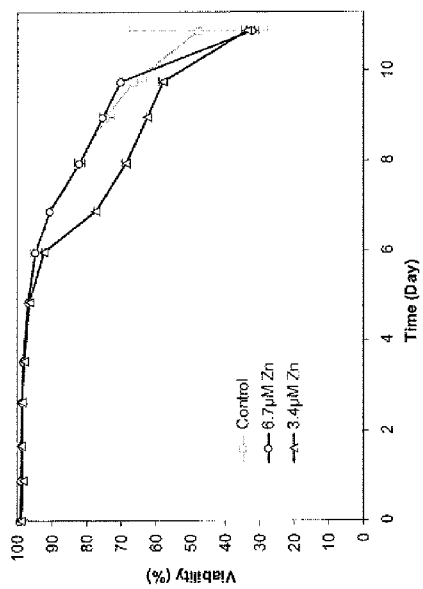

Figure 5) Effect of zinc modulation in adalimumab producing cell line 1, media 1 on day 10 WCX 10 profile relative lysine distribution (n=2)

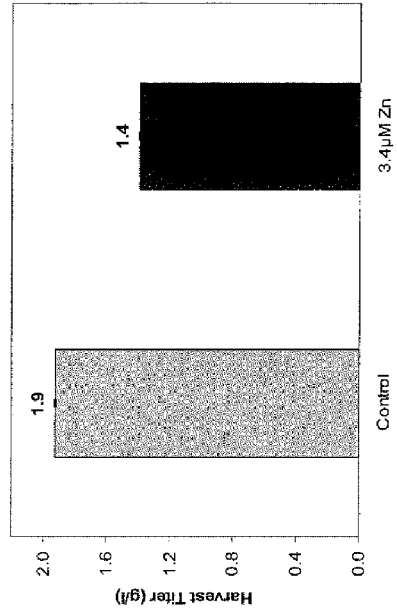

Figure 6) Effect of zinc modulation in adalimumab producing cell line 1, media 1 on viable cell density (n=2)

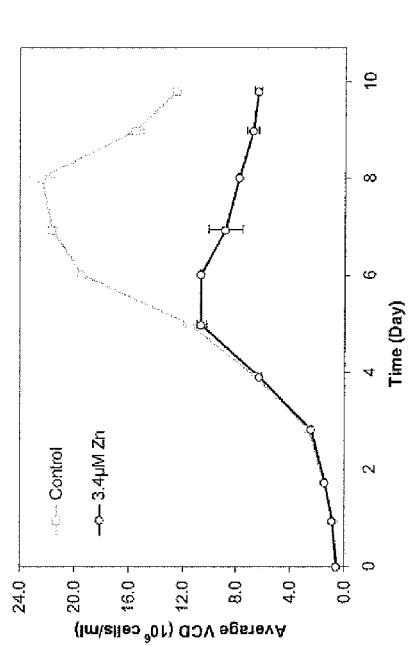

Figure 7) Effect of zinc modulation in adalimumab producing cell line 1, media 1 on viability (n=2)

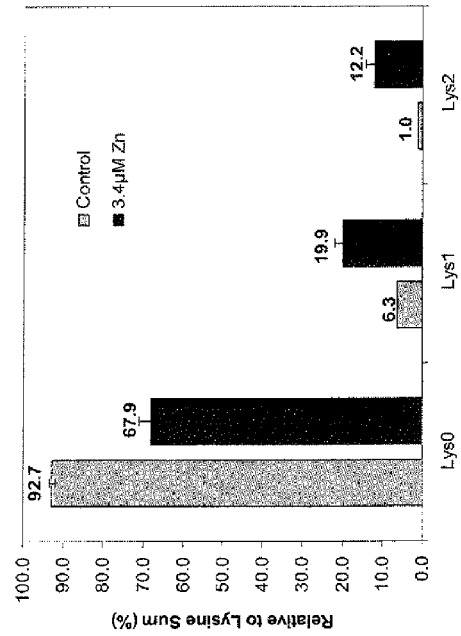

Figure 8) Effect of zinc modulation in adalimumab producing cell line 1, media 1 on harvest titer (n=2)

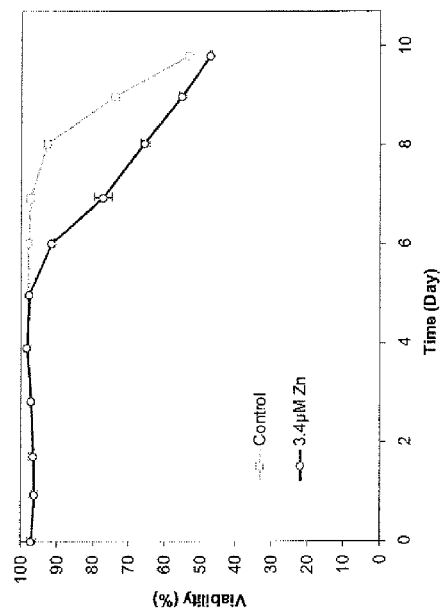

Figure 9) Effect of zinc modulation in adalimumab producing cell line 1, media 1 on day 10 WCX 10 profile relative lysine distribution (n=2)

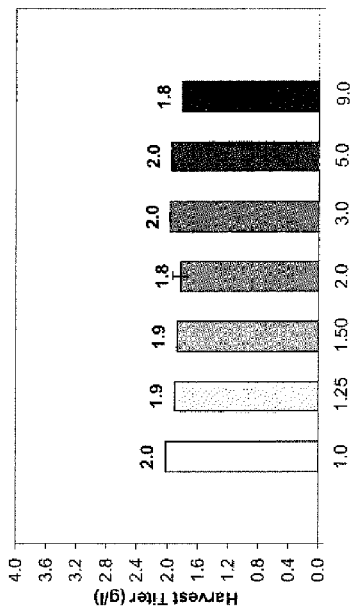

Figure 10) Effect of total arginine concentration in adalimumab producing cell line 2, media 1 on viable cell density (n=2)

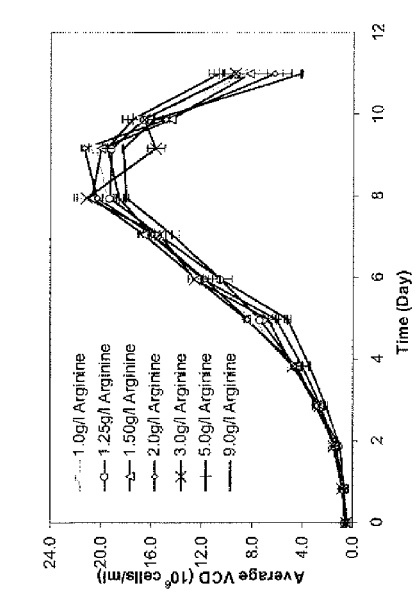

Figure 11) Effect of total arginine concentration in adalimumab producing cell line 2, media 1 on viability (n=2)

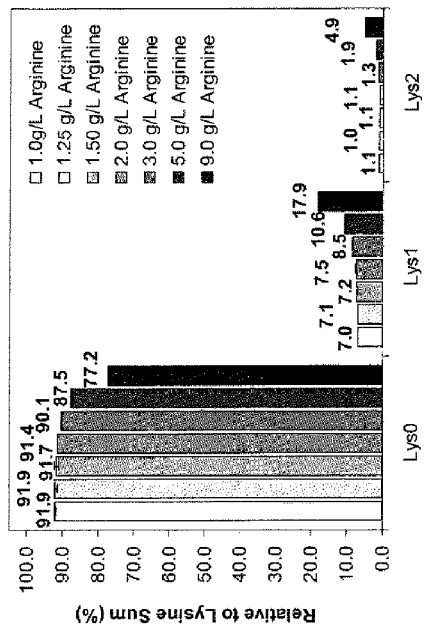

Figure 12) Effect of total arginine concentration in adalimumab producing cell line 2, media 1 on harvest titer (n=2)

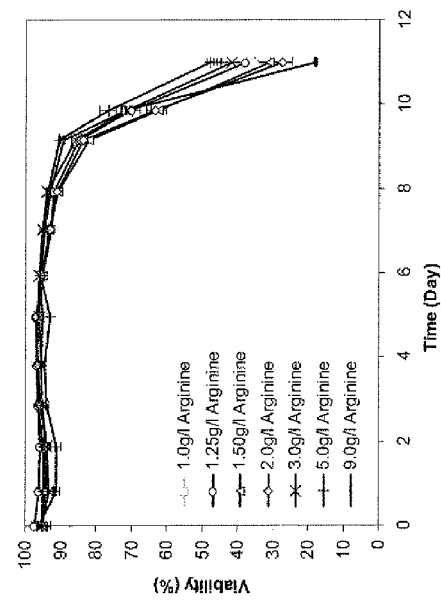

Figure 13) Effect of total arginine concentration in adalimumab producing cell line 2, media 1 on day 10 on WCX 10 profile relative lysine distribution (n=2)

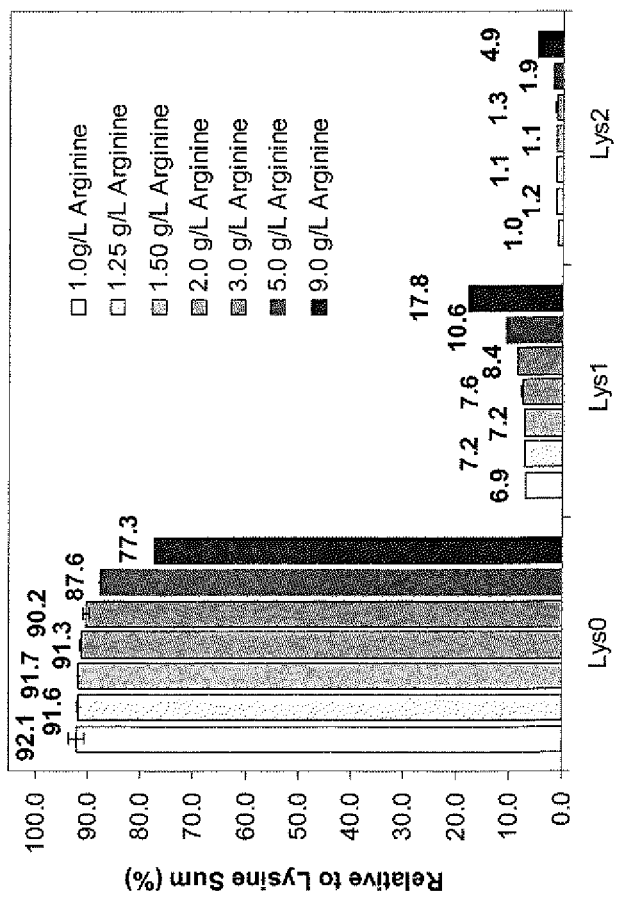
Figure 14) Effect of total arginine concentration in adalimumab producing cell line 2, media 1 on day 12 on WCX 10 profile relative lysine distribution (n=2)

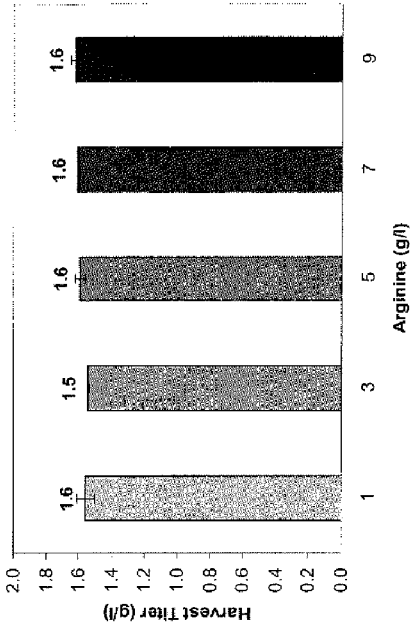

Figure 15) Effect of total arginine concentration in adalimumab producing cell line 3, media 1 on viable cell density (n=2)

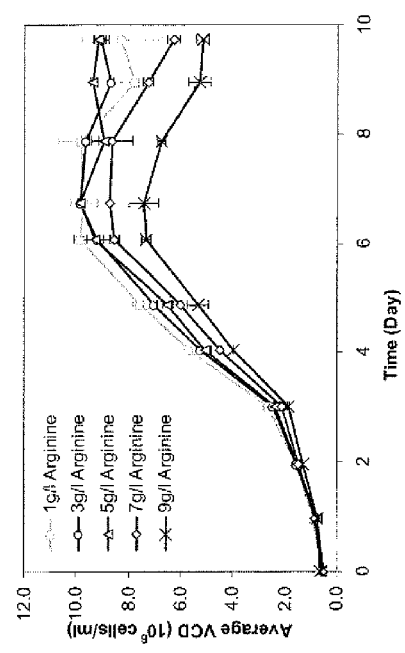

Figure 16) Effect of total arginine concentration in adalimumab producing cell line 3, media 1 on viability (n=2)

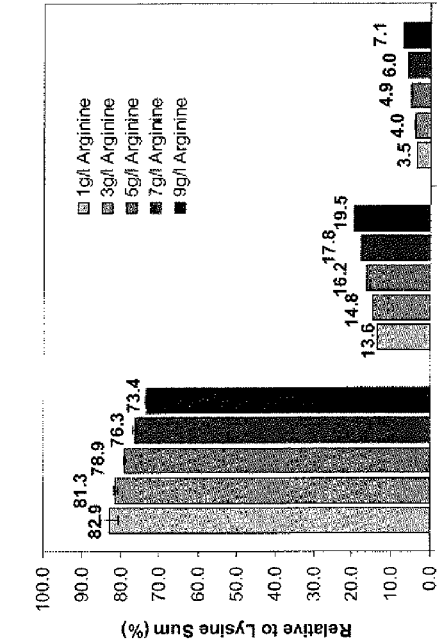

Figure 17) Effect of total arginine concentration in adalimumab producing cell line 3, media 1 on harvest titer (n=2)

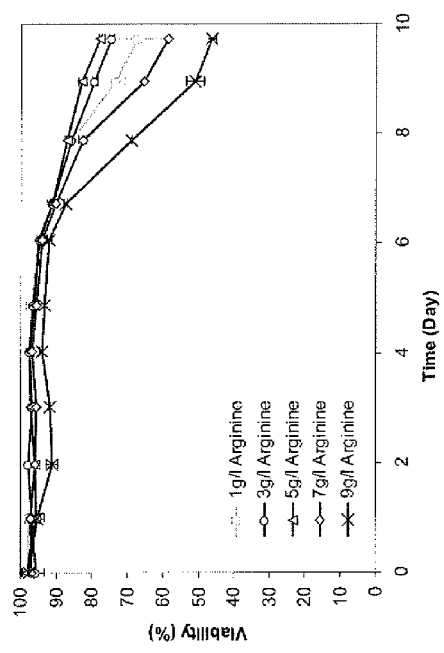

Figure 18) Effect of total arginine concentration in adalimumab producing cell line 3, media 1 on WCX 10 profile relative lysine distribution (n=2)

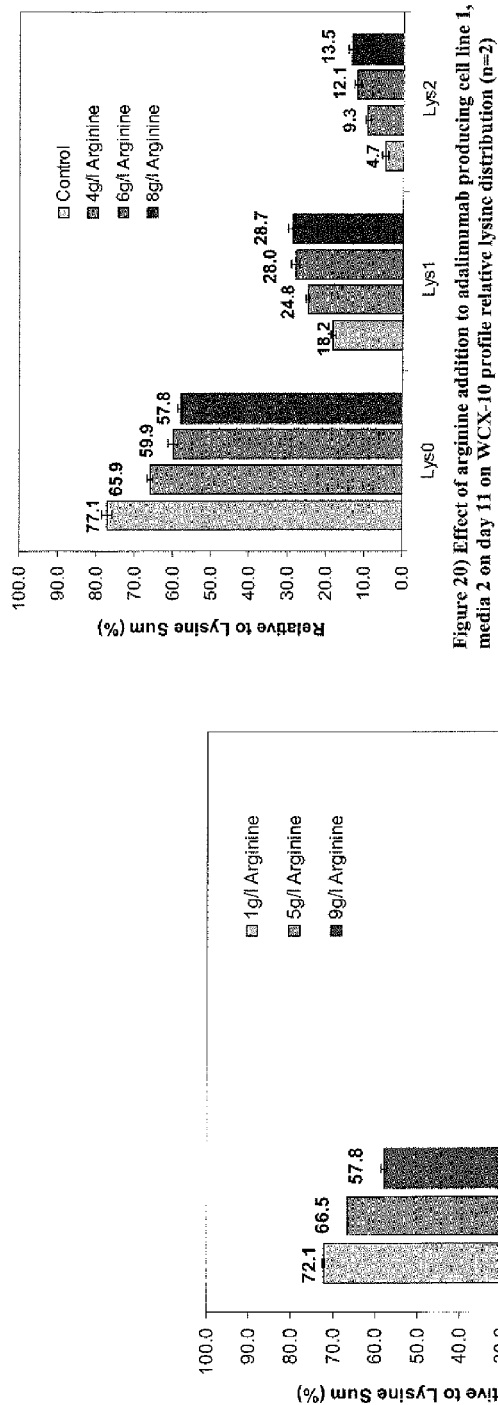

Figure 20) Effect of arginine addition to adalimumab producing cell line 1, media 2 on day 11 on WCX-10 profile relative lysine distribution (n=2)

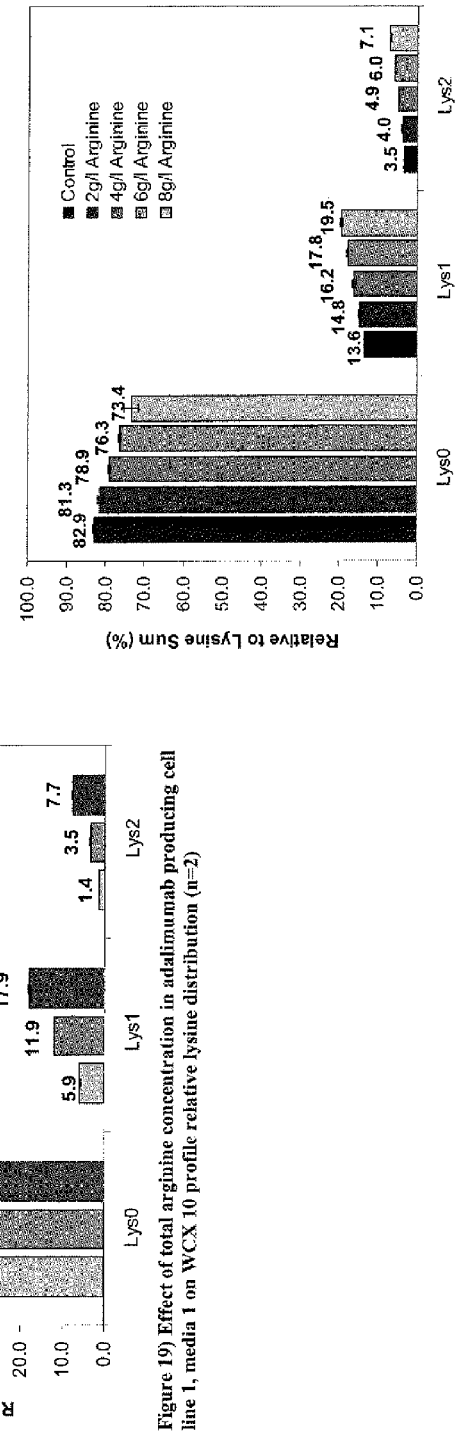

Figure 21) Effect of arginine addition to adalimumab producing cell line 2, media 3 on WCX-10 profile relative lysine distribution (n=2)

Figure 19) Effect of total arginine concentration in adalimumab producing cell line 1, media 1 on WCX 10 profile relative lysine distribution (n=2)

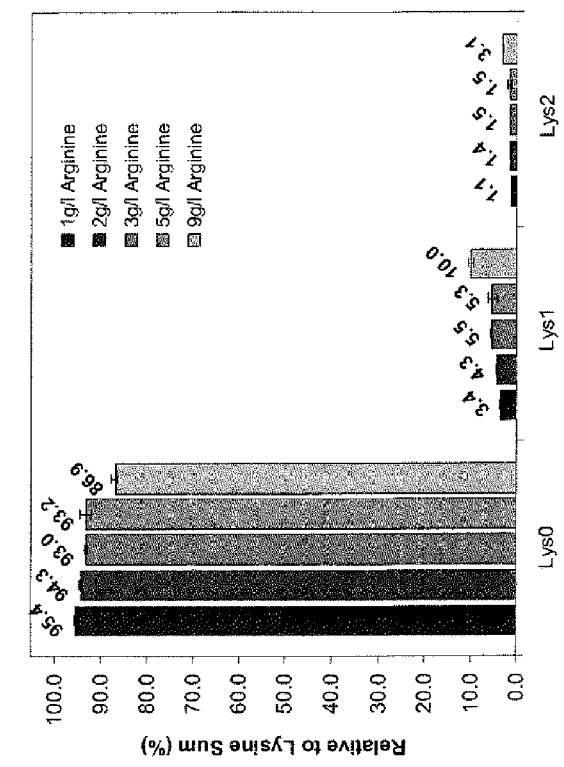
Figure 23) Effect of total arginine concentration in mAB2 producing cell line on WCX-10 profile relative lysine distribution (n=2)
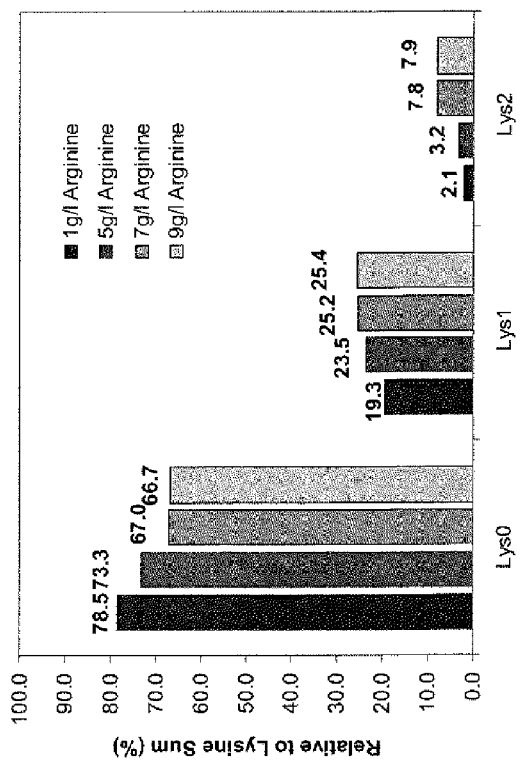
Figure 22) Effect of total arginine concentration in mAB1 producing cell line on WCX-10 profile relative lysine distribution (nn=1)

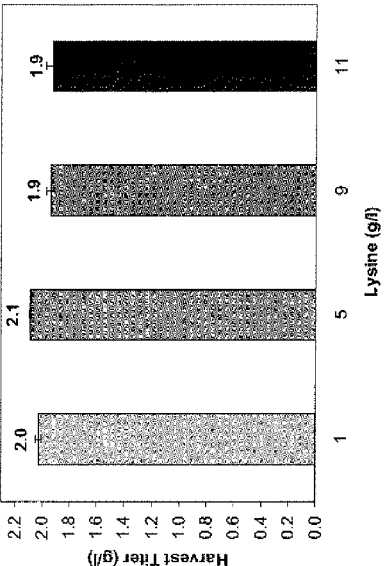

Figure 24) Effect total lysine concentration in adalimumab producing cell line 2, media 1 on viable cell density (n=2)

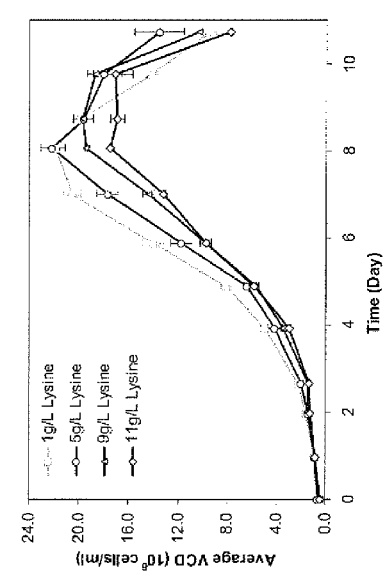

Figure 25) Effect of total lysine concentration in adalimumab producing cell line 2, media 1 on viability (n=2)

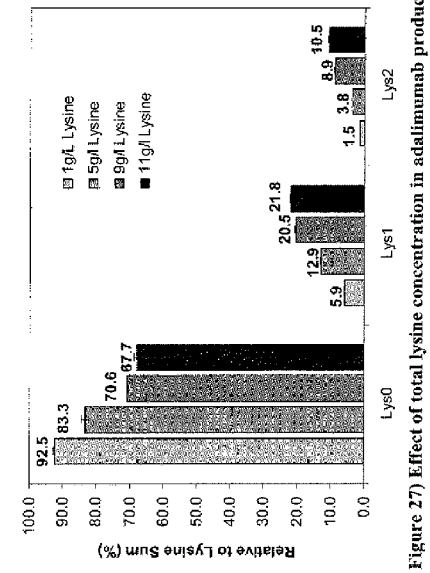

Figure 26) Effect of total lysine concentration in adalimumab producing cell line 2, media 1 on harvest titer (n=2)

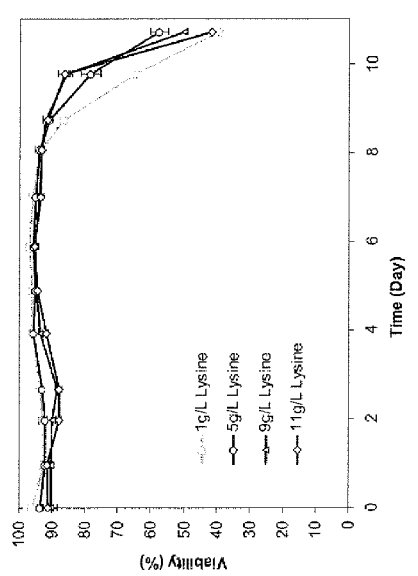

Figure 27) Effect of total lysine concentration in adalimumab producing cell line 2, media 1 on WCX 10 profile relative lysine distribution (n=2)

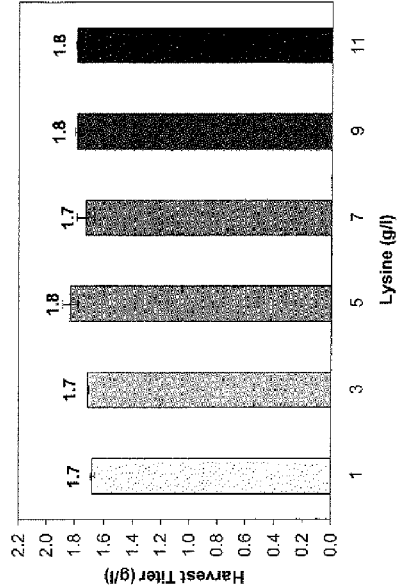

Figure 28) Effect of total lysine concentration in adalimumab producing cell line 3, media 1 on viable cell density (n=2)

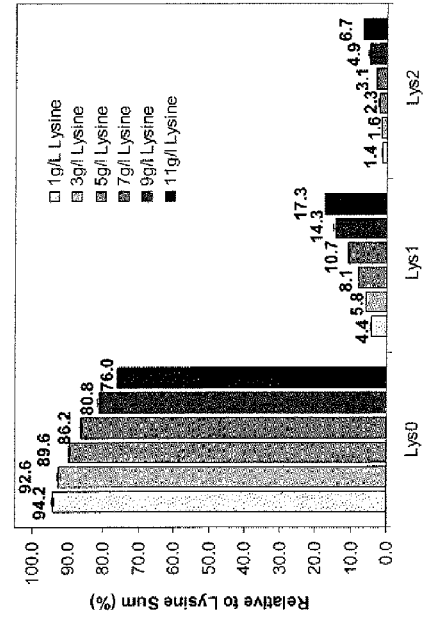

Figure 30) Effect of total lysine concentration in adalimumab producing cell line 3, media 1 on harvest titer (n=2)

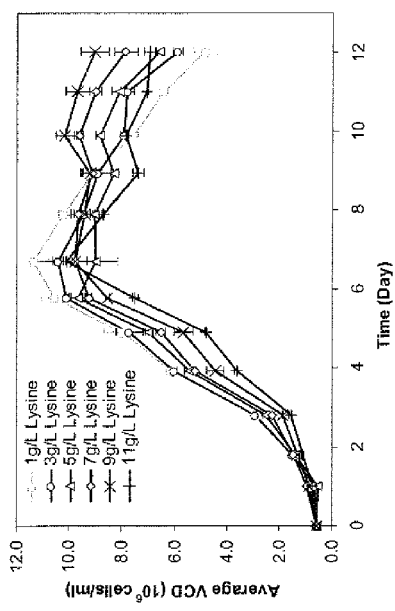

Figure 29) Effect of total lysine concentration in adalimumab producing cell line 3, media 1 on viability (n=2)

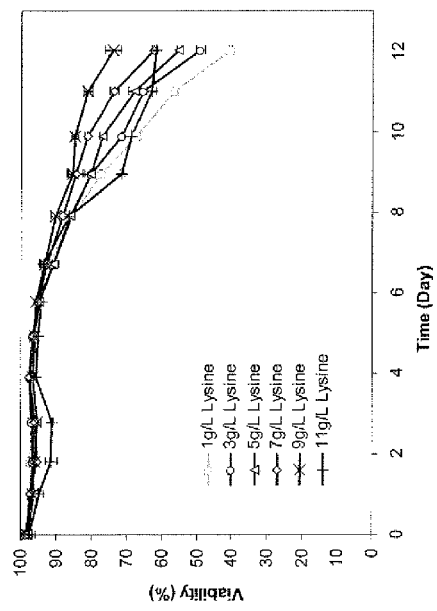

Figure 31) Effect of total lysine concentration in adalimumab producing cell line 3, media 1 on WCX 10 profile relative lysine distribution (n=2)

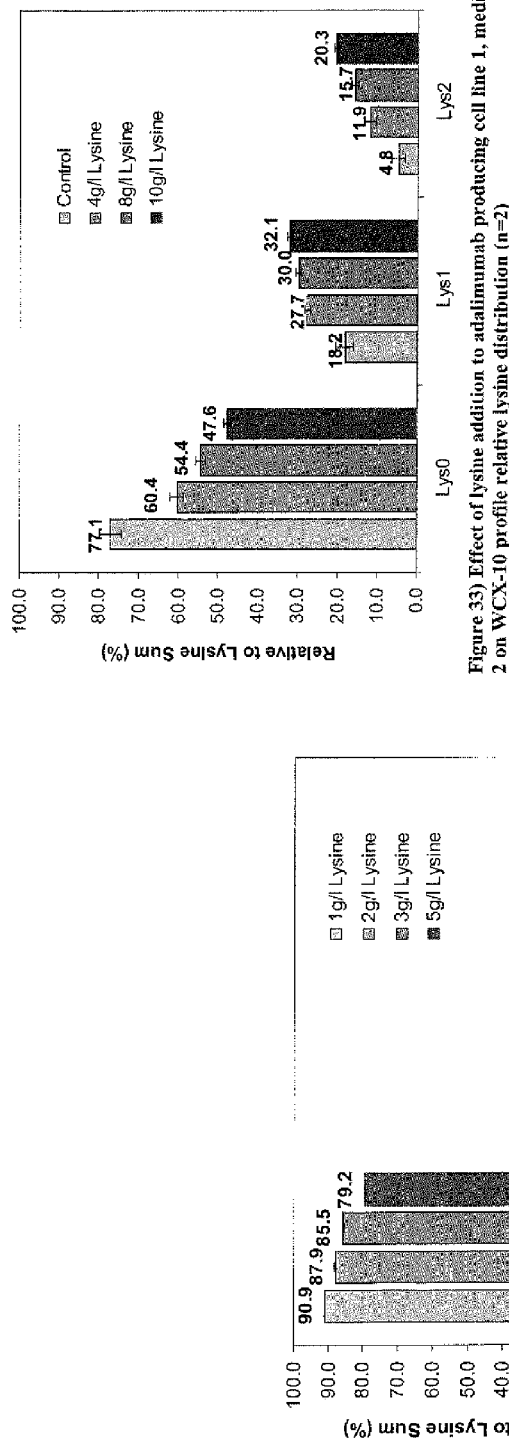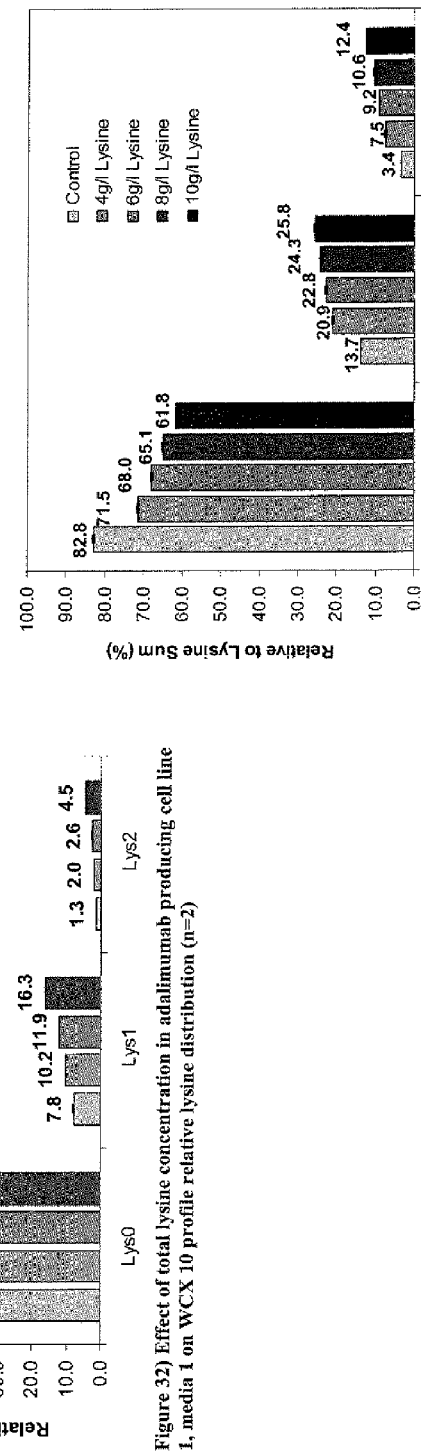

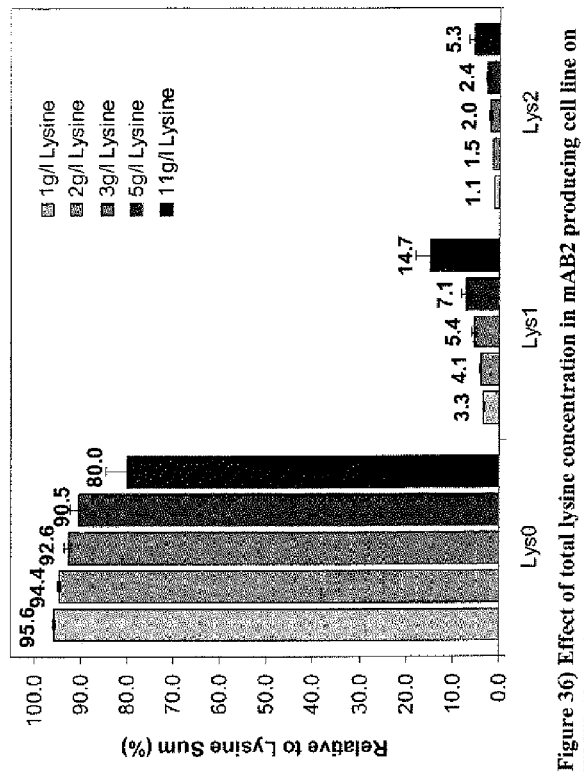
Figure 36) Effect of total lysine concentration in mAB2 producing cell line on WCX-10 profile relative lysine distribution (n=2)
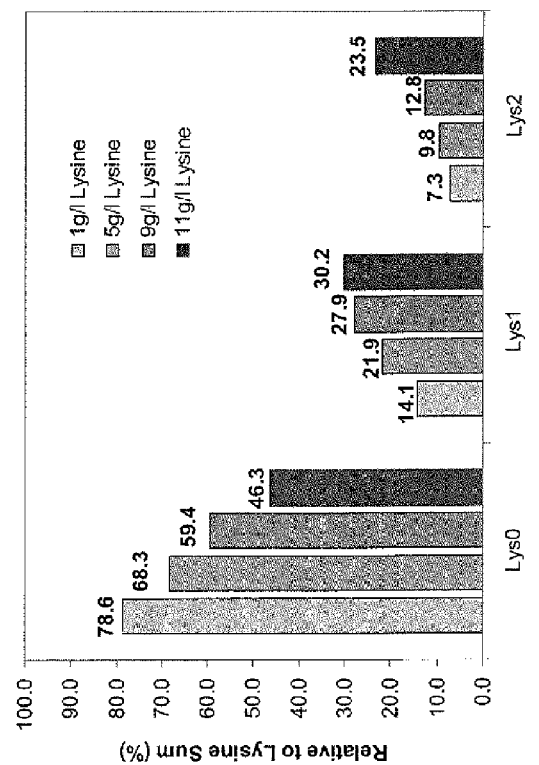
Figure 35) Effect of total lysine concentration in mAB1 producing cell line on WCX-10 profile relative lysine distribution (n=1)

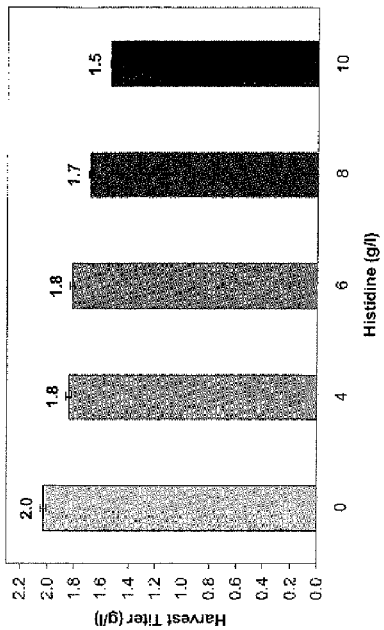

Figure 37) Effect of total histidine concentration in adalimumab producing cell line 2, media 1 on viable cell density (n=2)

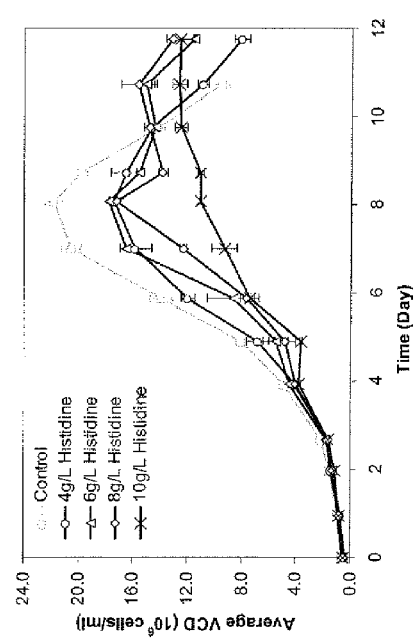

Figure 38) Effect of total histidine concentration in adalimumab producing cell line 2, media 1 on viability (n=2)

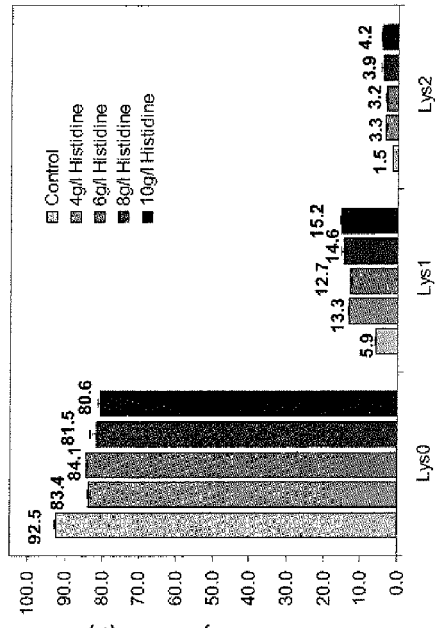

Figure 39) Effect of total histidine concentration in adalimumab producing cell line 2, media 1 on harvest titer (n=2)

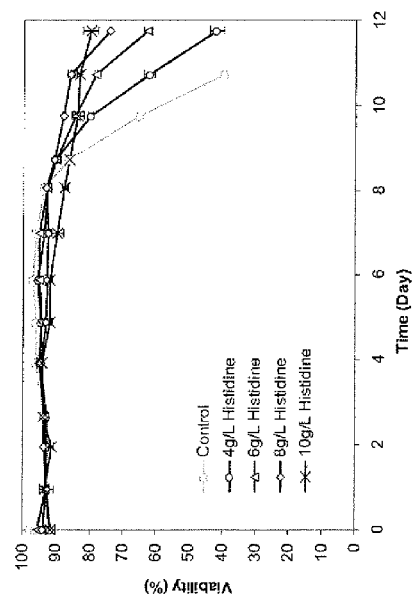

Figure 40) Effect of total histidine concentration in adalimumab producing cell line 2, media 1 on WCX 10 profile relative lysine distribution (n=2)

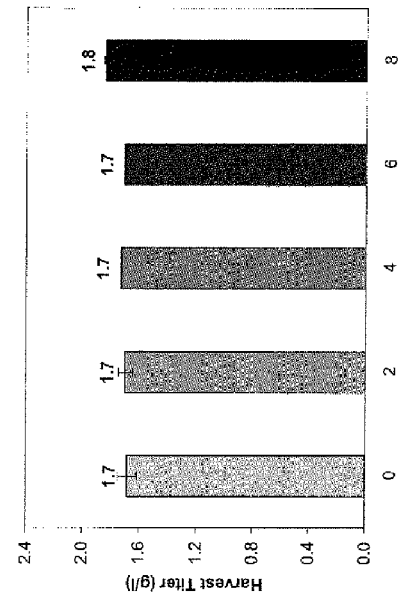

Figure 41) Effect of total histidine concentration in adalimumab producing cell line 3, media 1 on viable cell density (n=2)

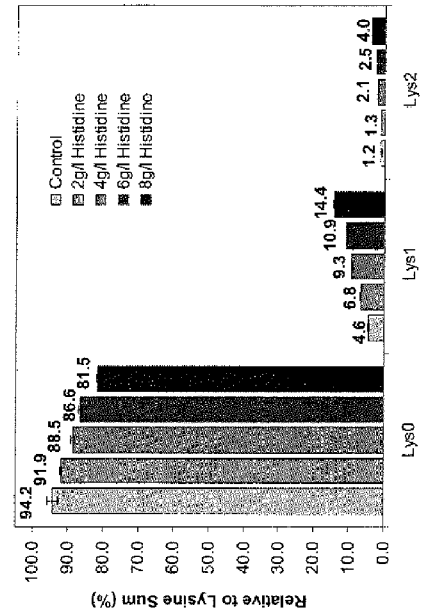

Figure 43) Effect of total histidine concentration in adalimumab producing cell line 3, media 1 on harvest titer (n=2)

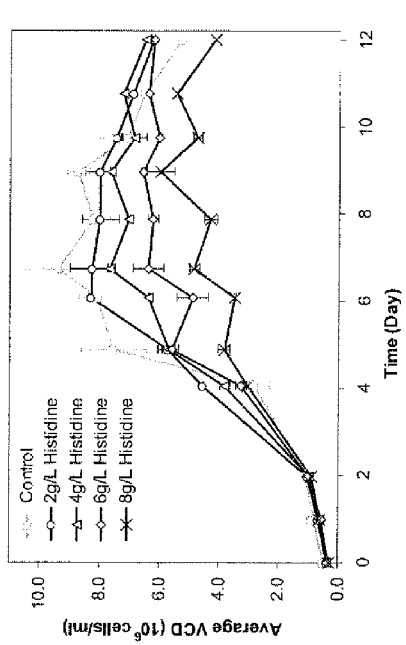

Figure 42) Effect of total histidine concentration in adalimumab producing cell line 3, media 1 on viability (n=2)

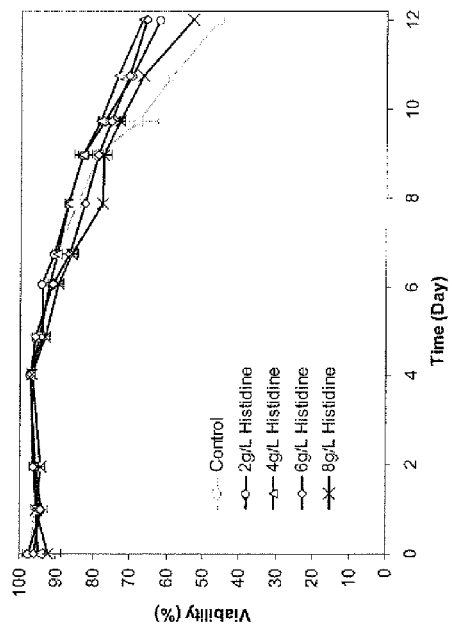

Figure 44) Effect of total histidine concentration in adalimumab producing cell line 3, media 1 on WCX 10 profile relative lysine distribution (n=2)

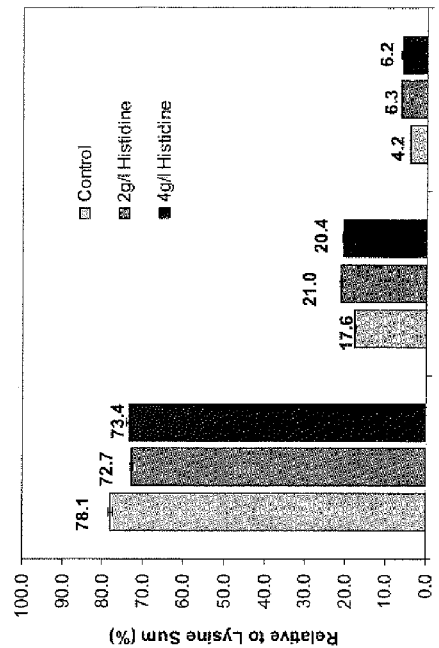

Figure 45) Effect total histidine concentration in adalimumab producing cell line 1, media 1 on WCX 10 profile relative lysine distribution (n=2)

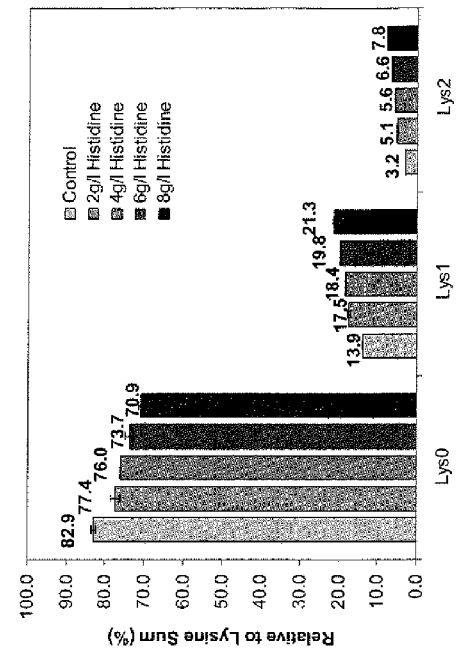

Figure 46) Effect of histidine addition to adalimumab producing cell line 1, media 2 on WCX-10 profile relative lysine distribution (n=2)

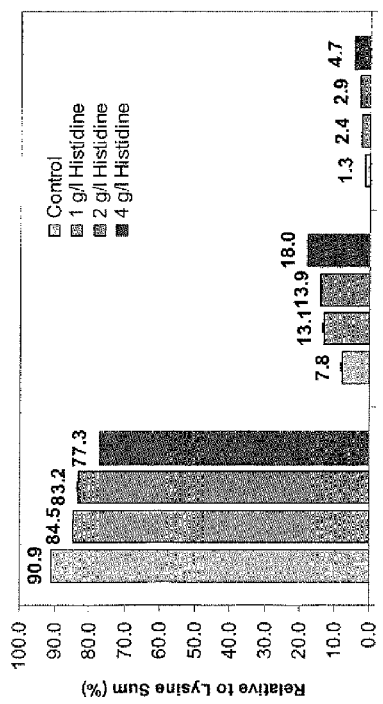

Figure 47) Effect of histidine addition to adalimumab producing cell line 2, media 3 on WCX-10 profile relative lysine distribution (n=2)

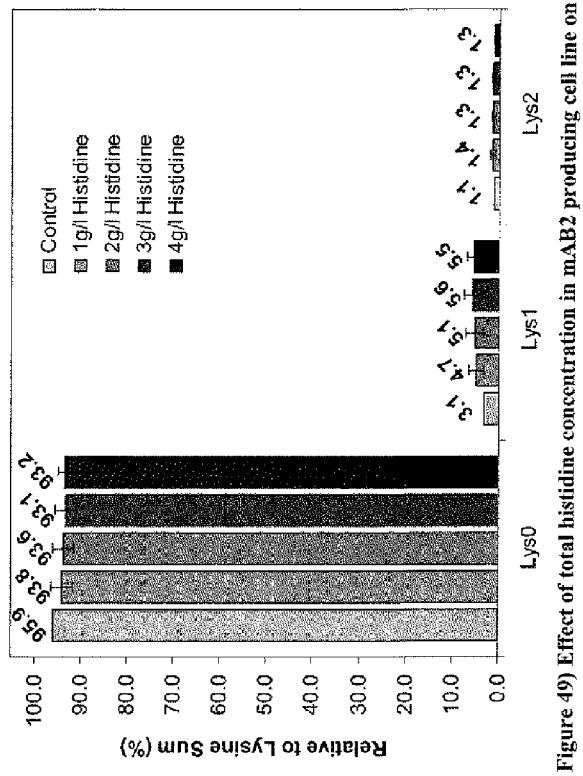
Figure 49) Effect of total histidine concentration in mAB2 producing cell line on WCX-10 profile relative lysine distribution (n=2)
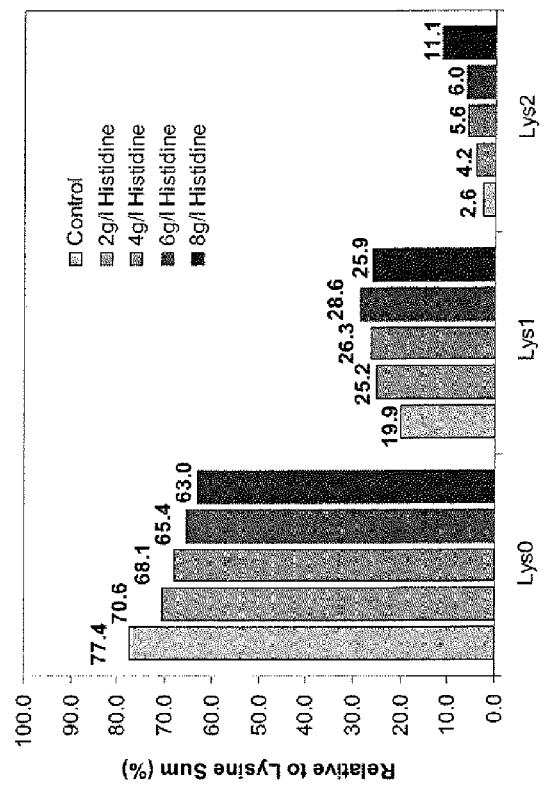
Figure 48) Effect of total histidine concentration in mAB1 producing cell line on WCX-10 profile relative lysine distribution (n=1)

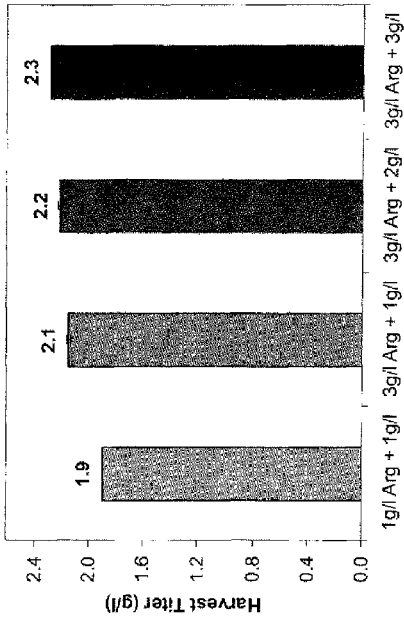

Figure 50) Effect of increase in multiple amino acids to adalimumab producing cell line 1, media 1 on viable cell density (n=2)

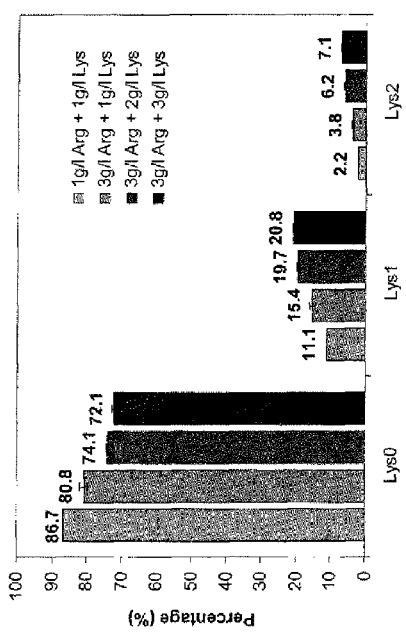

Figure 52) Effect of increase in multiple amino acids to adalimumab producing cell line 1, media 1 on harvest titer

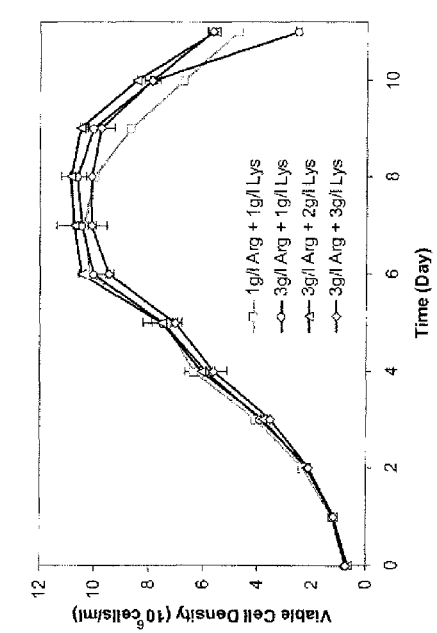

Figure 51) Effect of increase in multiple amino acids to adalimumab producing cell line 1, media 1 on viability

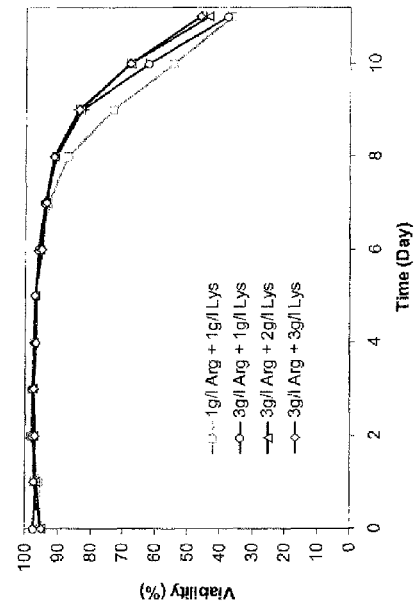

Figure 53) Effect of increase in multiple amino acids to adalimumab producing cell line 1, media 1 on WCX 10 profile relative lysine distribution

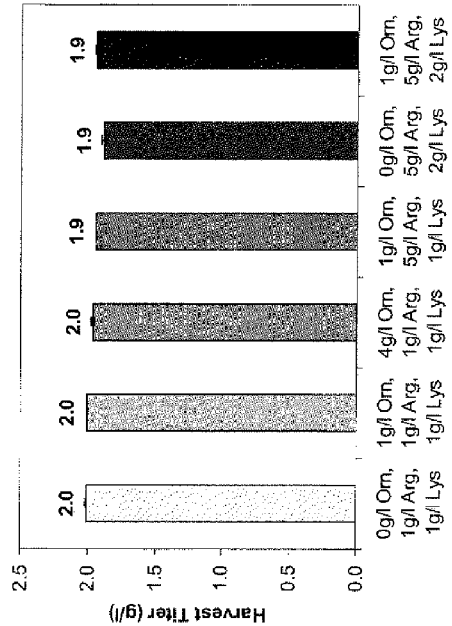

Figure 54) Effect of increase in multiple amino acids to adalimumab producing cell line 3, media 1 on viable cell density (n=2)

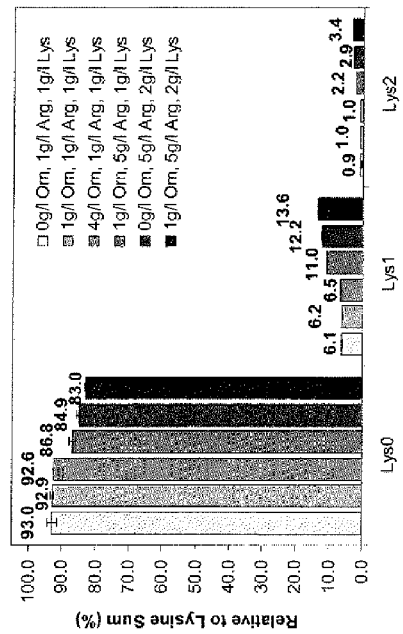

Figure 56) Effect of increase in multiple amino acids to adalimumab producing cell line 3, media 1 on harvest titer

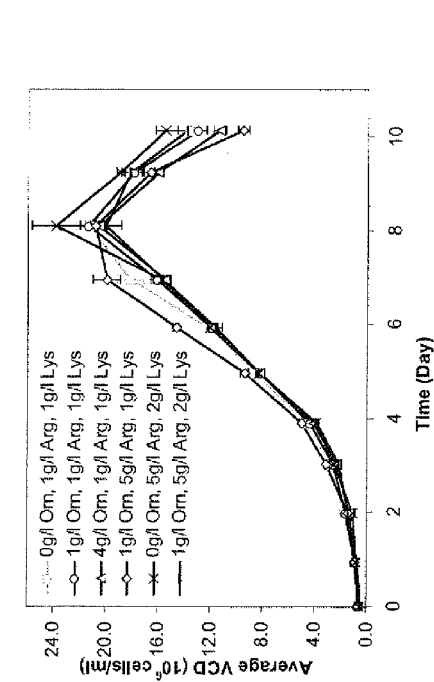

Figure 55) Effect of increase in multiple amino acids to adalimumab producing cell line 3, media 1 on viability

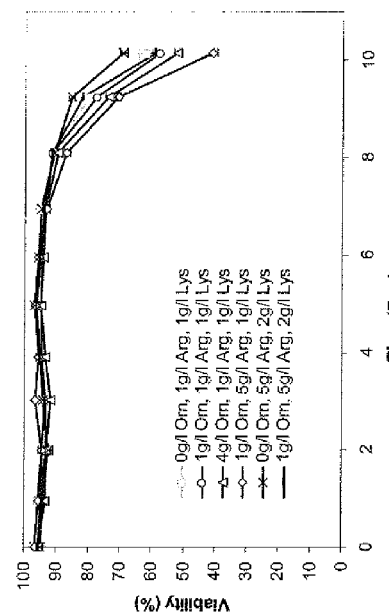

Figure 57) Effect of increase in multiple amino acids to adalimumab producing cell line 3, media 1 on WCX 10 profile relative lysine distribution

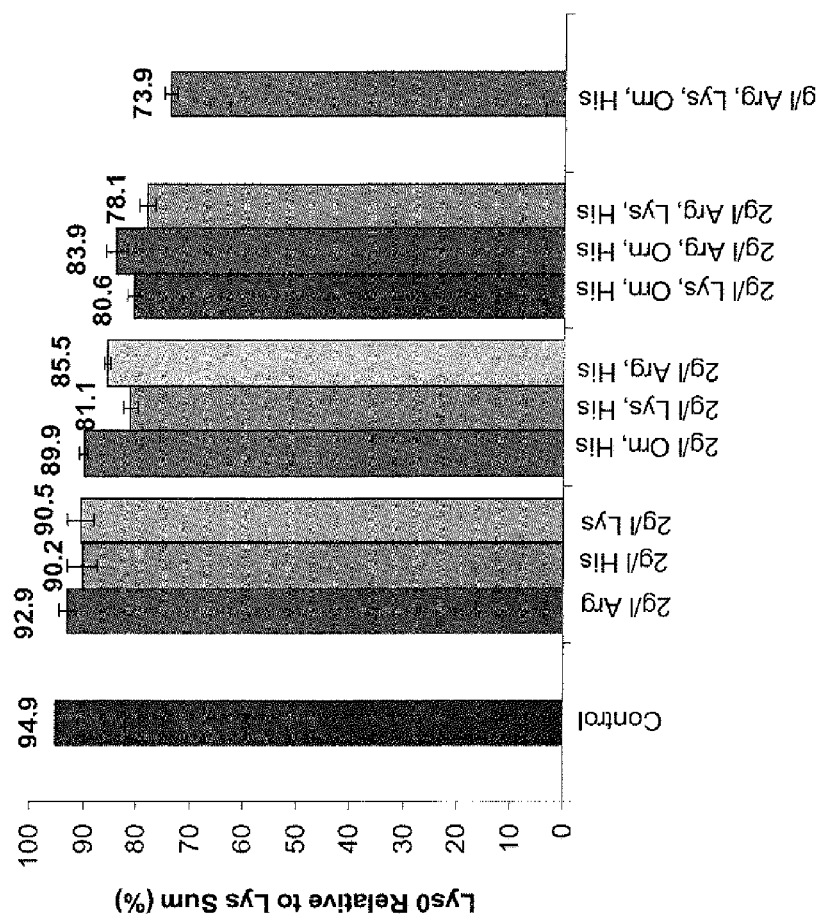
Figure 58) Effect of multiple amino acid additions to adalimumab producing cell line 2, media 1 containing 1g/l arginine and 1g/l lysine on WCX 10 profile relative lysine distribution (n=2)

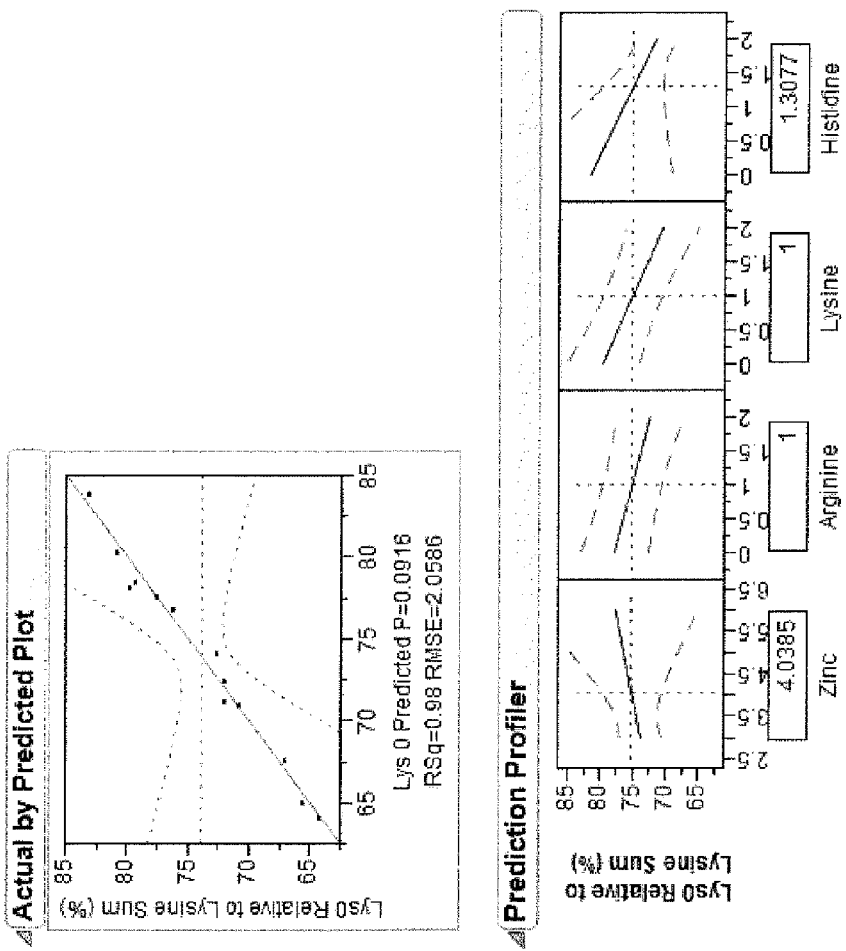
Figure 59) Effect of modulations of zinc and multiple amino acid concentrations in adalimumab producing cell line 1, media 1 on WCX 10 profile relative lysine distribution a) overall prediction plot, b) prediction plots for each additive

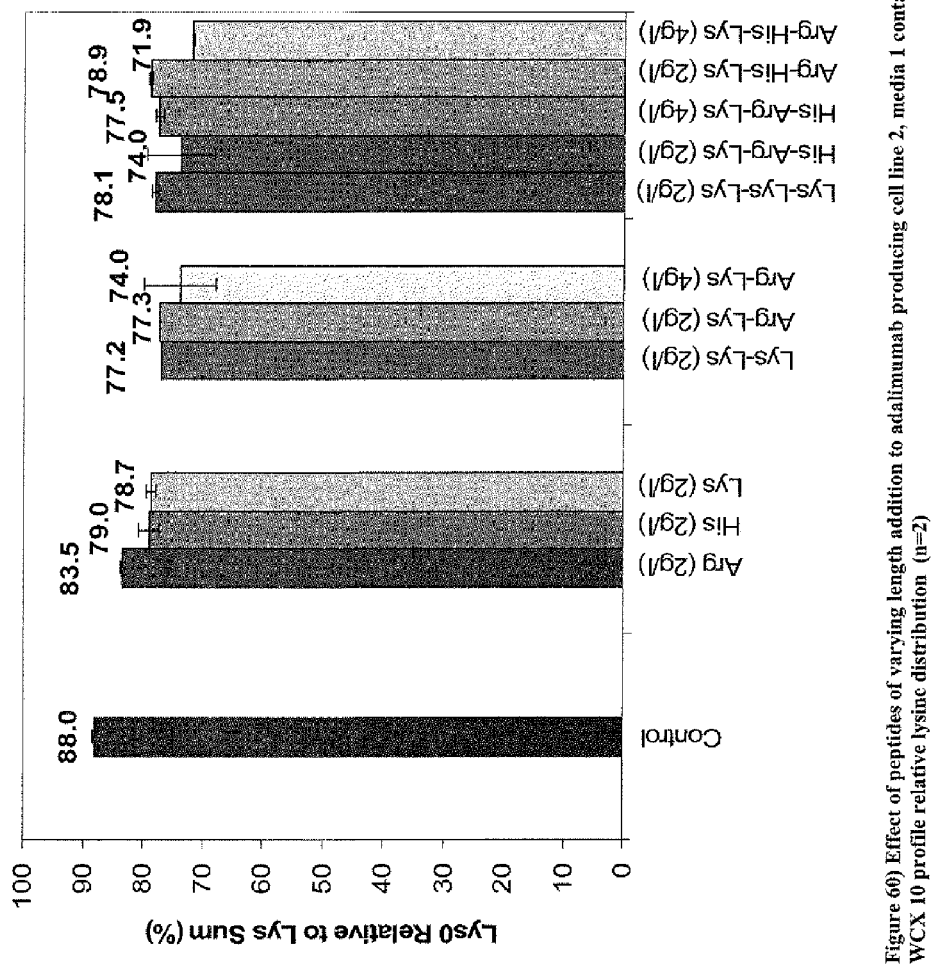
Figure 60) Effect of peptides of varying length addition to adalimumab producing cell line 2, media 1 containing 1g/l arginine and 1g/l lysine on WCX 10 profile relative lysine distribution (n=2)

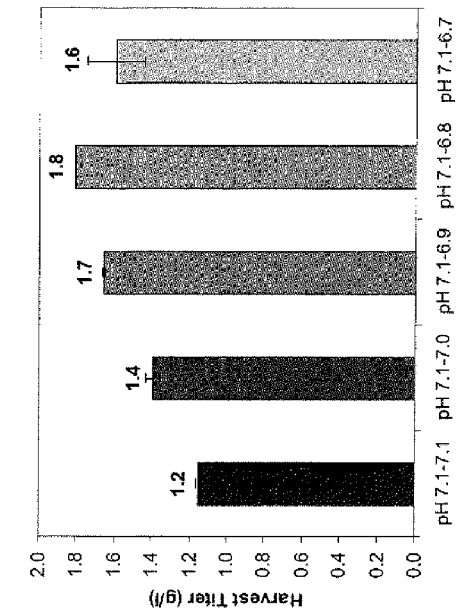

Figure 61) Effect of pH modulation to adalimumab producing cell line 1, media 1 on viable cell density (n=2)

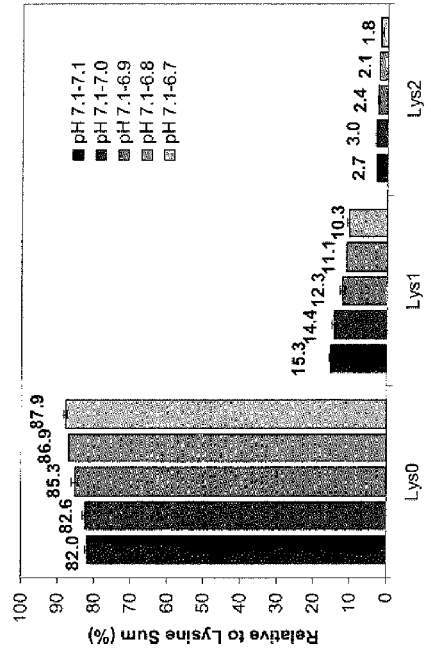

Figure 63) Effect of pH modulation to adalimumab producing cell line 1, media 1 on harvest titer (n=2)

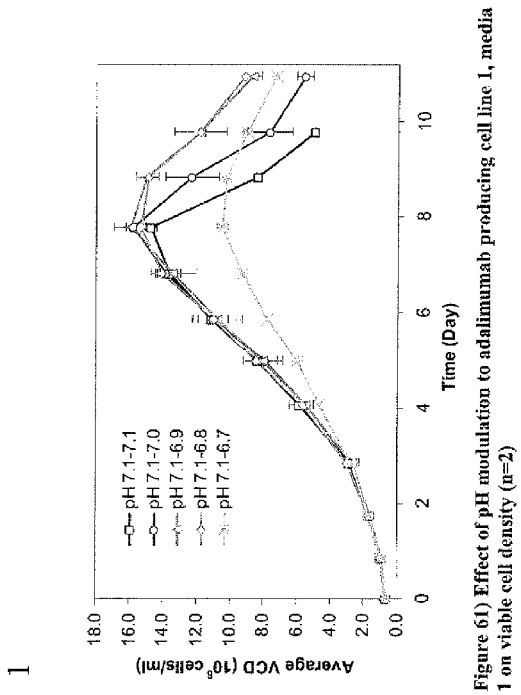

Figure 62) Effect of pH modulation to adalimumab producing cell line 1, media 1 on viability (n=2)

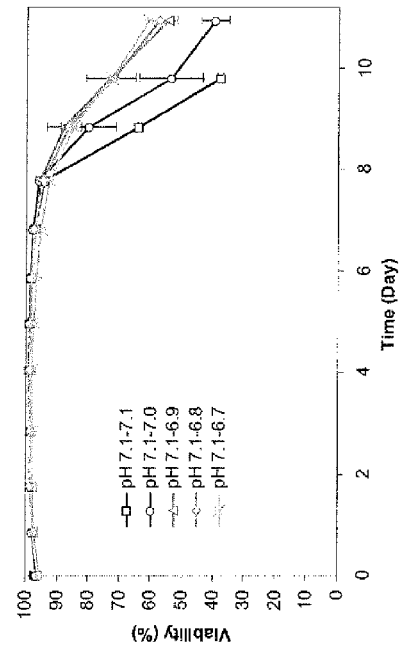

Figure 64) Effect of pH modulation to adalimumab producing cell line 1, media 1 on WCX 10 profile relative lysine distribution (n=2)

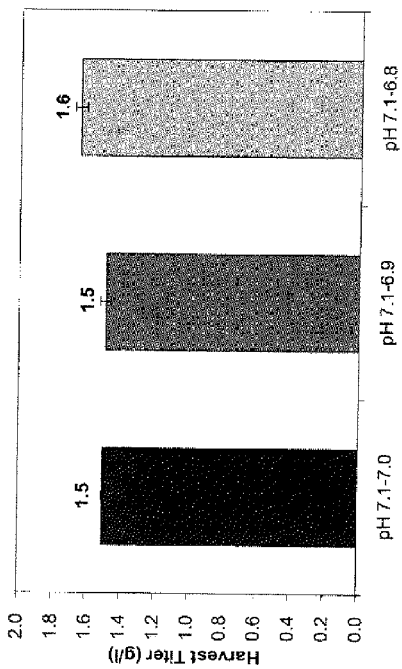

Figure 65) Effect of pH modulation to adalimumab producing cell line 1, media 2 on viable cell density (n=2)

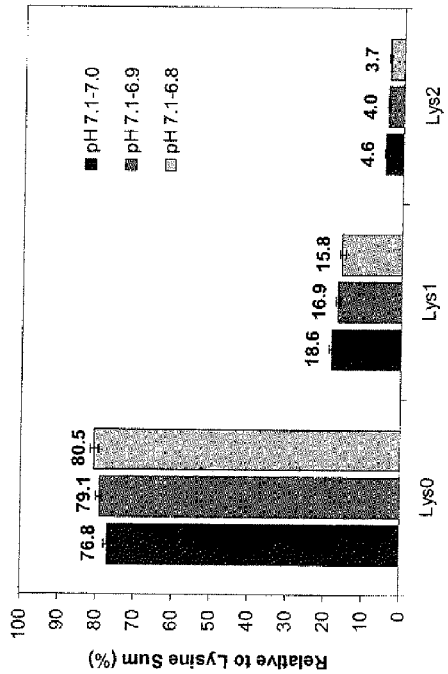

Figure 67) Effect of pH modulation to adalimumab producing cell line 1, media 2 on harvest titer (n=2)

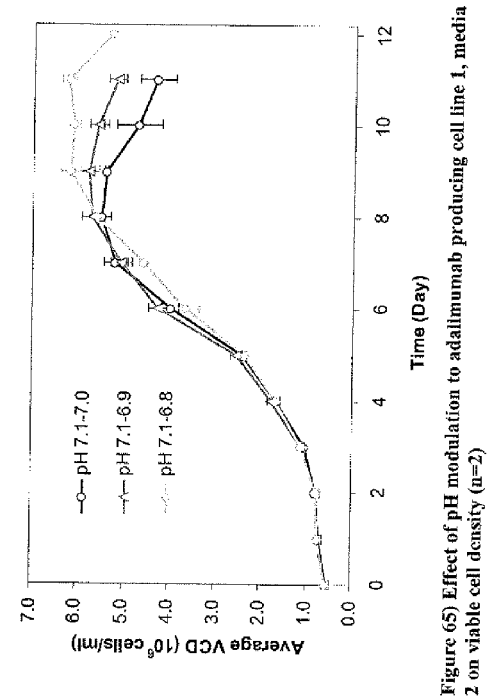

Figure 66) Effect of pH modulation to adalimumab producing cell line 1, media 2 on viability (n=2)

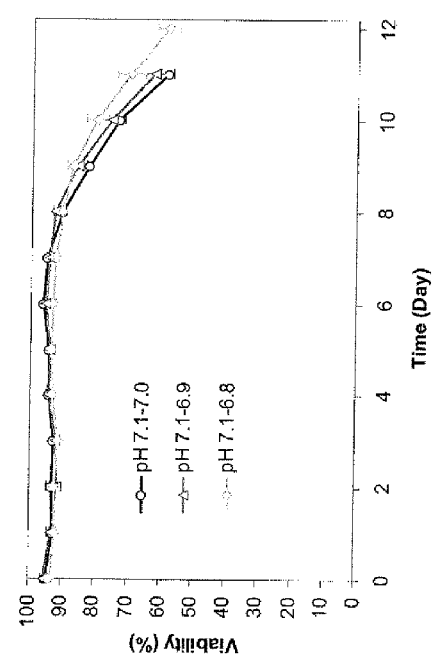

Figure 68) Effect of pH modulation to adalimumab producing cell line 1, media 2 on WCX 10 profile relative lysine distribution (n=2)

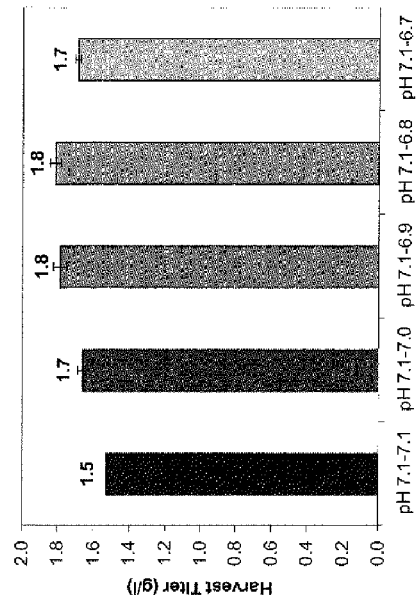

Figure 69) Effect of pH modulation to adalimumab producing cell line 3, media 1 on viable cell density (n=2)

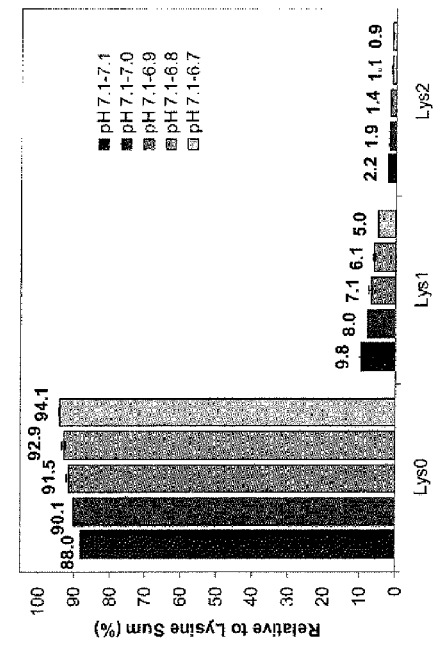

Figure 71) Effect of pH modulation to adalimumab producing cell line 3, media 1 on harvest titer (n=2)

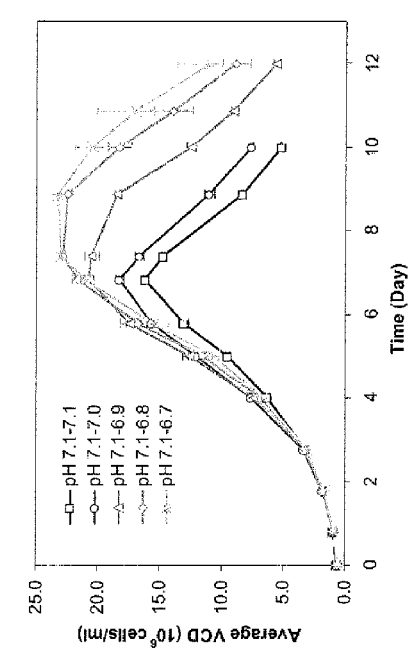

Figure 70) Effect of pH modulation to adalimumab producing cell line 3, media 1 on viability (n=2)

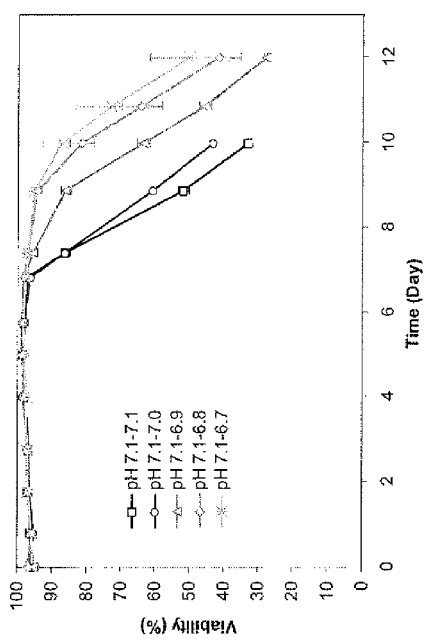

Figure 72) Effect of pH modulation to adalimumab producing cell line 3, media 1 on WCX 10 profile relative lysine distribution (n=2)

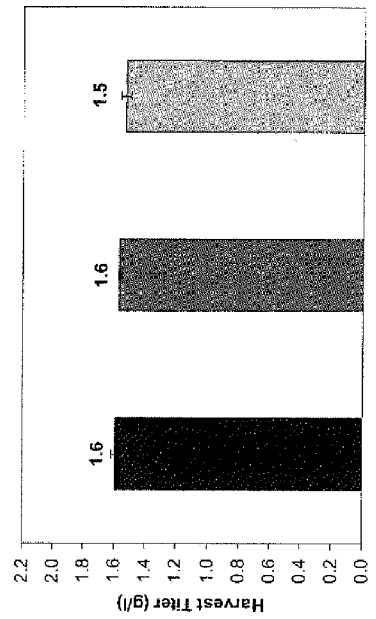
Figure 75) Effect of temperature modulation to adalimumab producing cell line 1, media 1 on harvest titer (n=2)
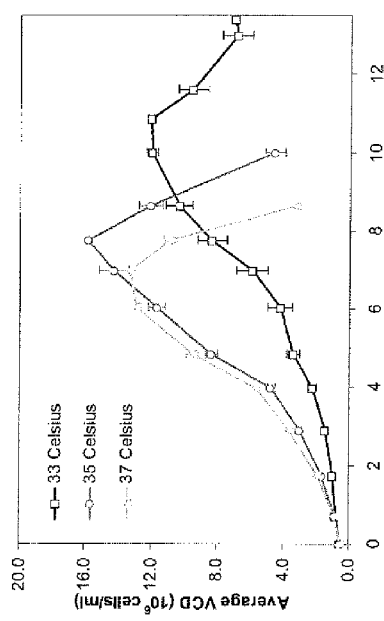
Figure 73) Effect of temperature modulation to adalimumab producing cell line 1, media 1 on viable cell density (n=2)
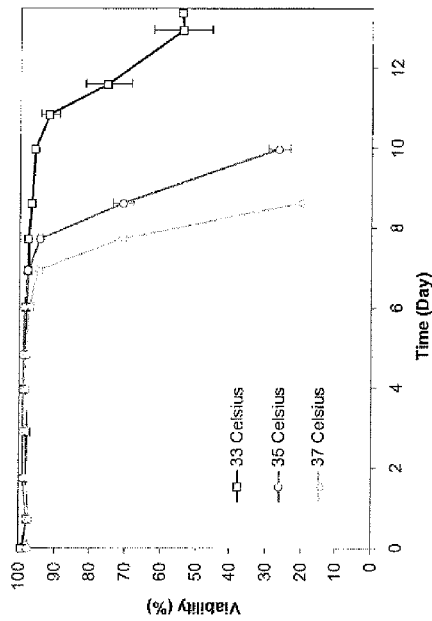
Figure 74) Effect of temperature modulation to adalimumab producing cell line 1, media 1 on viability (n=2)

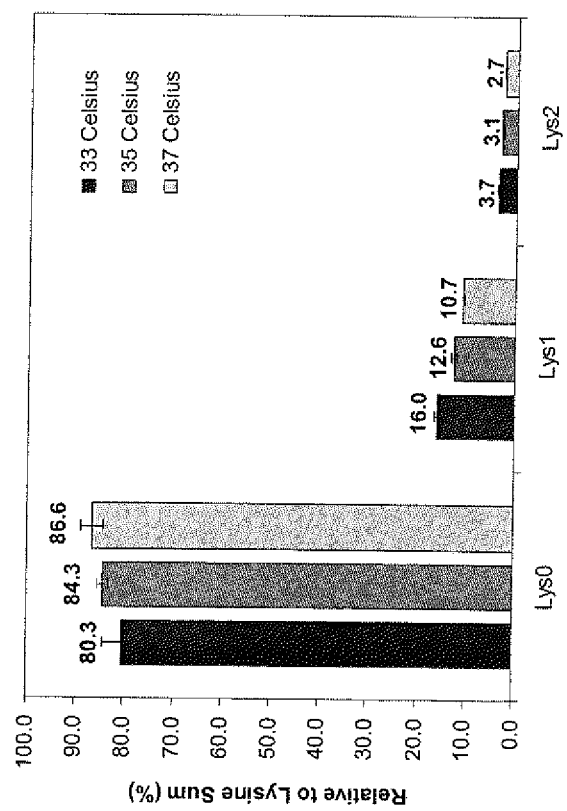
Figure 76) Effect of temperature modulation to adalimumab producing cell line 1, media 1 on WCX 10 profile relative lysine distribution (n=2)

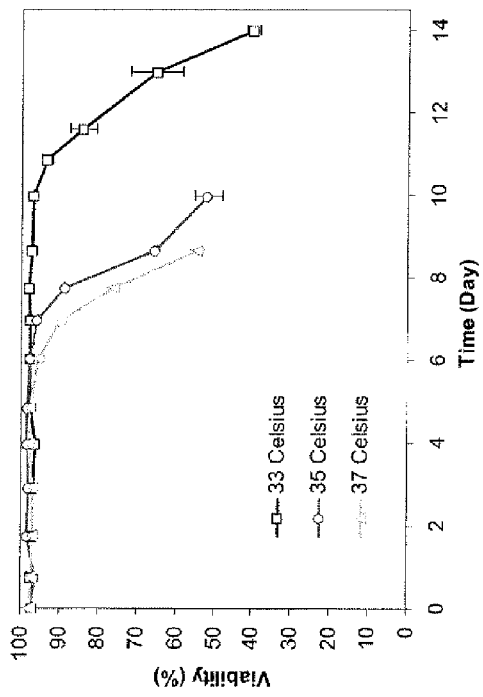
Figure 78) Effect of temperature modulation to adalimumab producing cell line 1, media 1 on viability (n=2)
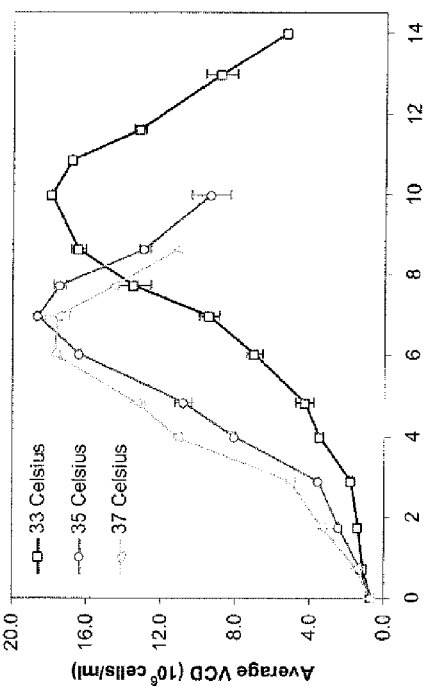
Figure 77) Effect of temperature modulation to adalimumab producing cell line 1, media 1 on viable cell density (n=2)

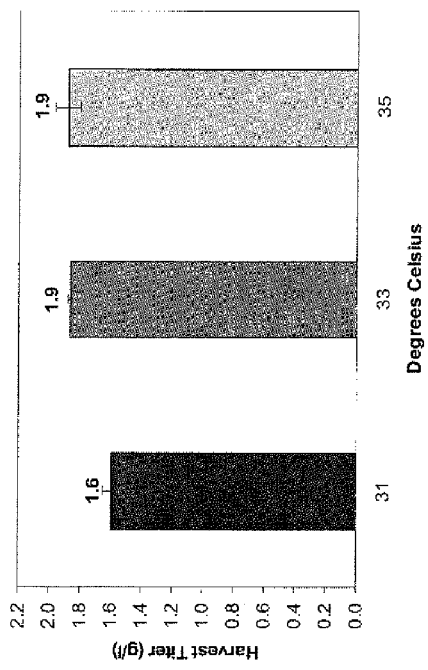
Figure 79) Effect of temperature modulation to adalimumab producing cell line 1, media 1 on harvest titer (n=2)
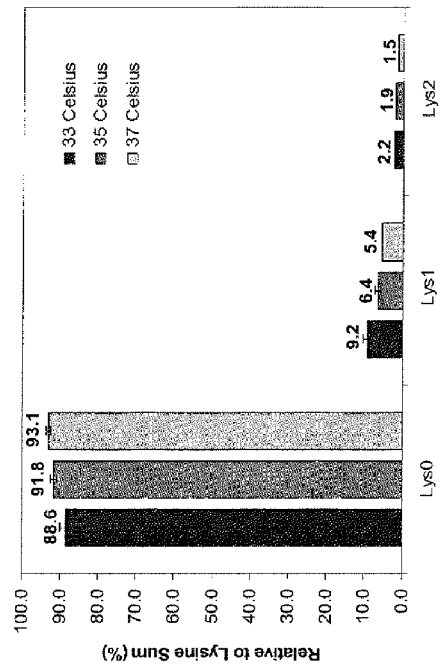
Figure 80) Effect of temperature modulation to adalimumab producing cell line 1, media 1 on WCX 10 profile relative lysine distribution (n=2)

METHODS TO MODULATE LYSINE VARIANT DISTRIBUTION

CROSS REFERENCE TO RELATED APPLICATIONS

The present application claims priority to U.S. Provisional Application Nos. 61/636,469, filed on Apr. 20, 2012 and 61/696,207, filed on Sep. 2, 2012, the disclosures of which are incorporated by reference herein in their entireties.

1. INTRODUCTION

The instant invention relates to the field of recombinant protein production and purification of recombinant proteins, and in particular to compositions and processes for controlling the relative distribution of C-terminal lysine variants of proteins (e.g., antibodies) expressed by recombinant host cells. In certain aspects of the invention, controlling the relative distribution of the different C-terminal lysine variants of protein expressed by recombinant host cells is achieved by modifying conditions employed in culturing the cells.

2. BACKGROUND OF THE INVENTION

Large-scale production of proteins for biopharmaceutical applications involves the use of cell cultures that are known to produce proteins exhibiting varying levels of heterogeneity. One potential source of heterogeneity involves C-terminal lysine residues, such as those typically found on the heavy chains of antibody molecules. C terminal lysines can be lost, so that individual antibodies in a production batch can vary at their C terminus as to whether a lysine residue is present. C-terminal lysines can be potentially present on both the heavy chains of an antibody (Lys 2), on either one of the heavy chains (Lys 1), or neither of them (Lys 0). Since lysine can carry a positive charge, antibodies lacking the basic C-terminal lysine(s) differ in the charge state from the ones that contain the lysine, so that the distribution of lysine variants (% Lys 0, % Lys 1, % Lys 2 of the total Lysine Sum) can be detected by ion-exchange chromatographic methods, such as analysis employing a ProPac WCX-10 Weak Cation-Exchange column for the high-resolution separation of protein isoforms (Dionex, Calif.), and subsequently quantified.

The C-terminal lysine heterogeneity is commonly observed in biopharmaceutical antibodies and proteins. For instance, in the process of manufacture of Remicade (Infliximab), the heterogeneity during the fermentation was approximately 20% (Lys 0 and Lys 1) and 80% (Lys 2) (US Patent Application publication US2010/0297697A1). Other examples are detailed in a review article on lysine variants (Harris R, "Processing of C-terminal lysine and arginine residues of proteins isolated from mammalian cell culture" Journal of Chromatography A, 705 129-134 (1995)).

The present study is directed to cell culture methods to modulate a product quality attribute of recombinant proteins. Specifically, the invention provides methods for influencing the relative distribution of the different C-terminal lysine variants of the product antibody obtained from the cell culture harvest. C-terminal lysine can be potentially present on both the heavy chains of the antibody (Lys 2), on either one of them (Lys 1) or neither of them (Lys 0). Since, antibodies lacking the basic C-terminal lysine(s) differ in the charge state from the ones that contain the lysine, the distribution of lysine variants (% Lys 0, % Lys 1, % Lys 2 of the total Lysine Sum) can be detected by ion-exchange chromatographic methods such as WCX-10 and subsequently quantified (FIG. 1).

3. SUMMARY OF THE INVENTION

The present invention is directed to compositions and methods that control (modulate or limit) the extent of lysine variant heterogeneity in a population of proteins produced by cell culture. In certain embodiments, control is exerted over the distribution or amount of lysine variants of protein produced by cell culture. In certain embodiments, the protein is an antibody. In certain embodiments such control is exerted in order to facilitate consistency and reproducibly in obtaining a particular lysine variant distribution, e.g., in the production of a therapeutic antibody. The variant distribution in such contexts may change due to a number of reasons, e.g., processes changes such altering media usage, and the methods described herein allow for the production of compositions of the desired lysine variant specification.

Heterogeneity of C-terminal lysine variants, as that term is used herein, can refer to (i) the presence of subspecies of protein molecules which differ from one another based on whether a full or partial complement of C-terminal lysines are present (or whether C-terminal lysine(s) is (are) absent); and/or (ii) to the relative proportion or amount of said subspecies in the population. In certain embodiments, heterogeneity can arise from both a difference in the amount of C-terminal lysine variants in the population of proteins and the subspecies of C-terminal lysine variants present in the population (species) of protein.

In certain embodiments, the protein is an antibody, and control is exerted over the distribution or amount of C-terminal lysine variants to decrease the relative amount of a Lys 0 lysine variant in a population of proteins produced by cell culture, wherein the Lys 0 lysine variant comprises an antibody with heavy chains that do not comprise a C-terminal lysine. In certain embodiments, control is exerted over the distribution or amount of C-terminal lysine variants to decrease the amount of a Lys 1 lysine variant in a population of proteins produced by cell culture, wherein the Lys 1 lysine variant comprises an antibody with one heavy chain that comprises a C-terminal lysine. In certain embodiments, control is exerted over the distribution or amount of C-terminal lysine variants to decrease the amount of a Lys 2 lysine variant in a population of proteins produced by cell culture, wherein the Lys 2 lysine variant comprises an antibody wherein both heavy chains comprise a C-terminal lysine. In certain embodiments, control is exerted over the distribution or amount of C-terminal lysine variants to increase the amount of a Lys 0 lysine variant in a population of proteins produced by cell culture. In certain embodiments, control is exerted over the distribution or amount of C-terminal lysine variants to increase the amount of a Lys 1 lysine variant in a population of proteins produced by cell culture. In certain embodiments, control is exerted over the distribution or amount of C-terminal lysine variants to increase the amount of a Lys 2 lysine variant in a population of proteins produced by cell culture.

In certain embodiments, control over the distribution or amount of C-terminal lysine variants produced by cell culture is exerted by employing certain media components during production of a protein, for example, an antibody, of interest. In certain embodiments, control over the distribution or amount of C-terminal lysine variants produced by cell culture is exerted by supplementing the media of cells expressing the protein of interest with one or more amino acids. In certain embodiments, one or more of the amino acids belong to a group of basic amino acids. In certain embodiments, the one or more amino acids is arginine, lysine, histidine, or combinations thereof, including combinations of arginine and/or lysine with ornithine. In certain embodiments, supplementing the media of cells expressing the protein of interest with one or more amino acids reduces the relative amount of a Lys 0 lysine variant, and increases the relative amount of a Lys 1 and/or Lys 2 lysine variant in the cell culture or a composition comprising the protein or antibody purified from the cell culture. In certain embodiments, these amino acids may be supplemented as dipeptides or tri-peptides of different combinations for lysine variant modulation In certain embodiments, control over the distribution or amount of C-terminal lysine variants produced by cell culture is exerted by controlling the amount of Zinc present in the media employed in culturing the cells expressing the protein of interest. In certain embodiments, supplementing the media of cells expressing the protein of interest with Zinc to an overall concentration of less than about 10 μM reduces the relative amount of a Lys 0 lysine variant, and increases the relative amount of a Lys 1 and/or Lys 2 lysine variant in the cell culture or a composition comprising the protein or antibody purified from the cell culture. In certain embodiments, modulation of concentration of zinc in combination with that of the basic amino acids is used to modulate the lysine variant distribution.

In certain embodiments, control over the distribution or amount of C-terminal lysine variants produced by cell culture is exerted by adjusting the pH, and/or temperature of a cell culture expressing a protein or antibody of interest. In certain embodiments, increasing the pH of the cell culture expressing the protein or antibody of interest reduces the amount of a Lys 0 lysine variant, and increases the amount of a Lys 1 and/or Lys 2 lysine variant in the cell culture, or a composition comprising the protein or antibody purified from the cell culture, compared to a control cell culture at a lower pH. In certain embodiments, the final pH of the cell culture is adjusted to a pH of about 6.7 to about 7.1. In certain embodiments, the temperature of the cell culture is adjusted to a temperature of about 31 to about 37° C. In certain embodiments, decreasing the temperature of the cell culture expressing the protein or antibody of interest reduces the amount of a Lys 0 lysine variant, and increases the amount of a Lys 1 and/or Lys 2 lysine variant in the cell culture, or a composition comprising the protein or antibody purified from the cell culture, compared to a control cell culture at a higher temperature.

In certain embodiments, the methods of culturing cells expressing a protein of interest, such as an antibody or antigen-binding portion thereof, or purifying such protein from a sample, as described herein, modulates the distribution, reduces the amount, or increases the amount of lysine variants present in the resulting composition. In certain embodiments, the resulting composition has a reduced amount of Lys 0 lysine variant, and an increased amount of Lys 1 and Lys 2 lysine variants compare to a composition that was not prepared according to the methods of the present application. In one aspect, the sample comprises a cell harvest wherein the cell line is employed to produce specific proteins of the present invention. In a particular aspect, the sample is prepared from a cell line used to produce anti-TNF-α antibodies.

In certain embodiments, control over the subspecies and/or amount of C-terminal lysine variants in the protein compositions described herein is exerted by employing one or more of the foregoing methods during the production and purification of the desired proteins, such as antibodies or antigen-binding portions thereof, described herein.

The purity/heterogeneity of the proteins of interest in the resultant sample product can be analyzed using methods well known to those skilled in the art, e.g., weak cation exchange chromatography (WCX), capillary isoelectric focusing (cIEF), size-exclusion chromatography, Poros™ A HPLC Assay, Host Cell Protein ELISA, Protein A ELISA, and western blot analysis.

In yet another embodiment, the invention is directed to one or more pharmaceutical compositions comprising an isolated protein, such as an antibody or antigen-binding portion thereof, and an acceptable carrier. In another aspect, the compositions further comprise one or more pharmaceutical agents.

4. BRIEF DESCRIPTION OF THE DRAWINGS

FIG. 1 is a representation of the lysine variants in a sample WCX-10 chromatogram and quantification scheme of each of the variants.

FIG. 2 depicts the effect of zinc modulation in adalimumab producing cell line 1, media 1 on viable cell density (n=2).

FIG. 3 depicts the effect of zinc modulation in adalimumab producing cell line 1, media 1 on viability (n=2).

FIG. 4 depicts the effect of zinc modulation in adalimumab producing cell line 1, media 1 on harvest titer (n=2)

FIG. 5 depicts the effect of zinc modulation in adalimumab producing cell line 1, media 1 on day 10 WCX 10 profile relative lysine distribution (n=2).

FIG. 6 depicts the effect of zinc modulation in adalimumab producing cell line 1, media 1 on viable cell density (n=2).

FIG. 7 depicts the effect of zinc modulation in adalimumab producing cell line 1, media 1 on viability (n=2).

FIG. 8 depicts the effect of zinc modulation in adalimumab producing cell line 1, media 1 on harvest titer (n=2).

FIG. 9 depicts the effect of zinc modulation in adalimumab producing cell line 1, media 1 on day 10 WCX 10 profile relative lysine distribution (n=2).

FIG. 10 depicts the effect of total arginine concentration in adalimumab producing cell line 2, media 1 on viable cell density (n=2).

FIG. 11 depicts the effect of total arginine concentration in adalimumab producing cell line 2, media 1 on viability (n=2).

FIG. 12 depicts the effect of total arginine concentration in adalimumab producing cell line 2, media 1 on harvest titer (n=2).

FIG. 13 depicts the effect of total arginine concentration in adalimumab producing cell line 2, media 1 on day 10 on WCX 10 profile relative lysine distribution (n=2).

FIG. 14 depicts the effect of total arginine concentration in adalimumab producing cell line 2, media 1 on day 12 on WCX 10 profile relative lysine distribution (n=2).

FIG. 15 depicts the effect of total arginine concentration in adalimumab producing cell line 3, media 1 on viable cell density (n=2).

FIG. 16 depicts the effect of total arginine concentration in adalimumab producing cell line 3, media 1 on viability (n=2).

FIG. 17 depicts the effect of total arginine concentration in adalimumab producing cell line 3, media 1 on harvest titer (n=2).

FIG. 18 depicts the effect of total arginine concentration in adalimumab producing cell line 3, media 1 on WCX 10 profile relative lysine distribution (n=2).

FIG. 19 depicts the effect of total arginine concentration in adalimumab producing cell line 1, media 1 on WCX 10 profile relative lysine distribution (n=2).

FIG. 20 depicts the effect of arginine addition to adalimumab producing cell line 1, media 2 on day 11 on WCX-10 profile relative lysine distribution (n=2).

FIG. 21 depicts the effect of arginine addition to adalimumab producing cell line 2, media 3 on WCX-10 profile relative lysine distribution (n=2).

FIG. 22 depicts the effect of total arginine concentration in mAB1 producing cell line on WCX-10 profile relative lysine distribution (n=1).

FIG. 23 depicts the effect of total arginine concentration in mAB2 producing cell line on WCX-10 profile relative lysine distribution (n=2).

FIG. 24 depicts the effect of total lysine concentration in adalimumab producing cell line 2, media 1 on viable cell density (n=2).

FIG. 25 depicts the effect of total lysine concentration in adalimumab producing cell line 2, media 1 on viability (n=2).

FIG. 26 depicts the effect of total lysine concentration in adalimumab producing cell line 2, media 1 on harvest titer (n=2).

FIG. 27 depicts the effect of total lysine concentration in adalimumab producing cell line 2, media 1 on WCX 10 profile relative lysine distribution (n=2).

FIG. 28 depicts the effect of total lysine concentration in adalimumab producing cell line 3, media 1 on viable cell density (n=2).

FIG. 29 depicts the effect of total lysine concentration in adalimumab producing cell line 3, media 1 on viability (n=2).

FIG. 30 depicts the effect of total lysine concentration in adalimumab producing cell line 3, media 1 on harvest titer (n=2).

FIG. 31 depicts the effect of total lysine concentration in adalimumab producing cell line 3, media 1 on WCX 10 profile relative lysine distribution (n=2).

FIG. 32 depicts the effect of total lysine concentration in adalimumab producing cell line 1, media 1 on WCX 10 profile relative lysine distribution (n=2).

FIG. 33 depicts the effect of lysine addition to adalimumab producing cell line 1, media 2 on WCX-10 profile relative lysine distribution (n=2).

FIG. 34 depicts the effect of lysine addition to adalimumab producing cell line 2, media 3 on WCX-10 profile relative lysine distribution (n=2).

FIG. 35 depicts the effect of total lysine concentration in mAB1 producing cell line on WCX-10 profile relative lysine distribution (n=1).

FIG. 36 depicts the effect of total lysine concentration in mAB2 producing cell line on WCX-10 profile relative lysine distribution (n=2).

FIG. 37 depicts the effect of total histidine concentration in adalimumab producing cell line 2, media 1 on viable cell density (n=2).

FIG. 38 depicts the effect of total histidine concentration in adalimumab producing cell line 2, media 1 on viability (n=2).

FIG. 39 depicts the effect of total histidine concentration in adalimumab producing cell line 2, media 1 on harvest titer (n=2).

FIG. 40 depicts the effect of total histidine concentration in adalimumab producing cell line 2, media 1 on WCX 10 profile relative lysine distribution (n=2).

FIG. 41 depicts the effect of total histidine concentration in adalimumab producing cell line 3, media 1 on viable cell density (n=2).

FIG. 42 depicts the effect of total histidine concentration in adalimumab producing cell line 3, media 1 on viability (n=2).

FIG. 43 depicts the effect of total histidine concentration in adalimumab producing cell line 3, media 1 on harvest titer (n=2).

FIG. 44 depicts the effect of total histidine concentration in adalimumab producing cell line 3, media 1 on WCX 10 profile relative lysine distribution (n=2).

FIG. 45 depicts the effect of total histidine concentration in adalimumab producing cell line 1, media 1 on WCX 10 profile relative lysine distribution (n=2).

FIG. 46 depicts the effect of histidine addition to adalimumab producing cell line 1, media 2 on WCX-10 profile relative lysine distribution (n2).

FIG. 47 depicts the effect of histidine addition to adalimumab producing cell line 2, media 3 on WCX-10 profile relative lysine distribution (n=2).

FIG. 48 depicts the effect of total histidine concentration in mAB1 producing cell line on WCX-10 profile relative lysine distribution (n=1).

FIG. 49 depicts the effect of total histidine concentration in mAB2 producing cell line on WCX-10 profile relative lysine distribution (n=2).

FIG. 50 depicts the effect of concentration modulation of multiple amino acids to adalimumab producing cell line 1, media 1 on viable cell density (n=2).

FIG. 51 depicts the effect of concentration modulation of multiple amino acids to adalimumab producing cell line 1, media 1 on viability.

FIG. 52 depicts the effect of concentration modulation of multiple amino acids to adalimumab producing cell line 1, media 1 on harvest titer.

FIG. 53 depicts the effect of concentration modulation of multiple amino acids to adalimumab producing cell line 1, media 1 on WCX 10 profile relative lysine distribution.

FIG. 54 depicts the effect of concentration modulation of multiple amino acids to adalimumab producing cell line 3, media 1 on viable cell density (n=2).

FIG. 55 depicts the effect of concentration modulation of multiple amino acids to adalimumab producing cell line 3, media 1 on viability.

FIG. 56 depicts the effect of concentration modulation of multiple amino acids to adalimumab producing cell line 3, media 1 on harvest titer.

FIG. 57 depicts the effect of concentration modulation of multiple amino acids to adalimumab producing cell line 3, media 1 on WCX 10 profile relative lysine distribution.

FIG. 58 depicts the effect of concentration modulation of multiple amino acids to adalimumab producing cell line 2, media 1 on WCX 10 profile relative lysine distribution (n=2).

FIG. 59 depicts the effect of concentration modulation of zinc and multiple amino acids to adalimumab producing cell line 1, media 1 on WCX 10 profile relative lysine distribution a) overall prediction plot, b) prediction plots for each additive.

FIG. 60 depicts the effect of peptides of varying length addition to adalimumab producing cell line 2, media 1 on WCX 10 profile relative lysine distribution (n2).

FIG. 61 depicts the effect of pH modulation to adalimumab producing cell line 1, media 1 on viable cell density (n=2).

FIG. 62 depicts the effect of pH modulation to adalimumab producing cell line 1, media 1 on viability (n=2).

FIG. 63 depicts the effect of pH modulation to adalimumab producing cell line 1, media 1 on harvest titer (n=2).

FIG. 64 depicts the effect of pH modulation to adalimumab producing cell line 1, media 1 on WCX 10 profile relative lysine distribution (n=2).

FIG. 65 depicts the effect of pH modulation to adalimumab producing cell line 1, media 2 on viable cell density (n=2).

FIG. 66 depicts the effect of pH modulation to adalimumab producing cell line 1, media 2 on viability (n=2).

FIG. 67 depicts the effect of pH modulation to adalimumab producing cell line 1, media 2 on harvest titer (n=2).

FIG. 68 depicts the effect of pH modulation to adalimumab producing cell line 1, media 2 on WCX 10 profile relative lysine distribution (n=2).

FIG. 69 depicts the effect of pH modulation to adalimumab producing cell line 3, media 1 on viable cell density (n=2).

FIG. 70 depicts the effect of pH modulation to adalimumab producing cell line 3, media 1 on viability (n=2).

FIG. 71 depicts the effect of pH modulation to adalimumab producing cell line 3, media 1 on harvest titer (n=2).

FIG. 72 depicts the effect of pH modulation to adalimumab producing cell line 3, media 1 on WCX 10 profile relative lysine distribution (n=2).

FIG. 73 depicts the effect of temperature modulation to adalimumab producing cell line 1, media 1 on viable cell density (n=2).

FIG. 74 depicts the effect of temperature modulation to adalimumab producing cell line 1, media 1 on viability (n=2).

FIG. 75 depicts the effect of temperature modulation to adalimumab producing cell line 1, media 1 on harvest titer (n=2).

FIG. 76 depicts the effect of temperature modulation to adalimumab producing cell line 1, media 1 on WCX 10 profile relative lysine distribution (n=2).

FIG. 77 depicts the effect of temperature modulation to adalimumab producing cell line 1, media 1 on viable cell density (n=2).

FIG. 78 depicts the effect of temperature modulation to adalimumab producing cell line 1, media 1 on viability (n=2).

FIG. 79 depicts the effect of temperature modulation to adalimumab producing cell line 1, media 1 on harvest titer (n=2).

FIG. 80 depicts the effect of temperature modulation to adalimumab producing cell line 1, media 1 on WCX 10 profile relative lysine distribution (n=2).

5. DETAILED DESCRIPTION OF THE INVENTION

The instant invention relates to the field of protein production and purification. In particular, the instant invention relates to compositions and processes for controlling the distribution or amount of C-terminal lysine variants expressed by host cells when used to produce a protein of interest, as well as compositions and processes for controlling the distribution or amount of C-terminal lysine variants present in purified preparations of a protein of interest. Certain embodiments of the invention relate to culturing said cells and/or purifying said proteins under conditions that modulate the distribution or amount of C-terminal lysine variants that are expressed by the cells or are present in purified protein preparations. In certain embodiments, the methods described herein employ culturing said cells in the presence of one or more amino acids. In certain embodiments, the methods described herein employ culturing said cells in the presence of Zinc, including, but not limited to, when Zinc is present in combination with one or more amino acids. In certain embodiments, the methods described herein employ culturing said cells under conditions of increased or decreased temperatures compared to a control temperature. In certain embodiments, the methods described herein employ culturing said cells under conditions of increased or decreased pH compared to a control pH. In certain embodiments, the present invention is directed toward pharmaceutical compositions comprising one or more proteins, such as, but not limited to an antibody or antigen-binding portion thereof, purified by a method described herein. In certain embodiments such control is exerted in order to facilitate consistency and reproducibly in obtaining a particular lysine variant distribution, e.g., in the production of a therapeutic antibody. The variant distribution in such contexts may change due to a number of reasons, e.g., processes changes such altering media usage, and the methods described herein allow for the production of compositions of the desired lysine variant specification.

For clarity and not by way of limitation, this detailed description is divided into the following sub-portions:
(i) Definitions;
(ii) Antibody Generation;
(iii) Protein Production;
(iv) Protein Purification; and
(v) Pharmaceutical Compositions.

5.1 Definitions

In order that the present invention may be more readily understood, certain terms are first defined.

As used herein, the term "lysine variant heterogeneity" refers to a characteristic of a population of proteins wherein the population consists of proteins of substantially identical amino acid sequence, but where the population exhibits variation in the presence or absence of C-terminal lysine residues. Although such lysine variant heterogeneity can be observed under general cell culture conditions, the use of particular cell culture conditions, as detailed below, can increase or decrease the distribution or amount of lysine variant heterogeneity.

In certain embodiments, the protein is an antibody, and the distribution of lysine variant heterogeneity comprises a distribution of the lysine variants Lys 0, Lys 1 and Lys 2, wherein the Lys 0 lysine variant comprises an antibody with heavy chains that do not comprise a C-terminal lysine, wherein the Lys 1 lysine variant comprises an antibody with one heavy chain that comprises a C-terminal lysine, and wherein the Lys 2 lysine variant comprises an antibody wherein both heavy chains comprise a C-terminal lysine.

In certain embodiments, C-terminal lysine variants are associated with charge heterogeneities present in protein preparations, for example, monoclonal antibody (mAb) preparations, produced through a cell culture process. These heterogeneities can be detected by various methods, such as, for example, WCX-10 HPLC (a weak cation exchange chromatography), or IEF (isoelectric focusing).

In certain embodiments, the heterogeneity arises from subspecies of protein differing by the presence or absence of C-terminal lysines. For example, the population of proteins may comprise more than one subspecies of lysine variant. In one non-limiting example, the lysine variants may comprise at least two of Lys 0, Lys 1 and Lys 2 lysine variants which can be detected by weak cation exchange chromatography of the expression product of a host cell expressing adalimumab.

In certain embodiments, the heterogeneity arises from the size of subpopulations having different C-terminal lysine profiles. For example, the population of proteins may comprise more than one subspecies of C-terminal lysine variant, and each of the variants may be present in different amounts. In one non-limiting example, the C-terminal lysine variants may be at least two of the Lys 0, Lys 1 and Lys 2 lysine variants detected by weak cation exchange chromatography of the expression product of a host cell expressing adalimumab. In certain embodiments, Lys 0, Lys 1 or Lys 2 subspecies are present in different amounts.

In certain embodiments, the heterogeneity arises from both a difference in the amount of lysine variants in the population of proteins and the type of lysine variants present in the population of proteins.

The term "antibody" includes an immunoglobulin molecule comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region (CH). The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The term "antigen-binding portion" of an antibody (or "antibody portion") includes fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment comprising the VL, VH, CL and CH1 domains; (ii) a F(ab')2 fragment, a bivalent fragment comprising two Fab fragments linked by a disulfide bridge at the hinge region; (iii) a Fd fragment comprising the VH and CH1 domains; (iv) a Fv fragment comprising the VL and VH domains of a single arm of an antibody, (v) a dAb fragment (Ward et al., (1989) Nature 341:544-546, the entire teaching of which is incorporated herein by reference), which comprises a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al. (1988) Science 242:423-426; and Huston et al. (1988) Proc. Natl. Acad. Sci. USA 85:5879-5883, the entire teachings of which are incorporated herein by reference). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, e.g., Holliger, P., et al. (1993) Proc. Natl. Acad. Sci. USA 90:6444-6448; Poljak, R. J., et al. (1994) Structure 2:1121-1123, the entire teachings of which are incorporated herein by reference). Still further, an antibody or antigen-binding portion thereof may be part of a larger immunoadhesion molecule, formed by covalent or non-covalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101, the entire teaching of which is incorporated herein by reference) and use of a cysteine residue, a marker peptide and a C-terminal polyhistidine tag to make bivalent and biotinylated scFv molecules (Kipriyanov, S. M., et al. (1994) Mol. Immunol. 31:1047-1058, the entire teaching of which is incorporated herein by reference). Antibody portions, such as Fab and F(ab')2 fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein. In one aspect, the antigen binding portions are complete domains or pairs of complete domains.

The phrase "clarified harvest" refers to a liquid material containing a protein of interest, for example, an antibody of interest such as a monoclonal or polyclonal antibody of interest, that has been extracted from cell culture, for example, a fermentation bioreactor, after undergoing centrifugation to remove large solid particles and subsequent filtration to remove finer solid particles and impurities from the material.

The term "human antibody" includes antibodies having variable and constant regions corresponding to human germline immunoglobulin sequences as described by Kabat et al. (See Kabat, et al. (1991) Sequences of proteins of Immunological Interest, Fifth Edition, U.S. Department of Health and Human Services, NIH Publication No. 91-3242). The human antibodies of the invention may include amino acid residues not encoded by human germline immunoglobulin sequences (e.g., mutations introduced by random or site-specific mutagenesis in vitro or by somatic mutation in vivo), e.g., in the CDRs and in particular CDR3. The mutations can be introduced using the "selective mutagenesis approach." The human antibody can have at least one position replaced with an amino acid residue, e.g., an activity enhancing amino acid residue which is not encoded by the human germline immunoglobulin sequence. The human antibody can have up to twenty positions replaced with amino acid residues which are not part of the human germline immunoglobulin sequence. In other embodiments, up to ten, up to five, up to three or up to two positions are replaced. In one embodiment, these replacements are within the CDR regions. However, the term "human antibody", as used herein, is not intended to include antibodies in which CDR sequences derived from the germline of another mammalian species, such as a mouse, have been grafted onto human framework sequences.

As used herein a "recombinant expression vector" can be any suitable recombinant expression vector, and can be used to transform or transfect any suitable host. For example, one of ordinary skill in the art would appreciate that transformation or transfection is a process by which exogenous nucleic acid such as DNA is introduced into a cell wherein the transformation or transfection process involves contacting the cell with the exogenous nucleic acid such as the recombinant expression vector as described herein. Non-limiting examples of such expression vectors are the pUC series of vectors (Fermentas Life Sciences), the pBluescript series of vectors (Stratagene, La Jolla, Calif.), the pET series of vectors (Novagen, Madison, Wis.), the pGEX series of vectors (Pharmacia Biotech, Uppsala, Sweden), and the pEX series vectors (Clontech, Palo Alto, Calif.).

The phrase "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see, e.g., Taylor, L. D., et al. (1992) Nucl. Acids Res, 20:6287-6295, the entire teaching of which is incorporated herein by reference) or antibodies prepared, expressed, created or isolated by any other means that involves splicing of human immunoglobulin gene sequences to other DNA sequences. Such recombinant human antibodies have variable and constant regions derived from human germline immunoglobulin sequences (see, Kabat, E. A., et al. (1991) Sequences of Proteins of Immunological Interest, Fifth Edition, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. In certain embodiments, however, such recombinant antibodies are the result of selective mutagenesis approach or back-mutation or both.

An "isolated antibody" includes an antibody that is substantially free of other antibodies having different antigenic specificities (e.g., an isolated antibody that specifically binds a particular target protein is substantially free of antibodies that specifically bind antigens other than the target protein). An isolated antibody that specifically binds a human target protein may bind target molecules from other species. Moreover, an isolated antibody may be substantially free of other cellular material and/or chemicals.

As used herein, the term "adalimumab", also known by its trade name Humira® (AbbVie) refers to a human IgG antibody that binds the human form of tumor necrosis factor alpha. In general, the heavy chain constant domain 2 (CH2) of the adalimumab IgG-Fc region is glycosylated through covalent attachment of oligosaccharide at asparagine 297 (Asn-297). Weak cation-exchange chromatography (WCX) analysis of the antibody has shown that it has three main charged-variants (i.e. Lys 0, Lys 1, and Lys 2). These variants, or charged isomers, are the result of incomplete posttranslational cleavage of the C-terminal lysine residues.

The term "activity" includes activities such as the binding specificity/affinity of an antibody for an antigen and/or the neutralizing potency of an antibody.

The phrase "nucleic acid molecule" includes DNA molecules and RNA molecules. A nucleic acid molecule may be single-stranded or double-stranded, but in one aspect is double-stranded DNA.

The phrase "isolated nucleic acid molecule," as used herein in reference to nucleic acids encoding antibodies or antibody portions (e.g., VH, VL, CDR3) and includes a nucleic acid molecule in which the nucleotide sequences encoding the antibody or antibody portion are free of other nucleotide sequences encoding antibodies or antibody portions that bind antigens other than the target antigen, which other sequences may naturally flank the nucleic acid in human genomic DNA. Thus, e.g., an isolated nucleic acid of the invention encoding a VH region of a particular antibody contains no other sequences encoding other VH regions that bind antigens other than the target antigen. The phrase "isolated nucleic acid molecule" is also intended to include sequences encoding bivalent, bispecific antibodies, such as diabodies in which VH and VL regions contain no other sequences other than the sequences of the diabody.

The phrase "recombinant host cell" (or simply "host cell") includes a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "recombinant protein" refers to a protein produced as the result of the transcription and translation of a gene carried on a recombinant expression vector that has been introduced into a host cell. In certain embodiments the recombinant protein is an antibody, preferably a chimeric, humanized, or fully human antibody. In certain embodiments the recombinant protein is an antibody of an isotype selected from group consisting of: IgG (e.g., IgG1, IgG2, IgG3, IgG4), IgM, IgA1, IgA2, IgD, or IgE. In certain embodiments the antibody molecule is a full-length antibody (e.g., an IgG1 or IgG4 immunoglobulin) or alternatively the antibody can be a fragment (e.g., an Fc fragment or a Fab fragment).

As used herein, the term "cell culture" refers to methods and techniques employed to generate and maintain a population of host cells capable of producing a recombinant protein of interest, as well as the methods and techniques for optimizing the production and collection of the protein of interest. For example, once an expression vector has been incorporated into an appropriate host, the host can be maintained under conditions suitable for high level expression of the relevant nucleotide coding sequences, and the collection and purification of the desired recombinant protein. Mammalian cells are preferred for expression and production of the recombinant of the present invention, however other eukaryotic cell types can also be employed in the context of the instant invention. See, e.g., Winnacker, From Genes to Clones, VCH Publishers, N.Y., N.Y. (1987). Suitable mammalian host cells for expressing recombinant proteins according to the invention include Chinese Hamster Ovary (CHO cells) (including dhfr– CHO cells, described in Urlaub and Chasin, (1980) PNAS USA 77:4216-4220, used with a DHFR selectable marker, e.g., as described in Kaufman and Sharp (1982) Mol. Biol. 159:601-621, the entire teachings of which are incorporated herein by reference), NS0 myeloma cells, COS cells and SP2 cells. Other examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/–DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2), the entire teachings of which are incorporated herein by reference.

When using the cell culture techniques of the instant invention, the protein of interest can be produced intracellularly, in the periplasmic space, or directly secreted into the medium. In embodiments where the protein of interest is produced intracellularly, the particulate debris, either host cells or lysed cells (e.g., resulting from homogenization), can be removed by a variety of means, including but not limited to, by centrifugation or ultrafiltration. Where the protein of interest is secreted into the medium, supernatants from such expression systems can be first concentrated using a commercially available protein concentration filter, e.g., an Amicon™ or Millipore Pellicon™ ultrafiltration unit, which can then be subjected to one or more additional purification techniques, including but not limited to affinity chromatography, including protein A affinity chromatography, ion exchange chromatography, such as anion or cation exchange chromatography, and hydrophobic interaction chromatography.

As used herein the term "on-line" refers to processes that are accomplished in the context of an on-going cell culture run. For example, the administration of a particular nutrient or change in temperature, or pH occur on-line when such administrations or changes are implemented in an existing cell culture run. Similarly, measurement of certain data is considered on-line if that data is being collected in the context of a particular cell culture run. For example, on-line gas analysis refers to the measurement of gases introduced into or released from a particular cell culture run. In contrast, the term "off-line", as used herein, refers to actions taken outside the context of a particular cell culture run. For example, the production of cell culture media comprising specific concentrations of particular components is an example of an off-line activity.

The term "modifying", as used herein, is intended to refer to changing one or more amino acids in the antibodies or antigen-binding portions thereof. The change can be produced by adding, substituting or deleting an amino acid at one or more positions. The change can be produced using known techniques, such as PCR mutagenesis.

The term "about", as used herein, is intended to refer to ranges of approximately 10-20% greater than or less than the referenced value. In certain circumstances, one of skill in the art will recognize that, due to the nature of the referenced value, the term "about" can mean more or less than a 10-20% deviation from that value.

The term "control", as used herein, is intended to refer to both limitation as well as to modulation. For example, in certain embodiments, the instant invention provides methods for controlling diversity that decrease the diversity of certain characteristics of protein populations, including, but not limited to, the presence, distribution and/or amounts of lysine variants. Such decreases in diversity can occur by: (1) promotion of a desired characteristic; (2) inhibition of an unwanted characteristic; or (3) a combination of the foregoing. As used herein, the term "control" also embraces contexts where heterogeneity is modulated, i.e., shifted, from one diverse population to a second population of equal, or even greater diversity, where the second population exhibits a distinct profile of the characteristic of interest.

5.2 Antibody Generation

The term "antibody" as used in this section refers to an intact antibody or an antigen binding fragment thereof.

The antibodies of the present disclosure can be generated by a variety of techniques, including immunization of an animal with the antigen of interest followed by conventional monoclonal antibody methodologies e.g., the standard somatic cell hybridization technique of Kohler and Milstein (1975) Nature 256: 495. Although somatic cell hybridization procedures are preferred, in principle, other techniques for producing monoclonal antibody can be employed e.g., viral or oncogenic transformation of B lymphocytes.

One preferred animal system for preparing hybridomas is the murine system. Hybridoma production is a very well-established procedure. Immunization protocols and techniques for isolation of immunized splenocytes for fusion are known in the art. Fusion partners (e.g., murine myeloma cells) and fusion procedures are also known.

An antibody preferably can be a human, a chimeric, or a humanized antibody. Chimeric or humanized antibodies of the present disclosure can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al.). To create a humanized antibody, murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In one non-limiting embodiment, the antibodies of this disclosure are human monoclonal antibodies. Such human monoclonal antibodies can be generated using transgenic or transchromosomic mice carrying parts of the human immune system rather than the mouse system. These transgenic and transchromosomic mice include mice referred to herein as the HuMAb Mouse® (Medarex, Inc.), KM Mouse® (Medarex, Inc.), and XenoMouse® (Amgen).

Moreover, alternative transchromosomic animal systems expressing human immunoglobulin genes are available in the art and can be used to raise antibodies of the disclosure. For example, mice carrying both a human heavy chain transchromosome and a human light chain transchromosome, referred to as "TC mice" can be used; such mice are described in Tomizuka et al. (2000) Proc. Natl. Acad. Sci. USA 97:722-727. Furthermore, cows carrying human heavy and light chain transchromosomes have been described in the art (e.g., Kuroiwa et al. (2002) Nature Biotechnology 20:889-894 and PCT application No. WO 2002/092812) and can be used to raise antibodies of this disclosure.

Recombinant human antibodies of the invention can be isolated by screening of a recombinant combinatorial antibody library, e.g., a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia Recombinant Phage Antibody System, catalog no. 27-9400-01; and the Stratagene SurfZAP™ phage display kit, catalog no. 240612, the entire teachings of which are incorporated herein), examples of methods and reagents particularly amenable for use in generating and screening antibody display libraries can be found in, e.g., Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) Bio/Technology 9:1370-1372; Hay et al. (1992) Hum Antibody Hybridomas 3:81-85; Huse et al. (1989) Science 246:1275-1281; McCafferty et al., Nature (1990) 348:552-554; Griffiths et al. (1993) EMBO J. 12:725-734; Hawkins et al. (1992) J Mol Biol 226:889-896; Clackson et al. (1991) Nature 352:624-628; Gram et al. (1992) PNAS 89:3576-3580; Garrard et al. (1991) Bio/Technology 9:1373-1377; Hoogenboom et al. (1991) Nuc Acid Res 19:4133-

4137; and Barbas et al. (1991) PNAS 88:7978-7982; the entire teachings of which are incorporated herein.

Human monoclonal antibodies of this disclosure can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

In certain embodiments, the methods of the invention include anti-TNFα antibodies and antibody portions, anti-TNFα-related antibodies and antibody portions, and human antibodies and antibody portions with equivalent properties to anti-TNFα, such as high affinity binding to hTNFα with low dissociation kinetics and high neutralizing capacity. In one aspect, the invention provides treatment with an isolated human antibody, or an antigen-binding portion thereof, that dissociates from hTNFα with a Kd of about $1 \times 10^{-8}$ M or less and a Koff rate constant of $1 \times 10^{-3}$ $s^{-1}$ or less, both determined by surface plasmon resonance. In specific non-limiting embodiments, an anti-TNFα antibody purified according to the invention competitively inhibits binding of Adalimumab to TNFα under physiological conditions.

In yet another embodiment of the invention, antibodies or fragments thereof, can be altered wherein the constant region of the antibody is modified to reduce at least one constant region-mediated biological effector function relative to an unmodified antibody. To modify an antibody of the invention such that it exhibits reduced binding to the Fc receptor, the immunoglobulin constant region segment of the antibody can be mutated at particular regions necessary for Fc receptor (FcR) interactions (see, e.g., Canfield and Morrison (1991) J. Exp. Med. 173:1483-1491; and Lund et al. (1991) J. of Immunol. 147:2657-2662, the entire teachings of which are incorporated herein). Reduction in FcR binding ability of the antibody may also reduce other effector functions which rely on FcR interactions, such as opsonization and phagocytosis and antigen-dependent cellular cytotoxicity.

5.3 Protein Production

To express a protein of the invention, such as an antibody or antigen-binding fragment thereof, DNAs encoding the protein, such as DNAs encoding partial or full-length light and heavy chains in the case of antibodies, are inserted into one or more expression vector such that the genes are operatively linked to transcriptional and translational control sequences. (See, e.g., U.S. Pat. No. 6,914,128, the entire teaching of which is incorporated herein by reference.) In this context, the term "operatively linked" is intended to mean that a gene encoding the protein of interest is ligated into a vector such that transcriptional and translational control sequences within the vector serve their intended function of regulating the transcription and translation of the gene. The expression vector and expression control sequences are chosen to be compatible with the expression host cell used. In certain embodiments, the protein of interest will comprising multiple polypeptides, such as the heavy and light chains of an antibody. Thus, in certain embodiments, genes encoding multiple polypeptides, such as antibody light chain genes and antibody heavy chain genes, can be inserted into a separate vector or, more typically, the genes are inserted into the same expression vector. Genes are inserted into expression vectors by standard methods (e.g., ligation of complementary restriction sites on the gene fragment and vector, or blunt end ligation if no restriction sites are present). Prior to insertion of the gene or genes, the expression vector may already carry additional polypeptide sequences, such as, but no limited to, antibody constant region sequences. For example, one approach to converting the antibody or antibody-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the protein from a host cell. The gene can be cloned into the vector such that the signal peptide is linked in-frame to the amino terminus of the gene. The signal peptide can be an immunoglobulin signal peptide or a heterologous signal peptide (i.e., a signal peptide from a non-immunoglobulin protein).

In addition to protein coding genes, a recombinant expression vector of the invention can carry one or more regulatory sequence that controls the expression of the protein coding genes in a host cell. The term "regulatory sequence" is intended to include promoters, enhancers and other expression control elements (e.g., polyadenylation signals) that control the transcription or translation of the protein coding genes. Such regulatory sequences are described, e.g., in Goeddel; Gene Expression Technology: Methods in Enzymology 185, Academic Press, San Diego, Calif. (1990), the entire teaching of which is incorporated herein by reference. It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see, e.g., U.S. Pat. No. 5,168,062 by Stinski, U.S. Pat. No. 4,510,245 by Bell et al. and U.S. Pat. No. 4,968,615 by Schaffner et al., the entire teachings of which are incorporated herein by reference.

In addition to the protein coding genes and regulatory sequences, a recombinant expression vector of the invention may carry one or more additional sequences, such as a sequence that regulates replication of the vector in host cells (e.g., origins of replication) and/or a selectable marker gene. The selectable marker gene facilitates selection of host cells into which the vector has been introduced (see e.g., U.S. Pat. Nos. 4,399,216, 4,634,665 and 5,179,017, all by Axel et al., the entire teachings of which are incorporated herein by reference). For example, typically the selectable marker gene confers resistance to drugs, such as G418, hygromycin or methotrexate, on a host cell into which the vector has been introduced. Suitable selectable marker genes include the dihydrofolate reductase (DHFR) gene (for use in dhfr– host cells with methotrexate selection/amplification) and the neo gene (for G418 selection).

An antibody, or antibody portion, of the invention can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), Molecular Cloning; A Laboratory Manual, Second Edition, Cold Spring Harbor, N.Y., (1989), Ausubel et al. (eds.) Current Protocols in Molecular Biology, Greene Publishing Associates, (1989) and in U.S. Pat. Nos. 4,816,397 & 6,914,128, the entire teachings of which are incorporated herein.

For expression of protein, for example, the light and heavy chains of an antibody, the expression vector(s) encoding the protein is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the proteins of the invention in either prokaryotic or eukaryotic host cells, expression of antibodies in eukaryotic cells, such as mammalian host cells, is suitable because such eukaryotic cells, and in particular mammalian cells, are more likely than prokaryotic cells to assemble and secrete a properly folded and immunologically active protein. Prokaryotic expression of protein genes has been reported to be ineffective for production of high yields of active protein (Boss and Wood (1985) Immunology Today 6:12-13, the entire teaching of which is incorporated herein by reference).

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, e.g., Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published Apr. 12, 1989), *Pseudomonas* such as *P. aeruginosa*, and *Streptomyces*. One suitable *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for polypeptide encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183, 070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated proteins, for example, glycosylated antibodies, are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

Suitable mammalian host cells for expressing the recombinant proteins of the invention include Chinese Hamster Ovary (CHO cells) (including dhfr– CHO cells, described in Urlaub and Chasin, (1980) PNAS USA 77:4216-4220, used with a DHFR selectable marker, e.g., as described in Kaufman and Sharp (1982) Mol. Biol. 159:601-621, the entire teachings of which are incorporated herein by reference), NS0 myeloma cells, COS cells and SP2 cells. When recombinant expression vectors encoding protein genes are introduced into mammalian host cells, the antibodies are produced by culturing the host cells for a period of time sufficient to allow for expression of the antibody in the host cells or secretion of the antibody into the culture medium in which the host cells are grown. Other examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/–DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2), the entire teachings of which are incorporated herein by reference.

Host cells are transformed with the above-described expression or cloning vectors for protein production and cultured in conventional nutrient media modified as appropriate for inducing promoters, selecting transformants, or amplifying the genes encoding the desired sequences.

The host cells used to produce a protein may be cultured in a variety of media. Commercially available media such as Ham's F10™ (Sigma), Minimal Essential Medium™ (MEM), (Sigma), RPMI-1640 (Sigma), and Dulbecco's Modified Eagle's Medium™ (DMEM), (Sigma) are suitable for culturing the host cells. In addition, any of the media described in Ham et al., Meth. Enz. 58:44 (1979), Barnes et al., Anal. Biochem. 102:255 (1980), U.S. Pat. No. 4,767,704; 4,657,866; 4,927,762; 4,560,655; or 5,122,469; WO 90/03430; WO 87/00195; or U.S. Pat. No. Re. 30,985 may be used as culture media for the host cells, the entire teachings of which are incorporated herein by reference. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamycin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Host cells can also be used to produce portions of intact proteins, for example, antibodies, including Fab fragments or scFv molecules. It is understood that variations on the above procedure are within the scope of the present invention. For example, in certain embodiments it may be desirable to transfect a host cell with DNA encoding either the light chain or the heavy chain (but not both) of an antibody. Recombinant DNA technology may also be used to remove some or all of the DNA encoding either or both of the light and heavy chains that is not necessary for binding to an antigen. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the target antigen, depending on the specificity of the antibody of the invention, by crosslinking an antibody of the invention to a second antibody by standard chemical crosslinking methods.

In a suitable system for recombinant expression of a protein, for example, an antibody, or antigen-binding portion thereof, a recombinant expression vector encoding the protein, for example, both an antibody heavy chain and an antibody light chain, is introduced into dhfr-CHO cells by calcium phosphate-mediated transfection. Within the recombinant expression vector, the protein gene(s) are each operatively linked to CMV enhancer/AdMLP promoter regulatory elements to drive high levels of transcription of the gene(s). The recombinant expression vector also carries a DHFR gene, which allows for selection of CHO cells that have been transfected with the vector using methotrexate selection/amplification. The selected transformant host cells are cultured to allow for expression of the protein, for example, the antibody heavy and light chains, and intact protein, for example, an antibody, is recovered from the culture medium. Standard molecular biology techniques are used to prepare the recombinant expression vector, transfect the host cells, select for transformants, culture the host cells and recover the protein from the culture medium.

When using recombinant techniques, the protein, for example, antibodies or antigen binding fragments thereof, can be produced intracellularly, in the periplasmic space, or directly secreted into the medium. In one aspect, if the protein is produced intracellularly, as a first step, the particulate debris, either host cells or lysed cells (e.g., resulting from homogenization), can be removed, e.g., by centrifugation or ultrafiltration. Where the protein is secreted into the medium, supernatants from such expression systems can be first concentrated using a commercially available protein concentration filter, e.g., an Amicon™ or Millipore Pellicon™ ultrafiltration unit.

Prior to the process of the invention, procedures for purification of protein, for example, antibodies or antigen binding fragments thereof, from cell debris initially depend on the site of expression of the protein. Some proteins can be secreted directly from the cell into the surrounding growth media; others are made intracellularly. For the latter proteins, the first step of a purification process typically involves: lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. Where the protein is secreted, supernatants from such expression systems are generally first concentrated using a commercially available protein concentration filter, e.g., an Amicon™ or Millipore Pellicon™ ultrafiltration unit. Where the protein is secreted into the medium, the recombinant host cells can also be separated from the cell culture medium, e.g., by tangential flow filtration protein can be further recovered from the culture medium using the protein purification methods of the invention.

Numerous populations of proteins expressed by host cells, including, but not limited to, host cells expressing antibodies, such as adalimumab, may comprise a number of lysine variants, for example, combinations of two or more of Lys 0, Lys 1 and Lys 2, and are therefore amenable to the instant invention's methods for control of C-terminal lysine variant heterogeneity. For example, weak cation-exchange chromatography (WCX) analysis of adalimumab has shown the presence of the three lysine variants corresponding to Lys 0, Lys 1 and Lys 2. The presence of these lysine variants provides an exemplary system to identify those cell culture conditions that allow for control over lysine variant heterogeneity.

The production of C-terminal lysine variants can be dependent upon changes in process parameters. (Lawrence, D. (2008), C-terminal Lysine Variants in Fully Human Monoclonal Antibodies: Investigation of Test Methods and Possible Causes. Biotechnology and Bioengineering. 100: 1132-1143). Native glycoproteins and/or recombinant glycoproteins (e.g., natural antibodies and/or therapeutic antibodies) that are translated at the endoplasmic reticulum (ER) must fold properly and often assemble into multimeric complexes. There are several proteins that help these proteins to fold properly. Some of these proteins only need the cleavage of the ER N-terminal sequence of the protein to become a mature protein. However, other glycoproteins can require further processing ("posttranslational modifications") to become a mature and fully-functional. Some of these post-translational modifications include glycosylation, formation of disulfide bonds, N-terminal pyroglutamate, methionine oxidation, asparagine deamination, phosphorylation, acetylation, and enzymatic removal of C-terminal lysine or arginine residues. (Ahrer et al., (2006), Chromatographic and Electrophoretic Characterization of Protein Variants. Journal of Chromatography. 841:110-122; Li et al. (2005), Current Therapeutic Antibody Production and Process Optimization. Bioprocessing Journal; Harris, J. (1995), Processing of C-terminal Lysine and Arginine Residues of Proteins Isolated from Mammalian Cell Culture. Journal of Chromatography. 705: 129-134; and Parkins, M., Theiler, R., et al. (2000), Determination of the Origin of Charge Heterogeneity in a Murine Monoclonal Antibody. Pharmaceutical Research. 17: 1110-1117).

Without being bound by theory, studies have demonstrated that the enzymatic removal of the C-terminal Lys residues is the primary contributor to the heterogeneity of recombinant monoclonal antibodies, including, but not limited to, the adalimumab glycoprotein. (Harris et al. (2004), Commercial Manufacturing Scale Formulation and Analytical Characterization of Therapeutic Recombinant Antibodies. Drug Development Research. 61: 137-154). Additional studies have determined that the charge heterogeneity can be generated by: 1) removal of the lysine or arginine C-terminal residue in the IgG heavy chains; 2) conversion of N-terminal glutamate to pyroglutamate; 3) dehydration of aspartate residues; and 4)

alternate cleavage of a signal peptide that results in the presence of basic residues. The adalimumab heavy chain terminal sequence is proline-glycine-lysine. However, as noted above, the lysine residues are partially removed during the manufacturing process. Thus, adalimumab can comprise a mixture of antibodies bearing zero, one, or two C-terminal lysine residues. The specific sequence can be detected by cation exchange chromatography. It has been observed that this charge heterogeneity, caused by the incomplete posttranslational cleavage, may not affect the potency of the protein to bind the TNF-α. (Santora et al., (2001), Characterization of Noncovalent Complexes of Recombinant Human Monoclonal Antibody and Antigen Using Cation Exchange, Size Exclusion Chromatography, and BIAcore. Analytical Biochemistry 299: 119-129). Even though the removal of C-terminal lysine residues may not couple with the biological function of the antibody, it is a factor to consider in maintaining batch-to-batch consistency. (Parkins et al. (2000), Determination of the Origin of Charge Heterogeneity in a Murine Monoclonal Antibody. Pharmaceutical Research. 17: 1110-1117).

Experiments have shown that the charge heterogeneity of the antibody, due to the incomplete removal of C-terminal lysine residues, can be traced to carboxypeptidase activity/expression differences due to process parameter variability or changes. Since the penultimate residue, glycine, is not removed, this suggests that the carboxypeptidase is specific for basic residues, such as lysine and arginine. (Lawrence, D. (2008), C-terminal Lysine Variants in Fully Human Monoclonal Antibodies: Investigation of Test Methods and Possible Causes. Biotechnology and Bioengineering. 100: 1132-1143: and Harris, J. (1995), Processing of C-terminal Lysine and Arginine Residues of Proteins Isolated from Mammalian Cell Culture. Journal of Chromatography. 705: 129-134). In order to develop strategies to control such charged isomer heterogeneity, as well as heterogeneity in glycosylation, the experiments outlined in the Examples below were conducted.

The experiments disclosed herein demonstrate that, in certain embodiments, variation in raw materials used in cell culture, and particularly in the context of media preparation, can vary product quality significantly. For example, as outlined herein, control over the amount of Zinc present in cell culture media can allow for the modulation of C-terminal lysine variant heterogeneity. Zinc has been previously reported in literature to be a cofactor of the enzyme carboxypeptidase (Valee B et. al (1960), The role of zinc in carboxypeptidase, Journal of Biological Chemistry, 235, 1, 64-69). However, it was not appreciated until the filing of the instant application that adjusting the levels of zinc in culture media could allows for modulation of the lysine variants.

5.3.1 Adjusting Zinc Concentration to Control Lysine Variation

In certain embodiments of the instant invention, control of C-terminal lysine variant heterogeneity can be attained by adjustment of the zinc concentration of the media employed in the cell culture run. In certain non-limiting embodiments, such adjustment will be to decrease the amount of Zinc in the media, while in other non-limiting embodiments the necessary adjustment to achieve the desired control over lysine variant heterogeneity will involve an increase in the amount of Zinc in the media. Such increases or decreases in the amount of Zinc can be of a magnitude of 1%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding, of the original amount.

In certain embodiments, cell culture media containing no Zinc is supplemented with Zinc to achieve a final Zinc concentration in the cell culture media of less than 60 μM. In certain embodiments, the cell culture will contain a total concentration of Zinc of between about 0.025 and about 10 μM, between about 0.05 and 10 μM, between about 0.1 and 10 μM, between about 0.2 and 10 μM, between about 0.25 and 10 μM, between about 0.5 and 10 μM, between about 1 and 10 μM, between about 1.5 and 9.5 μM, between about 2 and 9 μM, between about 2.5 and 8.5 μM, between about 3 and 8 μM, between about 3.5 and 7.5 μM, between about 4 and 7 μM, between about 4.5 and 6.5 μM, between about 5 and 6 μM. In certain embodiments, the cell culture media containing no Zinc is supplemented with Zinc to achieve a final Zinc concentration in the cell culture media of about 3.4 μM or about 6.7 μM.

In certain embodiments, the cell culture media contains Zinc in an amount effective to reduce the amount of one or more C-terminal lysine variants in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding.

In certain embodiments, the cell culture media contains Zinc in an amount effective to increase the amount of one or more C-terminal lysine variants in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%. 25%, 30%, 35%, 40%, 45%, 50%, 55%, 60%, 65%, 70%, 75%, 80%, 85%, 90%, 95%, 100%, and ranges within one or more of the preceding.

In certain embodiments, the cell culture media contains Zinc in an amount effective to reduce the amount of a Lys 0 lysine variant, and to increase the amount of a Lys 1 and/or Lys 2 lysine variant expressed by the cell culture.

For example, and not by way of limitation, as detailed in Example 6.1, below, certain embodiments include, but are not limited to when the Zinc concentration of the cell culture medium employed is reduced from a control concentration of about 10 μM to about 3.4 μM, and the % Lys 0 of an adalimumab sample purified from the supplemented culture is reduced to 67.9% from a control amount of 92.7%. Additionally, the amounts of Lys 1 and Lys 2 in the adalimumab sample are increased to 19.9% (Lys 1) and 12.2% (Lys 2) from an adalimumab sample purified from the control culture (10 μM Zinc) having 6.3% Lys 1 and 1.0% Lys 2. Furthermore, as detailed in Example 6.1, below, certain embodiments include, but are not limited to when the Zinc concentration of the cell culture medium employed is reduced from a control concentration of about 10 μM to about 3.4 μM or about 6.7 μM, and the % Lys 0 of an adalimumab sample purified from the supplemented culture is reduced to 69.0% (3.4 μM) or 89.9% (6.7 μM) from a control amount of 92.8%. Additionally, the amounts of Lys 1 and Lys 2 in the adalimumab sample are increased to 21.8% (Lys 1-3.4 μM), 8.7% (Lys 1-6.7 μM), 9.1% (Lys 2-3.4 μM), and 1.4% (Lys 2-6.7 μM) from an adalimumab sample purified from the control culture (10 μM Zinc) having 6.2% Lys 1 and 1.1% Lys 2.

In certain embodiments, the cell culture contains Zinc as well as arginine, lysine, and histidine, each at a concentration sufficient to reduce the amount of a Lys 0 lysine variant, and to increase the amount of a Lys 1 and/or Lys 2 lysine variant expressed by the cell culture. For example, but not by way of limitation, the concentration range for arginine and lysine in this can be between about 1 to about 3 g/l, while the concentration range for histidine is between about 0 to about 1 g/l and the concentration range for zinc is about 30 µM to about 60 µM.

5.3.2 Adjusting Amino Acid Concentration to Control C-Terminal Lysine Variation In certain embodiments of the instant invention, control of C-terminal lysine variant heterogeneity can be attained by adjustment of the amino acid composition of the cell culture media. In certain embodiments, such adjustment will be to increase the amount of one or more amino acids in the media, while in other embodiments the necessary adjustment to achieve the desired control over lysine variant heterogeneity will involve a decrease in the amount of one or more amino acids in the media. Such increases or decreases in the amount of the one or more amino acids can be of a magnitude of 1%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding, of the original amount.

In certain embodiments, the cell culture media is supplemented with one or more amino acids wherein each of the one or more amino acids is supplemented in an amount of between about 0.025 and 20 g/L, or between about 0.05 and 15 g/L, or between about 0.1 and 14 g/L, or between about 0.2 and 13 g/L, or between about 0.25 and 12 g/L, or between about 0.5 and 11 g/L, or between about 1 and 10 g/L, or between about 1.5 and 9.5 g/L, or between about 2 and 9 g/L, or between about 2.5 and 8.5 g/L, or between about 3 and 8 g/L, or between about 3.5 and 7.5 g/L, or between about 4 and 7 g/L, or between about 4.5 and 6.5 g/L, or between about 5 and 6 g/L. In certain embodiments, the cell culture media is supplemented with one or more amino acids wherein each of the one or more amino acids is supplemented in an amount of about 0.5 g/L, or about 1 g/L, or about 2 g/L, or about 4 g/L, or about 8 g/L.

In certain embodiments, the cell culture media is supplemented with one or more amino acids wherein each of the one or more amino acids is supplemented in an amount effective to reduce the amount of one or more lysine variants in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding.

In certain embodiments, the cell culture media is supplemented with one or more amino acids wherein each of the one or more amino acids is supplemented in an amount effective to increase the amount of one or more C-terminal lysine variants in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding.

In certain embodiments, the cell culture media is supplemented with one or more amino acids wherein each of the one or more amino acids is supplemented in an amount effective to reduce the amount of a Lys 0 lysine variant, and to increase the amount of a Lys 1 and/or Lys 2 lysine variant expressed by the cell culture.

In certain embodiments, the one or more amino acids used to supplement the cell culture media is arginine, lysine, histidine, or certain combinations of arginine or lysine with ornithine. In certain embodiments, the amino acids are provided as single peptides, as dipeptides, as tripeptides or as longer oligopeptides. In certain embodiments, the di-, tri-, and/or oligopeptides are individually composed of a single amino acid, while in alternative embodiments, the di-, tri-, and/or oligopeptides are individually composed of two or more particular amino acids.

For example, and not by way of limitation, as detailed in Example 6.2, below, when the production medium employed in the example was supplemented with 3 g/L arginine and 3 g/L lysine, the % Lys 0 of an adalimumab sample purified from the supplemented culture was reduced to 72.1% from a control amount of 86.7%. Additionally, the amounts of Lys 1 and Lys 2 in the adalimumab sample was increased to 20.8% (Lys 1) and 7.1% (Lys 2) from an adalimumab sample purified from a control culture having 11.1% Lys 1 and 2.2% Lys 2.

Similarly, although the percentage of Lys0 relative to Lysine sum in the control sample was 82.9% on day 10, in the sample with the highest concentration of arginine in this experiment (9 g/l), the percentage of relative Lys0 was reduced to 73.4%. This relative modulation of Lys 0, Lys 1 and Lys 2 was directly related to the concentration of arginine in the media. Thus, in certain embodiments, the relative level of Lys0 to lysine sum can be modulated, i.e., increased or decreased, by adjusting the concentration of arginine in the culture media.

In certain embodiments, a lysine supplementation of cell culture is employed to modulate the ratio of Lys0 to lysine sum. As detailed Example 6.2, below, in the sample with the highest concentration of lysine (11 g/l), the percentage of relative levels of Lys0 was reduced to 67.7%, which contrasts with the percentage of Lys0 relative to lysine sum (sum of the peak areas corresponding to Lys 0, Lys 1 and Lys 2) in the control sample of 92.5%. A dose dependent decrease in relative Lys0, and a dose dependent increase in relative Lys1 and Lys2 regions was observed in test conditions with increased lysine concentration. Thus, in certain embodiments, the relative level of Lys0 to lysine sum can be modulated, i.e., increased or decreased, by adjusting the concentration of lysine in the culture media.

In certain embodiments, a histidine supplementation of cell culture is employed to modulate the ratio of Lys0 to lysine sum. As detailed Example 6.2, below, in the sample with the highest concentration of histidine (10 g/l), the percentage of relative Lys0 was reduced to 80.6% from a control sample percentage of 92.5%. The decrease in Lys 0 corresponded with the increase in relative levels of both Lys1 and Lys2. In an alternative example, the percentage of Lys0 relative to lysine sum in the control sample was 94.2%. In the sample with the highest concentration of histidine in this experiment (8 g/l), the percentage of relative Lys0 was reduced to 81.5%. The decrease in Lys0 corresponded with the increase in relative levels of both Lys1 and Lys2. A dose dependent decrease in relative Lys0, and a dose dependent increase in relative Lys1 and Lys2 regions was observed in test conditions with increased histidine concentration. Thus, in certain embodiments, the relative level of Lys0 to lysine sum can be modulated, i.e., increased or decreased, by adjusting the concentration of histidine in the culture media.

In certain embodiments, an ornithine/arginine or ornithine/lysine supplementation of cell culture is employed to modulate the ratio of Lys0 to lysine sum. As detailed Example 6.2, below, the combination of ornithine with arginine or lysine reduced the relative level of Lys0 to 81.9% in comparison with the condition with just arginine and lysine increase with a relative level Lys0 of 84.7%. Thus, the increase of ornithine may exhibit synergistic effects in modulating lysine variant distribution when added in combination with arginine and lysine. Thus, in certain embodiments, the relative level of Lys0 to lysine sum can be modulated, i.e., increased or decreased, by adjusting the concentration of a combination of ornithine and either arginine and/or lysine in the culture media.

In certain embodiments, an arginine/lysine/histidine/ornithine combination supplementation of cell culture is employed to modulate the ratio of Lys0 to lysine sum. As detailed in Example 6.2, below, in comparison to the lower concentrations, or conditions where amino acids were supplemented individually, a further reduction in Lys0 relative to lysine sum was observed in conditions where combinations of amino acids were increased in the media. A progressive decrease was observed in relative Lys0 when more amino acids were increased in combination. The percentage of relative Lys0 was reduced from 94.9% in the control sample to 73.9% in the sample with all four amino acid concentrations increased. Thus, in certain embodiments, the relative level of Lys0 to lysine sum can be modulated, i.e., increased or decreased, by adjusting the concentration of a combination of all four amino acids (arginine, lysine, histidine, and ornithine) in the culture media.

In certain embodiments, the three amino acid monomers arginine, lysine, and histidine, the dipeptides lys-lys and arg-lys, or the tripeptides lys-lys-lys, his-arg-lys, and arg-his-lys are used as supplements to cell culture in order to modulate the ratio of Lys0 to lysine sum. As detailed in Example 6.2, below, in comparison to the control, a reduction in Lys0 relative to lysine sum was also observed in conditions where dipeptides and tripeptides were supplemented to the media. Specifically, a decrease was observed in relative Lys0 when polypeptides were supplemented. The percentage of relative Lys0 was reduced from 88.0% in the control sample to 71.9% in a sample supplemented with tripeptide arg-his-lys (4 g/l), and to 74.0% in a sample supplemented with his-arg-lys (2 g/l).

In certain embodiments, the medium supplements described herein are such that they can be included in the medium at the start of culture, or can be added in a fed-batch or in a continuous manner. The medium supplements could be supplemented to chemically defined or hydrolysate based basal media. The methods described in this invention may be used in combination with different cultivation methods including, but not limited to, batch, fed-batch, chemostat and perfusion, and with various cell culture equipment including, but not limited to, shake flasks with or without suitable agitation, spinner flasks, stirred bioreactors, airlift bioreactors, membrane bioreactors, reactors with cells retained on a solid support or immobilized/entrapped as in microporous beads, and any other configuration appropriate for optimal growth and productivity of the desired cell line. The methods described here may also be combined with the appropriate choice of process parameters as described in section 5.3.3.

5.3.3 Adjusting Process Parameters to Control Lysine Variation

The variation in the process parameters, such as the temperature and/or pH, at which cells are cultured, can vary product quality significantly. In certain embodiments of the instant invention, control of C-terminal lysine variant heterogeneity can be attained by adjustment of the temperature and/or pH of the cell culture run. In certain embodiments, such adjustment will be to increase the temperature and/or pH at which a cell culture is cultured, while in other embodiments the necessary adjustment to achieve the desired control over lysine variant heterogeneity will involve a modulation of the temperature and/or pH at which a cell culture is cultured.

Such increases or decreases in cell culture temperature, and/or pH can be of a magnitude of 1%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding, of the original temperature.

In certain embodiments, the cell culture is cultured at a temperature of between about 25 and 50° C., or between about 30 and 40° C., or between about 31 and 39° C., or between about 31.5 and 38.5° C., or between about 32 and 38° C., or between about 32.5 and 37.5° C., or between about 33 and 37° C., or between about 33.5 and 36.5° C., or between about 34 and 36° C., or between about 34.5 and 35.5° C. In certain embodiments, the cell culture is cultured at a temperature of about 30, 31, 32, 33, 34, 35, 36, or 37° C.

For example, and not by way of limitation, as detailed in Example 6.3, below, when the temperature of a cell culture run was decreased from 37° C. to 31° C., the % Lys 0 of an adalimumab sample purified from the culture was reduced from 84.9% to 72.8%. Additionally, the amounts of Lys 1 and Lys 2 in the adalimumab sample was increased from 13.4% (Lys 1) and 1.7% (Lys 2), to 22.2% (Lys 1) and 5.0% (Lys 2). Thus, in certain embodiments, the relative level of Lys0 to lysine sum can be modulated, i.e., increased or decreased, by adjusting the temperature of the cell culture run.

In certain embodiments, pH is either increased or decreased in order to increase or decrease the amount of Lys0 relative to the lysine sum. For example, but not by way of limitation, a reduction in pH to 6.7 from a control pH of 7.1 can be employed to increase the amount of Lys0 relative to the lysine sum. For example, and not by way of limitation, as detailed in Example 6.3, below, when the pH of a cell culture run was decreased from 7.1 to 6.7, the % Lys 0 of an adalimumab sample purified from the culture was increased from 82.0% to 88.7%. In certain embodiments the pH is increased from 6.7 to 6.8, 6.9, 7.0, or 7.1 in order to achieve a decrease in the amount of Lys0 relative to the lysine sum.

In certain embodiments, the temperature and/or pH of the cell culture is decreased or increased in an amount effective to reduce the amount of one or more lysine variants in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding.

In certain embodiments, the temperature and/or pH of the cell culture is decreased or increased in an amount effective to increase the amount of one or more lysine variants in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding.

In certain embodiments, the temperature and/or pH of the cell culture is decreased or increased in an amount effective to reduce the amount of a Lys 0 lysine variant, and to increase the amount of a Lys 1 and/or Lys 2 lysine variant expressed by the cell culture.

5.3.4 Additional Exemplary Strategies

In addition to the above-described embodiments, the present invention is also directed to embodiments wherein the medium supplements described herein are added in a batch-wise fashion, a continuous feeding fashion, or a combination of both during cell culture. In addition, certain embodiments will involve the adding such media supplements one at a time and/or addition at multiple time points during the cell culture process. In certain embodiments, the cell culture process will involve preloading the culture media with excess of one or more medium supplements. In certain embodiments, the addition of one or more supplements will be based on measurements taken on-line, in-line, and/or at line. In certain embodiments, the addition of one or more supplements will occur with other substrates, metal scavengers, and/or combination with other culture conditions such as temperature pH, etc. In certain embodiments, one or more media supplements will be added as multimers, e.g., arg-arg, his-his, arg-his-orn, etc., and/or as chemical variants of amino acids or analogs of amino acids, salt forms of amino acids, controlled release of amino acids by immobilizing in gels, etc, and/or in fully or partially dissolved form.

In certain embodiments, the culture process will occur in bags, flasks, disposables, hollow fiber, perfusion, and/or air lift process equipment. In certain embodiments, one or more media supplements will be added to seed bioreactor before transfer to achieve a final concentration in the fermentor. In certain embodiments, achieving a known concentration of one or more of the media supplements can occur either through an in-situ combination resulting the generation of the supplement or a degradation/reaction resulting the generation of the supplement, i.e., adding a substrate and enzyme/catalyst to produce the components necessary. In certain embodiments the addition of one or more media supplement will based on measured amount of lysine distribution.

5.4 Protein Purification

5.4.1 Protein Purification Generally

In certain embodiments, the methods of the present invention can be used in combination with techniques for protein purification to provide for the production of a purified protein preparation, for example, a preparation comprising an antibody or an antigen binding fragment thereof, from a mixture comprising a protein and at least one process-related impurity or product-related substance.

For example, but not by way of limitation, once a clarified solution or mixture comprising the protein of interest, for example, an antibody or antigen binding fragment thereof, has been obtained, separation of the protein of interest from the process-related impurities and/or product-related substances can be performed using a combination of different purification techniques, including, but not limited to, affinity separation steps, ion exchange separation steps, mixed mode separation steps, and hydrophobic interaction separation steps. The separation steps separate mixtures of proteins on the basis of their charge, degree of hydrophobicity, or size. In one aspect of the invention, separation is performed using chromatography, including cationic, anionic, and hydrophobic interaction. Several different chromatography resins are available for each of these techniques, allowing accurate tailoring of the purification scheme to the particular protein involved. The essence of each of the separation methods is that proteins can be caused either to traverse at different rates down a column, achieving a physical separation that increases as they pass further down the column, or to adhere selectively to the separation medium, being then differentially eluted by different solvents. In some cases, the antibody is separated from impurities when the impurities specifically adhere to the column and the antibody does not, i.e., the antibody is present in the flow through.

As noted above, accurate tailoring of a purification scheme relies on consideration of the protein to be purified. In certain embodiments, the separation steps of employed in connection with the cell culture methods of the instant invention facilitate the separation of an antibody from one or more process-related impurity and/or product-related substance. Antibodies that can be successfully purified using the methods described herein include, but are not limited to, human IgA1, IgA2, IgD, IgE, IgG1, IgG2, IgG3, IgG4, and IgM antibodies. In certain embodiments, Protein A affinity chromatography can be useful, however, in certain embodiments, the use of Protein A affinity chromatography would prove useful, for example in the context of the purification of IgG3 antibodies, as IgG3 antibodies bind to Protein A inefficiently. Other factors that allow for specific tailoring of a purification scheme include, but are not limited to: the presence or absence of an Fc region (e.g., in the context of full length antibody as compared to an Fab fragment thereof) because Protein A binds to the Fc region; the particular germline sequences employed in generating to antibody of interest; and the amino acid composition of the antibody (e.g., the primary sequence of the antibody as well as the overall charge/hydrophobicity of the molecule). Antibodies sharing one or more characteristic can be purified using purification strategies tailored to take advantage of that characteristic.

5.4.2 Primary Recovery and Virus Inactivation

In certain embodiments, it will be advantageous to subject a sample produced by the techniques of the instant invention to at least a first phase of clarification and primary recovery. In addition, the primary recovery process can also be a point at which to reduce or inactivate viruses that can be present in the sample mixture. For example, any one or more of a variety of methods of viral reduction/inactivation can be used during the primary recovery phase of purification including heat inactivation (pasteurization), pH inactivation, solvent/detergent treatment, UV and γ-ray irradiation and the addition of certain chemical inactivating agents such as β-propiolactone or e.g., copper phenanthroline as in U.S. Pat. No. 4,534,972, the entire teaching of which is incorporated herein by reference.

The primary recovery may also include one or more centrifugation steps to further clarify the sample mixture and thereby aid in purifying the protein of interest. Centrifugation of the sample can be run at, for example, but not by way of limitation, 7,000×g to approximately 12,750×g. In the context of large scale purification, such centrifugation can occur on-line with a flow rate set to achieve, for example, but not by way of limitation, a turbidity level of 150 NTU in the resulting supernatant. Such supernatant can then be collected for further purification.

In certain embodiments, the primary recovery may also include the use of one or more depth filtration steps to further clarify the sample matrix and thereby aid in purifying the antibodies produced using the cell culture techniques of the present invention. Depth filters contain filtration media having a graded density. Such graded density allows larger particles to be trapped near the surface of the filter while smaller particles penetrate the larger open areas at the surface of the filter, only to be trapped in the smaller openings nearer to the center of the filter. In certain embodiments, the depth filtration step can be a delipid depth filtration step. Although certain embodiments employ depth filtration steps only during the primary recovery phase, other embodiments employ depth filters, including delipid depth filters, during one or more additional phases of purification. Non-limiting examples of depth filters that can be used in the context of the

5.4.3 Affinity Chromatography

In certain embodiments, it will be advantageous to subject a sample produced by the techniques of the instant invention to affinity chromatography to further purify the protein of interest away from process-related impurities and/or product-related substances. In certain embodiments the chromatographic material is capable of selectively or specifically binding to the protein of interest. Non-limiting examples of such chromatographic material include: Protein A, Protein G, chromatographic material comprising, for example, an antigen bound by an antibody of interest, and chromatographic material comprising an Fc binding protein. In specific embodiments, the affinity chromatography step involves subjecting the primary recovery sample to a column comprising a suitable Protein A resin. In certain embodiments, Protein A resin is useful for affinity purification and isolation of a variety of antibody isotypes, particularly IgG1, IgG2, and IgG4. Protein A is a bacterial cell wall protein that binds to mammalian IgGs primarily through their Fc regions. In its native state, Protein A has five IgG binding domains as well as other domains of unknown function.

There are several commercial sources for Protein A resin. One suitable resin is MabSelect™ from GE Healthcare. A non-limiting example of a suitable column packed with Mab-Select™ is an about 1.0 cm diameter×about 21.6 cm long column (~17 mL bed volume). This size column can be used for small scale purifications and can be compared with other columns used for scale ups. For example, a 20 cm×21 cm column whose bed volume is about 6.6 L can be used for larger purifications. Regardless of the column, the column can be packed using a suitable resin such as MabSelect™.

5.4.4 Ion Exchange Chromatography

In certain embodiments, it will be advantageous to subject a sample produced by the techniques of the instant invention to ion exchange chromatography in order to purify the protein of interest away from process-related impurities and/or product-related substances. Ion exchange separation includes any method by which two substances are separated based on the difference in their respective ionic charges, and can employ either cationic exchange material or anionic exchange material. For example, the use of a cationic exchange material versus an anionic exchange material is based on the localized charges of the protein. Therefore, it is within the scope of this invention to employ an anionic exchange step prior to the use of a cationic exchange step, or a cationic exchange step prior to the use of an anionic exchange step. Furthermore, it is within the scope of this invention to employ only a cationic exchange step, only an anionic exchange step, or any serial combination of the two.

In performing the separation, the initial protein mixture can be contacted with the ion exchange material by using any of a variety of techniques, e.g., using a batch purification technique or a chromatographic technique.

Anionic or cationic substituents may be attached to matrices in order to form anionic or cationic supports for chromatography. Non-limiting examples of anionic exchange substituents include diethylaminoethyl (DEAE), quaternary aminoethyl (QAE) and quaternary amine (Q) groups. Cationic substituents include carboxymethyl (CM), sulfoethyl (SE), sulfopropyl (SP), phosphate (P) and sulfonate (S). Cellulose ion exchange resins such as DE23™, DE32™, DE52™, CM-23™, CM-32™, and CM-52™ are available from Whatman Ltd. Maidstone, Kent, U.K. SEPHADEX®-based and -locross-linked ion exchangers are also known. For example, DEAE-, QAE-, CM-, and SP-SEPHADEX® and DEAE-, Q-, CM- and S-SEPHAROSE® and SEPHAROSE® Fast Flow are all available from Pharmacia AB. Further, both DEAE and CM derivitized ethylene glycol-methacrylate copolymer such as TOYOPEARL™ DEAE-650S or M and TOYOPEARL™ CM-650S or M are available from Toso Haas Co., Philadelphia, Pa.

5.4.5 Ultrafiltration/Diafiltration

In certain embodiments, it will be advantageous to subject a sample produced by the techniques of the instant invention to ultrafiltration and/or diafiltration in order to purify the protein of interest away from process-related impurities and/or product-related substances. Ultrafiltration is described in detail in: Microfiltration and Ultrafiltration: Principles and Applications, L. Zeman and A. Zydney (Marcel Dekker, Inc., New York, N.Y., 1996); and in: Ultrafiltration Handbook, Munir Cheryan (Technomic Publishing, 1986; ISBN No. 87762-456-9). A preferred filtration process is Tangential Flow Filtration as described in the Millipore catalogue entitled "Pharmaceutical Process Filtration Catalogue" pp. 177-202 (Bedford, Mass., 1995/96). Ultrafiltration is generally considered to mean filtration using filters with a pore size of smaller than 0.1 µM. By employing filters having such small pore size, the volume of the sample can be reduced through permeation of the sample buffer through the filter while antibodies are retained behind the filter.

Diafiltration is a method of using ultrafilters to remove and exchange salts, sugars, and non-aqueous solvents, to separate free from bound species, to remove low molecular-weight material, and/or to cause the rapid change of ionic and/or pH environments. Microsolutes are removed most efficiently by adding solvent to the solution being ultrafiltered at a rate approximately equal to the ultratfiltration rate. This washes microspecies from the solution at a constant volume, effectively purifying the retained protein. In certain embodiments of the present invention, a diafiltration step is employed to exchange the various buffers used in connection with the instant invention, optionally prior to further chromatography or other purification steps, as well as to remove impurities from the protein preparations.

5.4.6 Hydrophobic Interaction Chromatography

In certain embodiments, it will be advantageous to subject a sample produced by the techniques of the instant invention to hydrophobic interaction chromatography in order to purify the protein of interest away from process-related impurities and/or product-related substances. For example, a first eluate obtained from an ion exchange column can be subjected to a hydrophobic interaction material such that a second eluate having a reduced level of impurity is obtained. Hydrophobic interaction chromatography (HIC) steps, such as those disclosed herein, are generally performed to remove protein aggregates, such as antibody aggregates, and process-related impurities.

In performing an HIC-based separation, the sample mixture is contacted with the HIC material, e.g., using a batch purification technique or using a column. Prior to HIC purification it may be desirable to remove any chaotropic agents or very hydrophobic substances, e.g., by passing the mixture through a pre-column.

Whereas ion exchange chromatography relies on the charges of the protein to isolate them, hydrophobic interaction chromatography uses the hydrophobic properties of the protein. Hydrophobic groups on the protein interact with hydrophobic groups on the column. The more hydrophobic a protein is the stronger it will interact with the column. Thus the HIC step removes host cell derived impurities (e.g., DNA and other high and low molecular weight product-related species).

Hydrophobic interactions are strongest at high ionic strength, therefore, this form of separation is conveniently performed following salt precipitations or ion exchange procedures. Adsorption of the protein of interest to a HIC column is favored by high salt concentrations, but the actual concentrations can vary over a wide range depending on the nature of the protein and the particular HIC ligand chosen. Various ions can be arranged in a so-called soluphobic series depending on whether they promote hydrophobic interactions (salting-out effects) or disrupt the structure of water (chaotropic effect) and lead to the weakening of the hydrophobic interaction, Cations are ranked in terms of increasing salting out effect as $Ba^{++}$; $Ca^{++}$; $Mg^{++}$; $Li^{++}$; $Cs^+$; $Na^+$; $K^+$; $Rb^+$; $NH4^+$ while anions may be ranked in terms of increasing chaotropic effect as $PO^{---}$; $SO_4^{---}$; $CH_3CO_3^-$; $Cl^-$; $Br^-$; $NO_3^-$; $ClO_4^-$; $I^-$; $SCN^-$.

In general, Na, K or $NH_4$ sulfates effectively promote ligand-protein interaction in HIC. Salts may be formulated that influence the strength of the interaction as given by the following relationship: $(NH_4)_2SO_4>Na_2SO_4>NaCl>NH_4Cl>NaBr>NaSCN$. In general, salt concentrations of between about 0.75 and about 2 M ammonium sulfate or between about 1 and 4 M NaCl are useful.

HIC columns normally comprise a base matrix (e.g., cross-linked agarose or synthetic copolymer material) to which hydrophobic ligands (e.g., alkyl or aryl groups) are coupled. A suitable HIC column comprises an agarose resin substituted with phenyl groups (e.g., a Phenyl Sepharose™ column). Many HIC columns are available commercially. Examples include, but are not limited to, Phenyl Sepharose™ 6 Fast Flow column with low or high substitution (Pharmacia LKB Biotechnology, AB, Sweden); Phenyl Sepharose™ High Performance column (Pharmacia LKB Biotechnology, AB, Sweden); Octyl Sepharose™ High Performance column (Pharmacia LKB Biotechnology, AB, Sweden); Fractogel™ EMD Propyl or Fractogel™ EMD Phenyl columns (E. Merck, Germany); Macro-Prep™ Methyl or Macro-Prep™ t-Butyl Supports (Bio-Rad, California); WP HI-Propyl (C3)™ column (J. T. Baker, New Jersey); and Toyopearl™ ether, phenyl or butyl columns (TosoHaas, Pa.).

5.4.7 Multimodal Chromatography

In certain embodiments, it will be advantageous to subject a sample produced by the techniques of the instant invention to multimodal chromatography in order to purify the protein of interest away from process-related impurities and/or product-related substances. Multimodal chromatography is chromatography that utilizes a multimodal media resin. Such a resin comprises a multimodal chromatography ligand. In certain embodiments, such a ligand refers to a ligand that is capable of providing at least two different, but co-operative, sites which interact with the substance to be bound. One of these sites gives an attractive type of charge-charge interaction between the ligand and the substance of interest. The other site typically gives electron acceptor-donor interaction and/or hydrophobic and/or hydrophilic interactions. Electron donor-acceptor interactions include interactions such as hydrogen-bonding, π-π, cation-π, charge transfer, dipole-dipole, induced dipole etc. Multimodal chromatography ligands are also known as "mixed mode" chromatography ligands.

In certain embodiments, the multimodal chromatography resin is comprised of multimodal ligands coupled to an organic or inorganic support, sometimes denoted a base matrix, directly or via a spacer. The support may be in the form of particles, such as essentially spherical particles, a monolith, filter, membrane, surface, capillaries, etc. In certain embodiments, the support is prepared from a native polymer, such as cross-linked carbohydrate material, such as agarose, agar, cellulose, dextran, chitosan, konjac, carrageenan, gellan, alginate etc. To obtain high adsorption capacities, the support can be porous, and ligands are then coupled to the external surfaces as well as to the pore surfaces. Such native polymer supports can be prepared according to standard methods, such as inverse suspension gelation (S Hjerten: Biochim Biophys Acta 79(2), 393-398 (1964). Alternatively, the support can be prepared from a synthetic polymer, such as cross-linked synthetic polymers, e.g. styrene or styrene derivatives, divinylbenzene, acrylamides, acrylate esters, methacrylate esters, vinyl esters, vinyl amides etc. Such synthetic polymers can be produced according to standard methods, see e.g. "Styrene based polymer supports developed by suspension polymerization" (R Arshady: Chimica e L'Industria 70(9), 70-75 (1988)). Porous native or synthetic polymer supports are also available from commercial sources, such as Amersham Biosciences, Uppsala, Sweden.

5.5 Pharmaceutical Compositions

The proteins, for example, antibodies and antibody-portions, produced using the cell culture techniques of the instant invention can be incorporated into pharmaceutical compositions suitable for administration to a subject. Typically, the pharmaceutical composition comprises a protein of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it is desirable to include isotonic agents, e.g., sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

The protein compositions of the invention can be incorporated into a pharmaceutical composition suitable for parenteral administration. The protein can be prepared as an injectable solution containing, e.g., 0.1-250 mg/mL antibody. The injectable solution can be composed of either a liquid or lyophilized dosage form in a flint or amber vial, ampule or pre-filled syringe. The buffer can be L-histidine approximately 1-50 mM, (optimally 5-10 mM), at pH 5.0 to 7.0 (optimally pH 6.0). Other suitable buffers include but are not limited to sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 24%). Stabilizers can be used in both liquid and lyophilized dosage forms, principally 1-50 mM L-methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants.

In one aspect, the pharmaceutical composition includes the protein at a dosage of about 0.01 mg/kg-10 mg/kg. In another aspect, the dosages of the protein include approximately 1 mg/kg administered every other week, or approximately 0.3 mg/kg administered weekly. A skilled practitioner can ascertain the proper dosage and regime for administering to a subject.

The compositions of this invention may be in a variety of forms. These include, e.g., liquid, semi-solid and solid dosage forms, such as liquid solutions (e.g., injectable and infusible solutions), dispersions or suspensions, tablets, pills, powders, liposomes and suppositories. The form depends on, e.g., the intended mode of administration and therapeutic application. Typical compositions are in the form of injectable or infusible solutions, such as compositions similar to those used for passive immunization of humans with other antibodies. One mode of administration is parenteral (e.g., intravenous, subcutaneous, intraperitoneal, intramuscular). In one aspect, the protein is administered by intravenous infusion or injection. In another aspect, the protein is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., protein, antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the methods of preparation are vacuum drying and spray-drying that yields a powder of the active ingredient plus any additional desired ingredient from a previously sterile-filtered solution thereof. The proper fluidity of a solution can be maintained, e.g., by the use of a coating such as lecithin, by the maintenance of the required particle size in the case of dispersion and by the use of surfactants. Prolonged absorption of injectable compositions can be brought about by including in the composition an agent that delays absorption, e.g., monostearate salts and gelatin.

The protein of the present invention can be administered by a variety of methods known in the art, one route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978, the entire teaching of which is incorporated herein by reference.

In certain aspects, a protein of the invention may be orally administered, e.g., with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain aspects, a protein of the invention is co-formulated with and/or co-administered with one or more additional therapeutic agents that are useful for treating disorders. For example, an antibody or antibody portion of the invention may be co-formulated and/or co-administered with one or more additional antibodies that bind other targets (e.g., antibodies that bind other cytokines or that bind cell surface molecules). Furthermore, one or more antibodies of the invention may be used in combination with two or more of the foregoing therapeutic agents. Such combination therapies may advantageously utilize lower dosages of the administered therapeutic agents, thus avoiding possible toxicities or complications associated with the various monotherapies. It will be appreciated by the skilled practitioner that when the protein of the invention are used as part of a combination therapy, a lower dosage of protein may be desirable than when the protein alone is administered to a subject (e.g., a synergistic therapeutic effect may be achieved through the use of combination therapy which, in turn, permits use of a lower dose of the protein to achieve the desired therapeutic effect).

It should be understood that the protein of the invention can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the protein of the present invention. The additional agent also can be an agent which imparts a beneficial attribute to the therapeutic composition, e.g., an agent which effects the viscosity of the composition.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. In certain embodiments it is especially advantageous to formulate parenteral compositions in dosage unit form for ease of administration and uniformity of dosage. Dosage unit form as used herein refers to physically discrete units suited as unitary dosages for the mammalian subjects to be treated; each unit comprising a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of a protein of the invention is 0.01-20 mg/kg, or 1-10 mg/kg, or 0.3-1 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

6. EXAMPLES

6.1 Methods for Modulating the Lysine Variant Distribution in Cell Culture by the Modulation of Zinc Concentration in Culture Medium This example provides methods to modulate the lysine variant distribution of monoclonal antibodies by modulating the levels of zinc in medium. The examples included here cover experiments with two different adalimumab producing cell lines in chemically defined media.

6.1.1 Materials and Methods

Cell Lines and Adaptation Cultures

Two adalimumab producing cell lines were employed in the studies discussed herein. Upon thaw, cells were typically cultured in a combination of 250 mL and 500 mL Corning vented non-baffled shake flasks on a shaker platform at 110 RPM for cell line 1 and 180 rpm for cell line 2 in a 35° C., 5% $CO_2$ incubator. Subsequent to the initial cell growth in the standard IVGN CD basal growth media, cells were adapted for two passages in separate flasks in basal media containing different concentrations of zinc. Only the cultures that demonstrated good cell growth in the adaptation phase were carried forward to the production stage.

Cell Culture Media

The initial growth media was prepared from proprietary basal CD media GIA1 (Invitrogen, media 1). For the adaptation and production culture stages (in different concentrations of zinc), media was prepared starting from either proprietary basal CD media GIA1 (media 1) or CD media without zinc (Basal 2). The control cultures were carried through adaptation and production stage in Basal 1 media. The test conditions were carried through both adaptation and production stages in Basal 2 media supplemented with different concentrations of zinc. The trace element compounds supplemented to media are listed in Table 1. The detailed descriptions of culture media for the different conditions for both cell lines are listed in Table 2. All media was filtered through Corning 1 L filter systems (0.22 μm PES) and stored at 4° C. until usage.

TABLE 1

| List of trace element compounds supplemented to culture media | |
|---|---|
| Compound | Catalog No./Source |
| Zinc Chloride | Fluka, 96468 |
| Zinc Sulfate Heptahydrate | Sigma, Z0251 |

TABLE 2

| Detailed description of culture media for different experimental conditions | | |
|---|---|---|
| Cell line | Condition | Estimated final concentration of Zinc (μM) |
| 1 | 1 | 10 |
|   | 2 | 3.4 |
| 2 | 1 | 10 |
|   | 2 | 6.7 |
|   | 3 | 3.4 |

Production Cultures

Production cultures were initiated in duplicates in 500 mL Corning vented non-baffled shake flasks (200 mL working volume). The shake flasks were kept in incubators maintained at 35° C. and 5% $CO_2$ on shaker platforms that were either set at 110 rpm for cell line 1 or 180 rpm for cell line 2. In all experiments, the cells were transferred from the adaptation stage to the production stage at a split ratio of 1:5.

The harvest procedure of the shake flasks and reactors involved centrifugation of the culture sample at 3,000 RPM for 30 min and storage of supernatant in PETG bottles at −80° C. before submission for protein A purification and WCX-10 analysis.

WCX-10 Assay

For quantification of charge variants of antibodies, cation exchange chromatography was performed on a Dionex ProPac WCX-10, Analytical column 4 mm×250 mm (Dionex, Calif.), A Shimadzu LC10A HPLC system was used as the HPLC. The mobile phases used were 10 mM Sodium Phosphate dibasic pH 7.5 (Mobile phase A) and 10 mM Sodium Phosphate dibasic, 500 mM Sodium Chloride pH 5.5 (Mobile phase B). A binary gradient (94% A, 6% B: 0-20 min; 84% A, 16% B: 20-22 min; 0% A, 100% B: 22-28 min; 94% A, 6% B: 28-34 min) was used with detection at 280 nm. Quantitation is based on the relative area percent of detected peaks (FIG. 1).

6.1.2 Results and Discussion

Effect of Varying Zinc Concentration in Chemically Defined Media with Cell Line 1

In this example, the effect of varying total zinc concentration (control (10 μM), 6.7 μM, 3.4 μM) in cell culture media on culture performance and product quality was evaluated using cell line 1. The ratios of the concentration of the two zinc salts (zinc chloride, zinc sulfate) were kept constant between the test conditions. As described in the materials and methods, each of the production stage cultures were initiated from respective adaptation cultures with corresponding levels of total zinc.

A difference in cell growth and viability profiles was observed between the test conditions and the control (FIG. 2, FIG. 3). While the peak viable cell density (VCD) in the control condition was about $11 \times 10^6$ cells/ml, the peak VCD for the 3.4 μM zinc condition was about $8 \times 10^6$ cells/ml. Corresponding to difference in peak VCD, the harvest titer was also slightly reduced in the 3.4 μM zinc condition (1.0 g/l) compared to the control (1.3 g/l) (FIG. 4). The cultures were harvested on day 10 at viability of 50% or lower for each condition and the harvest was taken through protein A purification before WCX-10 analysis. From the WCX-10 analysis, the lysine variant distribution was characterized and the relative proportion of Lys0, Lys 1, and Lys2 variants were quantified as a fraction of the total Lysine sum. A zinc dose dependent decrease in the relative fraction of relative Lys0 was observed from 92.8% in the control condition to 69.0% in the 3.4 µM zinc condition. A corresponding relative increase in both Lys 1/Lys2 variants was also observed (FIG. 5).

Thus, lowering the zinc concentration provides an effective method to increase the relative proportion of the product antibody with C-terminal lysine on one or both the heavy chains (Lys1/Lys2).

Effect of Varying Zinc Concentration in Chemically Defined Media with Cell Line 2

In this example, the effect of varying total zinc concentration (control (10 µM), 3.4 µM) in basal cell culture media on cell culture performance and product quality was evaluated using cell line 2. The ratios of the concentration of the two zinc salts (zinc chloride, zinc sulfate) were kept constant between the test conditions. As described in the materials and methods, each of the production stage cultures were initiated from respective adaptation cultures with corresponding levels of total zinc.

A significant difference in cell growth and viability profile was observed between the two test conditions (FIG. 6, FIG. 7). While the peak viable cell density (VCD) in the control condition was about $22 \times 10^6$ cells/ml, the peak VCD for the 3.4 µM zinc condition was only about $11 \times 10^6$ cells/ml. Corresponding to difference in peak VCD, the harvest titer was also significantly reduced in the 3.4 µM zinc condition compared to the control (FIG. 8). The cultures were harvested on day 10 at the target viability of 50% for each condition and the harvest was taken through protein A purification before WCX-10 analysis. From the WCX-10 analysis, the lysine variant distribution was characterized and the relative proportion of Lys0, Lys1, and Lys2 variants were quantified as a fraction of the total lysine sum. There was a decrease in the relative fraction of Lys0 in the control condition (92.7%) versus the relative Lys0 in the 3.4 µM zinc condition (67.9%). The relative fractions of Lys1/Lys2 variants were also correspondingly higher (FIG. 9).

Thus, the increase in relative proportion of the product antibody with C-terminal lysine on one or both the heavy chains (Lys 1/Lys2) corresponding to reduction in levels of zinc in basal media, was also observed in this example.

6.2 Methods for Modulating the Lysine Variant Distribution in Cell Culture by the Addition of Amino Acids This example provides methods to modulate the lysine variant distribution of monoclonal antibodies by supplementing specific components to the cell culture medium. The supplemented medium components included here are several amino acids (arginine, lysine, histidine added individually and ornithine in combination with arginine, lysine and histidine).

6.2.1 Materials and Methods

Cell Source and Adaptation Cultures

Three adalimumab producing cell lines, one mAB1 producing cell line and one mAB2 producing cell line were employed in the studies covered here.

For adalimumab producing cell lines, cells were cultured in their respective growth media (chemically defined media (media 1) or a hydrolysate based media (media 2 or media 3)) in a combination of vented non-baffled shake flasks (Corning) on a shaker platform at 110 RPM (cell line 1), 180 RPM (cell line 2), 140 RPM (cell line 3) and 10 L or 20 L wave bags (GE). For experiments with cells in the hydrolysate based media (media 3), cells were thawed in media 1 and then adapted to media 3 over a few passages, Cultures were propagated in a 35° C., 5% $CO_2$ incubator for cell line 1 and 2 and in a 36° C., 5% $CO_2$ incubator for cell line 3 in order to obtain the required number of cells to be able to initiate production stage cultures.

For the mAB1 producing cell line, cells were cultured in chemically defined growth media (media 1) in a combination of vented non-baffled shake flasks (Corning) on a shaker platform at 130 RPM and 20 L wave bags (GE). Cultures were propagated in a 36° C., 5% $CO_2$ incubator to obtain the required number of cells to be able to initiate production stage cultures.

For the mAB2 producing cell line, cells were cultured in chemically defined growth media (media 1) in a combination of vented non-baffled shake flasks (Corning) on a shaker platform at 140 RPM and 20 L wave bags (GE). Cultures were propagated in a 35° C., 5% $CO_2$ incubator to obtain the required number of cells to be able to initiate production stage cultures.

Cell Culture Media

Growth and production media were prepared from either a chemically defined media formulation (media 1) or hydrolysate-based medium formulations (media 2 and media 3). For preparation of the media 1, the media (IVGN GIA-1, proprietary formulation) was supplemented with L-glutamine, sodium bicarbonate, sodium chloride, and methotrexate solution. Production media consisted of all the components in the growth medium, excluding methotrexate. For cell line 1, mAB1, and mAB2 both growth and production medium were also supplemented with insulin.

For the hydrolysate-based formulation (media 2), the growth media was composed of PFCHO (proprietary CD formulation from SAFC), Dextrose, L-Glutamine, L-Asparagine, HEPES, Poloxamer 18S, Ferric Citrate, Recombinant Human Insulin, Yeastolate (BD), Phytone Peptone (BD), Mono- and Di-basic Sodium Phosphate, Sodium Bicarbonate, Sodium Chloride and methotrexate. Production media consisted of all the components listed in the growth medium, excluding methotrexate.

For the hydrolysate-based formulation (media 3), the growth media was composed of OptiCHO (Invitrogen), L-Glutamine, Yeastolate (BD), Phytone Peptone (BD) and methotrexate. Production media consisted of all the components listed in the growth medium, excluding methotrexate.

Amino acids used for the experiments were reconstituted in Milli-Q water to make a 100 g/L stock solution, which was subsequently supplemented to both growth and production basal media. After addition of amino acids, media was brought to a pH similar to non-supplemented (control) media using 5N hydrochloric acid/5N NaOH, and it was brought to an osmolality similar to unsupplemented (control) media by adjusting the concentration of sodium chloride. All media was filtered through Corning 1 L filter systems (0.22 µm PES) and stored at 4° C. until used.

TABLE 3

List of Amino Acids Supplemented to Culture Media and the Relevant Concentration Ranges Tested

| Amino Acid | Catalog No./Source |
|---|---|
| Arginine | Sigma, A8094 |
| Lysine | Calbiochem, 4400 |

TABLE 3-continued

List of Amino Acids Supplemented to Culture Media
and the Relevant Concentration Ranges Tested

| Amino Acid | Catalog No./Source |
|---|---|
| Histidine | Sigma, H5659 |
| Ornithine | Sigma, 06503 |

Production Cultures

Production cultures were initiated either in 500 ml shake flasks (Corning) or in 3 L Bioreactors (Applikon). For shake flask experiments, duplicate 500 mL Corning vented non-baffled shake flasks (200 mL working volume) were used for each condition. The shake flasks were kept in incubators either maintained at 35° C. or 36° C. and 5% $CO_2$ on shaker platforms that were either set at 110 rpm for adalimumab producing cell line 1, 180 rpm for adalimumab producing cell line 2, 140 rpm for adalimumab producing cell line 3, 130 rpm for mAB1 producing cell line, or 140 rpm for mAB2 producing cell line. For the bioreactor experiments, 3 L bioreactors (1.5 L working volume) were run at 37-33° C. (temperature shift), 30% DO (dissolved oxygen), 200 rpm, pH profile from 7.1 to 6.9 in three days and pH 6.9 thereafter. In all experiments, the cells were transferred from the seed train to the production stage at a split ratio of 1:5.

Cultures were run in either batch or fed-batch mode. In the batch mode, cells were cultured in the respective production medium. 1.25% (v/v) of 40% glucose stock solution was fed when the media glucose concentration reduced to less than 3 g/L. In the fed-batch mode, cultures were run with either the IVGN feed as per the following feed schedule—(4% (v/v)—day 3, 6%—day 5, 8%—day 7, 10%—day 9, 10%—day 11) or 10× Ex-Cell PFCHO feed (SAFC, 67411)–3% (v/v) on day 3. In fed-batch cultures with IVGN feed, cultures were also fed with 1.25% (v/v) of 40% glucose stock solution when the glucose concentration was below 1.5 g/l on IVGN feed days and when the concentration fell below 2.5 g/l on other days. In fed-batch cultures with 10×PFCHO feed, 1.25% (v/v) of 40% glucose stock solution was fed when the media glucose concentration was below 3 g/L.

Retention samples for titer analysis, of 2×1.5 mL, were collected daily for the bioreactor experiments (section 2.2.4) beginning on Day 8, and frozen at −80° C. The samples taken from each were later submitted for titer analysis.

The harvest procedure of the shake flasks and reactors involved centrifugation of the culture sample at 3,000 RPM for 30 min and storage of supernatant in PETG bottles at −80° C. before submission for protein A purification and WCX-10 analysis.

WCX-10 Assay

The acidic species and other charge variants present in cell culture harvest samples were quantified. Cation exchange chromatography was performed on a Dionex ProPac WCX-10, Analytical column (Dionex, Calif.). A Shimadzu LC10A HPLC system was used as the HPLC.

For the adalimumab and mAB1 samples, The mobile phases used were 10 mM Sodium Phosphate dibasic pH 7.5 (Mobile phase A) and 10 mM Sodium Phosphate dibasic, 500 mM Sodium Chloride pH 5.5 (Mobile phase B). A binary gradient (94% A, 6% B: 0-20 min; 84% A, 16% B: 20-22 min; 0% A, 100% B: 22-28 min; 94% A, 6% B: 28-34 min) was used with detection at 280 nm.

For mAB2 samples, the mobile phases used were 20 mM (4-Morpholino)ethanesulfonic Acid Monohydrate (MES) pH 6.5 (Mobile phase A) and 20 mM MES, 500 mM Sodium Chloride pH 6.5 (Mobile phase B). An optimized gradient (minute/% B): 0/3, 1/3, 46/21, 47/100, 52/100, 53/3, 58/3 was used with detection at 280 nm.

Quantitation is based on the relative area percent of detected peaks. The peaks that elute at relative residence time earlier than the main peak (Lys 0) corresponding to the drug product are together represented as the acidic peaks. The peaks that eluate at a relative residence time later than main peak in the basic region correspond to Lys 1 and Lys 2 respectively.

6.2.2 Results and Discussion

Effect of Supplementation of Arginine to Culture Media

The addition of arginine was tested in several experimental systems covering multiple cell lines, media and monoclonal antibodies. Following is a detailed description of two representative experiments where two different adalimumab producing cell lines were cultured in a chemically defined media (media 1).

Cell line 2 was cultured in media 1 with different total concentrations of arginine (I (control), 1.25, 1.5, 2, 3, 5, 9 g/l). The cultures were performed in shake flasks in batch format with only glucose feed as described in the materials and methods. The cells grew to maximum viable cell densities (VCD) in the range of $18\text{-}22\times10^6$ cells/ml for the different conditions tested. The growth and viability profiles were comparable between the different conditions, although a slight decrease in viable cell density profile was observed in samples with the 9 g/l arginine condition (FIG. 10, FIG. 11). The harvest titers were comparable between the conditions (FIG. 12). On Day 10 and Day 12 of culture, duplicate shake flasks for each of the conditions were harvested and then subsequently analyzed using WCX-10 post protein A purification and the percentages of total peak(s) area corresponding to Lys 0, Lys 1 and Lys 2 were quantified (FIG. 13, FIG. 14). The percentage of Lys0 relative to lysine sum (sum of areas corresponding to peaks Lys 0, Lys 1 and Lys 2) in the control sample was as 91.9% on day 10. In the sample with the highest tested concentration of arginine in this experiment (9 g/l), the relative percentage of Lys0 was reduced to 77.2%. A dose dependent decrease in relative Lys0 was observed in conditions with arginine concentrations beyond 2 g/l (FIG. 13). The decrease in relative Lys 0 corresponded with the increase in relative levels of both Lys 1 and Lys 2. A dose dependent decrease in relative levels of Lys 0, and a corresponding dose dependent increase in Lys1 and Lys2 were observed in conditions with increased arginine. A similar trend in reduction of relative levels of Lys0 with arginine increase was also observed in the day 12 harvest samples (FIG. 14).

Cell line 3 was cultured in media 1 with different concentrations of arginine (1 (control), 3, 5, 7, 9 g/l). The cultures were performed in shake flasks in batch format with only glucose feed as described in the materials and methods. The cells grew to maximum viable cell densities (VCD) in the range of $7\text{-}10\times10^6$ cells/ml for the different conditions tested. The growth and viability profiles were comparable between the different test conditions, although a slight decrease in viable cell density and viability profiles was observed in samples with the 9 g/l arginine condition (FIG. 15, FIG. 16). The product titer was also comparable between the conditions (FIG. 17). On Day 10 of culture, duplicate shake flasks for each of the conditions were harvested and then subsequently analyzed using WCX-10 post protein A purification and the percentages of total peak(s) area corresponding to the Lys 0, Lys 1 and Lys2 species were quantified (FIG. 18). The percentage of Lys0 relative to Lysine sum in the control sample was 82.9% on day 10. In the sample with the highest concentration of arginine in this experiment (9 g/l), the percentage of relative Lys0 was reduced to 73.4%. The decrease in Lys0 corresponded with the increase in relative levels of both Lys 1 and Lys2. This relative modulation of Lys 0, Lys 1 and Lys 2 was directly related to the concentration of arginine in the media.

Thus, although the lysine variant distributions were substantially different between the control conditions in the studies presented above, significant modulation in the relative levels of the lysine variants (decrease in Lys 0 and increase in Lys 1/Lys 2) with increased arginine concentration was observed in both cases.

Additional experiments were performed with multiple cell lines in chemically defined or hydrolysate based media to demonstrate the wide range of applicability of this method. The experimental setup for each of these experiments was similar to that described above. The summaries of results of the different experiments performed for adalimumab are summarized in FIG. 19, FIG. 20 and FIG. 21. A reduction in relative Lys0, and increase in relative Lys1 and Lys2 species with increased arginine concentration was also observed in each case.

In addition to adalimumab, the utility of this method for acidic species reduction was also demonstrated for processes involving two other mABs. The experimental setup for each of these experiments was similar to that described in section above and in the materials and methods. The reduction of acidic species with arginine increase for experiments corresponding to each mAB is summarized in FIG. 22 and FIG. 23. A reduction in relative Lys0, and increase in relative Lys1 and Lys2 species with increase in arginine concentration was also observed in both cases.

Effect of Supplementation of Lysine to Culture Media

The addition of lysine was tested in several experimental systems covering multiple cell lines, media and monoclonal antibodies. Following is a detailed description of two representative experiments where two different adalimumab producing cell lines were cultured in a chemically defined media (media 1).

Cell line 2 was cultured in media 1 with different concentrations of lysine (1 (control), 5, 7, 9, 11 g/l). The cultures were performed in shake flasks in batch format with only glucose feed as described in the materials and methods. The cells grew to maximum viable cell densities (VCD) in the range of $17\text{-}23 \times 10^6$ cells/ml for the different conditions tested. A slight dose dependent decrease in viable cell density profile was observed in all test conditions, with no significant effect on viability profiles (FIG. 24 and FIG. 25). On Days 10 and 11 of culture samples were collected for titer analysis. The harvest titers for all conditions were comparable (FIG. 26). On Day 11 of culture, duplicate shake flasks for each of the conditions were harvested and then subsequently analyzed using WCX-10 post protein A purification and the percentages of total peak(s) area corresponding to the Lys 0, Lys 1 and Lys 2 peaks were quantified (FIG. 27). The percentage of Lys0 relative to lysine sum (sum of the peak areas corresponding to Lys 0, Lys 1 and Lys 2) in the control sample was 92.5%. In the sample with the highest concentration of lysine in this experiment (11 g/l), the percentage of relative levels of Lys0 was reduced to 67.7%. The decrease in Lys0 corresponded with the increase in relative levels of both Lys1 and Lys2. A dose dependent decrease in relative Lys0, and a dose dependent increase in relative Lys1 and Lys2 regions was observed in test conditions with increased lysine concentration.

Cell line 3 was cultured in media 1 with different concentrations of lysine (1 (control), 3, 5, 7, 9, 11 g/l). The cultures were performed in shake flasks in batch format with only glucose feed as described in the materials and methods. The cells grew to maximum viable cell densities (VCD) in the range of $9.5\text{-}11.5 \times 10^6$ cells/ml for the different conditions tested. The growth and viability profiles were comparable between the different conditions, although a slight decrease in viable cell density and viability profiles was observed in samples with lysine concentration greater than 1 g/l, (FIG. 28, FIG. 29). On Days 10, 11 and 12 of culture samples were collected for titer analysis. The harvest titers for all conditions were comparable (FIG. 30). On Day 12 of culture, duplicate shake flasks for each of the conditions were harvested and then subsequently analyzed using WCX-10 post protein A purification and the percentages of total peak(s) area corresponding to the Lys 0, Lys 1 and Lys2 peaks were quantified (FIG. 31). The percentage of Lys0 relative to lysine sum in the control sample was 94.2%. In the sample with the highest concentration of lysine in this experiment (11 g/l), the percentage of relative level of Lys0 was reduced to 76.0%. The decrease in Lys0 corresponded with the increase in relative levels of both Lys1 and Lys2. A dose dependent decrease in relative levels of Lys0, and a corresponding increase in relative levels of Lys1 and Lys2 was observed in test conditions with increased lysine concentration.

Additional experiments were performed with multiple cell lines in chemically defined or hydrolysate based media to demonstrate the wide range of applicability of this method. The experimental setup for each of these experiments was similar to that described above. The summaries of results of the different experiments performed for adalimumab are summarized in FIG. 32, FIG. 33 and FIG. 34. A reduction in relative levels of Lys0, and a corresponding increase in relative levels of Lys1 and Lys2 with increased lysine was also observed in each case.

In addition to adalimumab, the utility of this method for acidic species reduction was also demonstrated for processes involving two other mABs. The experimental setup for each of these experiments was similar to that described in section above and in the materials and methods. The reduction of acidic species with arginine addition for experiments corresponding to each mAB is summarized in FIG. 35 and FIG. 36. A reduction in relative levels of Lys0, and increase in relative levels of Lys1 and Lys2 species with increased lysine was also observed in each case.

Effect of Supplementation of Histidine to Culture Media

The modulation of histidine concentration was tested in several experimental systems covering multiple cell lines, media and monoclonal antibodies. Following is a detailed description of two representative experiments where two different adalimumab producing cell lines were cultured in a chemically defined media (media 1).

Cell line 2 was cultured in media 1 with different concentrations of histidine (0 (control), 4, 6, 8, 10 g/l). The cultures were performed in shake flasks in batch format with only glucose feed as described in the materials and methods. The cells grew to maximum viable cell densities (VCD) in the range of $12\text{-}22 \times 10^6$ cells/ml for the different conditions tested. A dose dependent decrease in viable cell density profile was observed in all conditions, with the 10 g/l histidine condition having significant reduction in growth (FIG. 37). A corresponding significant impact on the viability profile was also observed (FIG. 38). There was a small dose dependent decrease in titers for all conditions with histidine supplementation (FIG. 39). On Day 11 for control sample and Day 12 for the remaining conditions, duplicate shake flasks were harvested and then subsequently analyzed using WCX-10 post protein A purification and the percentages of total peak(s) area corresponding to the lysine species were quantified (FIG. 40). The percentage of Lys0 relative to lysine sum in the control sample was 92.5%. In the sample with the highest concentration of histidine in this experiment (10 g/l), the percentage of relative Lys0 was reduced to 80.6%. The decrease in Lys 0 corresponded with the increase in relative levels of both Lys1 and Lys2.

Cell line 3 was cultured in media 1 with different concentrations of histidine (0 (control), 2, 4, 6, 8 g/l). The cultures were performed in shake flasks in batch format with only glucose feed as described in the materials and methods. The cells grew to maximum viable cell densities (VCD) in the range of $6\text{-}10\times10^6$ cells/ml for the different conditions tested. A dose dependent decrease in viable cell density profile was observed in all samples supplemented with histidine (FIG. 41). In comparison to the impact on VCD profile, the viability profiles were more comparable between the conditions (FIG. 42). The harvest titers for all conditions were comparable (FIG. 43). On Day 12 of culture, duplicate shake flasks for each of the conditions were harvested and then subsequently analyzed using WCX-10 post protein A purification and the percentages of total peak(s) area corresponding to Lys 0, Lys 1 and Lys 2 species were quantified (FIG. 44). The percentage of Lys0 relative to lysine sum in the control sample was 942%. In the sample with the highest concentration of histidine in this experiment (8 g/l), the percentage of relative Lys0 was reduced to 81.5%. The decrease in Lys0 corresponded with the increase in relative levels of both Lys1 and Lys2. A dose dependent decrease in relative Lys0, and a dose dependent increase in relative Lys1 and Lys2 regions was observed in test conditions with increased histidine concentration.

Additional experiments were performed with multiple cell lines in chemically defined or hydrolysate based media to demonstrate the wide range of applicability of this method. The experimental setup for each of these experiments was similar to that described above. The results of the different experiments performed for adalimumab are summarized in FIG. 45, FIG. 46 and FIG. 47. A reduction in relative Lys0, and increase in relative Lys1 and Lys2 species with increased histidine was also observed in each case.

In addition to adalimumab, the utility of this method for acidic species reduction was evaluated for processes involving two other mABs. The experimental setup for each of these experiments was similar to that described in section above and in the materials and methods. The results for experiments corresponding to each mAB are summarized in FIG. 48 and FIG. 49. For mAB1, a dose dependent reduction in relative levels of Lys0 was evident with increased histidine. However, for mAB2, the relative change was minimal within the histidine concentration range tested.

Effect of Amino Acid Modulation on Culture Media in 3 L Bioreactors

In this study, 3 L bioreactors were set up to confirm the effect of amino acid addition on lysine variant distribution in more controlled conditions (pH and DO) at a larger scale. 8 Bioreactors (1.5 L working volume) were set up with cell line 2 in IVGN production media. The process included a temperature shift from 37° C. to 33° C. when the cell density criterion of $6\times10^6$ cells/ml was met. The pH was controlled via $CO_2$ gas flow/0.5 N Sodium Hydroxide base at a starting pH of 7.1 that was subsequently allowed to ramp down to 6.9 over the initial three days of the process. The dissolved oxygen was controlled at 30% and the agitation rate was maintained at 200 rpm. The cultures were fed with Ex-Cell PFCHO (SAFC, 67411) (3% (v/v)) on Day 3 of culture and with 18.8 g of 40% (w/v) glucose solution on days when glucose in the reactor was measured to be below 3 g/l. The test conditions included the amino acid concentration in media to be as follows: Control (1 g/l arginine and 1 g/l lysine), 3 g/l Arginine, 3 g/l Arginine/2 g/l Lysine and 3 g/l Arginine/3 g/l Lysine. Reactors were run in duplicates for each condition.

The culture performance was comparable between the different conditions with similar growth and viability profiles (FIG. 50, 51). The cultures were harvested on Day 11 with the harvest viability between 40-50% in all the different conditions. Culture harvests were processed through protein A purification and WCX-10 analysis for quantification of the lysine variants. The lysine variant distribution in the control samples were 86.7% (Lys 0), 11.1% (Lys 1) and 2.2% (Lys 2). The Lys 0 was reduced 72.1% in the condition with the highest concentration of amino acids (3 g/l Arginine/3 g/l Lysine sample) (FIG. 53). The decrease in Lys 0 corresponded with the increase in relative levels of both Lys 1 and Lys 2. Thus, increase of amino acids arginine and lysine can modulate lysine distribution even in 3 L bioreactors under controlled conditions of temperature and pH.

Effect of Ornithine Modulation on Culture Media

In this example, the effect of increased ornithine concentration was tested both individually as well as in combination with other amino acids arginine and lysine. The study was performed with adalimumab producing cell line 2 in media 1. The experiment was carried out in 500 ml shake flasks (200 ml working volume) and was run on shaker platforms set at 180 rpm in incubators set to be controlled at 35.0° C. and 5% $CO_2$. The conditions tested included a control (only 1 g/l arginine and 1 g/l lysine), and test conditions including condition 2 (1 g/l ornithine, 1 g/l arginine, 1 g/l lysine), test condition 3 (4 g/l ornithine, 1 g/l arginine and 1 g/l lysine), test conditions 4 (1 g/l ornithine, 5 g/l arginine, 1 g/l lysine), test condition 5 (0 g/l ornithine, 5 g/l arginine, 2 g/l lysine), and test condition 6 (1 g/l ornithine, 5 g/l arginine, 2 g/l lysine). The cell culture performed comparably between the control and the test conditions with similar growth and viability profiles (FIG. 54, FIG. 55). Samples were collected for all conditions on day 10 for titer, which were comparable (FIG. 56). The cultures were harvested at day 10, processed through protein A purification and WCX-10 analysis, and the relative fractions of lysine variants were estimated. There was no significant change in the lysine variant distribution in the conditions where only the ornithine concentration was increased (at 1 g/l or 4 g/l) compared to the control. However, the combination of ornithine increase with arginine or lysine increase reduced the relative level of Lys0 to 81.9% in comparison with the condition with just arginine and lysine increase with a relative level Lys0 of 84.7% (FIG. 57). Thus, the increase of ornithine may exhibit synergistic effects in modulating lysine variant distribution when added in combination with arginine and lysine.

Effect of Increase in Concentration of a Combination of Arginine, Lysine, Histidine, and Ornithine to Culture Media In this experiment, the combined use of the four amino acids arginine, lysine, histidine and ornithine for modulation of the lysine variants is demonstrated. The experiment described here was performed using adalimumab producing cell line 2 in chemically defined media (media 1). The concentration range for arginine and lysine in this experiment was 1-3 g/l while the concentration range for histidine and ornithine in this experiment was between 0-2 g/l. In comparison to the lower concentrations, or conditions where amino acids were supplemented individually, a further reduction in Lys0 relative to lysine sum was observed in conditions where combinations of amino acids were increased in the media (FIG. 58). A progressive decrease was observed in relative Lys0 when more amino acids were increased in combination. The percentage of relative Lys0 was reduced from 94.9% in the control sample to 73.9% in the sample with all four amino acids concentrations increased.

Effect of Increase in Concentration of a Combination of Arginine, Lysine, Histidine, and Zinc to Culture Media In this experiment, the combined use of zinc and the three amino acids arginine, lysine, and histidine for lysine species modulation is demonstrated. The experiment described here was performed using adalimumab producing cell line 1 in chemically defined media (media 1). The concentration range for arginine and lysine in this experiment was between 1-3 g/l. The concentration range for histidine was between 0-1 g/l. The concentration range for zinc in this experiment was 30 µM-60 µM. Using the data from the experiment, a model predicting the effects of addition of these supplements to media for relative Lys0 reduction ($R^2$: 0.98, P=0.09) is described in FIG. 59. The model predicted a contribution from each of the amino acids towards relative Lys0 reduction. The model also predicted an increase in relative Lys0 with an increase in zinc, which further supports the claim that reduction of zinc in culture causes a reduction in relative Lys0. It may be also possible to utilize this model to predict the choice of concentrations of these different components to the media, in order to achieve a target reduction in relative Lys0.

Effect of Supplementation of Single Peptides, Dipeptides and Tripeptides to Culture Media In this experiment, the use of the three amino acid monomers arginine, lysine, and histidine, use of the dipeptides lys-lys and arg-lys, and use of the tripeptides lys-lys-lys, his-arg-lys, and arg-his-lys for lysine species modulation is demonstrated. The experiment described here was performed using adalimumab producing cell line 1 in chemically defined media (media 1). The concentration range for each peptide set tested in this experiment was between 0-4 g/l. In comparison to the control, a reduction in Lys0 relative to lysine sum was also observed in conditions where dipeptides and tripeptides were supplemented to the media (FIG. 60). A decrease was observed in relative Lys0 when polypeptides were supplemented. The percentage of relative Lys0 was reduced from 88.0% in the control sample to 71.9% in a sample supplemented with tripeptide arg-his-lys (4 g/l), and to 74.0% in a sample supplemented with his-arg-lys (2 g/l).

6.2.3 Conclusion

The experiments outlined above demonstrate the different methods that can be used either by themselves or in suitable combinations to modulate the lysine variant distribution profile of a protein of interest. Specifically, increasing the concentration in culture media of the amino acids lysine, arginine, histidine, or combinations thereof along with ornithine and limiting the concentration of zinc in media, resulted in the relative modulation of the lysine variants with a decrease in the relative levels of Lys 0 and a corresponding increase in both Lys 1 and Lys 2.

6.3 Methods for Modulating the Lysine Variant Distribution in Cell Culture by Adjusting Process Parameters

6.3.1 Materials and Methods

Cell Source and Adaptation Cultures

Three adalimumab producing CHO cell lines were employed in the studies covered here. Upon thaw, adalimumab producing cell line 1 was cultured in a chemically defined basal media (media 1) or hydrolysate based growth media (media 2) in a combination of vented shake flasks on a shaker platform at 110 rpm and 20 L wavebags in a 35° C., 5% $CO_2$ incubator. In some cases, the culture might be transferred into a seed reactor with pH 7.1, 35° C. and 30% DO. In some cases, the culture was adapted to either media 1 or media 2 by propagated in a 10 L or 20 L wavebag for 7-13 days with one or two passages before initiating production stage cultures.

Upon thaw, adalimumab producing cell line 3 was cultured in chemically defined growth media (media 1) in a combination of vented shake flasks on a shaker platform at 140 rpm and 20 L wave bags. Cultures were propagated in a 36° C., and 5% $CO_2$ incubator to obtain the required number of cells to be able to initiate production stage cultures.

Cell Culture Media

Media 1, the chemical defined growth or production media, was prepared from basal IVGN CD media GIA 1. For preparation of the IVGN CD media formulation, the proprietary media was supplemented with L-glutamine, sodium bicarbonate, sodium chloride, and methotrexate solution. Production media consisted of all the components in the growth medium, excluding methotrexate. For cultures with adalimumab producing cell line 1 and mAb2 producing cell line, the medium was also supplemented with insulin. In some cases, 10 mM or 5 mM of Galactose (Sigma, G5388) and 0.2 µM or 10 µM of Manganese (Sigma, M1787) were supplemented into production medium for cultures with adalimumab producing cell line 3 and adalimumab producing cell line 1, respectively. Osmolality was adjusted by the addition of sodium chloride. All media was filtered through filter systems (0.22 µm PES) and stored at 4° C. until usage.

For the hydrolysate-based formulation (media 2), the growth media was composed of PFCHO (proprietary CD formulation from SAFC), Dextrose, L-Glutamine, L-Asparagine, HEPES, Poloxamer 188, Ferric Citrate, Recombinant Human Insulin, Yeastolate (BD), Phytone Peptone (BD), Mono- and Di-basic Sodium Phosphate, Sodium Bicarbonate, Sodium Chloride and methotrexate. Production media consisted of all the components listed in the growth medium, excluding methotrexate.

Production Cultures

Production cultures were initiated in 3 L Bioreactors (Applikon). The bioreactors (1.5-2.0 L working volume) were run at the following conditions (except for the different experimental conditions): 35° C., 30% DO (dissolved oxygen), 200 rpm, pH profile from 7.1 to 6.9 in three days and pH 6.9 thereafter. In all experiments, the cells were transferred from the wavebag to the production stage at a split ratio of 1:5.6 (except experiments with mAb2 producing cell line where the split ratio was 1:5). When the media glucose concentration reduced to less than 3 g/L, approximately 1.25% (v/v) of 40% glucose stock solution was fed The harvest procedure of reactors involved centrifugation of the culture sample at 3,000 RPM for 30 min and storage of supernatant in PETG bottles at −80° C. before submission for protein A purification and WCX-10 analysis.

WCX-10 Assay

The acidic species and other charge variants present in cell culture harvest samples were quantified. Cation exchange chromatography was performed on a Dionex ProPac WCX-10, Analytical column (Dionex, Calif.).

For adalimumab samples, the mobile phases used were 10 mM Sodium Phosphate dibasic pH 7.5 (Mobile phase A) and 10 mM Sodium Phosphate dibasic, 500 mM Sodium Chloride pH 5.5 (Mobile phase B). A binary gradient (94% A, 6% B: 0-20 min; 84% A, 16% B: 20-22 min; 0% A, 100% B: 22-28 min; 94% A, 6% B: 28-34 min) was used with detection at 280 nm. The WCX-10 method used for mAb2 samples used different buffers. The mobile phases used were 20 mM (4-Morpholino) ethanesulfonic Acid Monohydrate (MES) pH 6.5 (Mobile phase A) and 20 mM MES, 500 mM Sodium Chloride pH 6.5 (Mobile phase B). An optimized gradient (minute/% B): 0/3, 1/3, 46/21, 47/100, 52/100, 53/3, 58/3 was used with detection at 280 nm. Quantitation is based on the relative area percent of detected peaks, as described above.

6.3.2 Results and Discussion

Effect of Process pH in Media 1 with Cell Line 1

Five different pH conditions were assessed in this study: 7.1, 7.0, 6.9, 6.8 and 6.7.

The cultures were started at pH set point of 7.1; then were ramped down to the target pH set points within 4 days. All cultures reached similar maximum viable cell densities on day 8, except for the culture at pH 6.7 condition, for which the maximum cell density was much lower than the other cultures (FIG. 61). In addition, the viability of the culture at pH 7.1 and pH 7.0 dropped much earlier than the other cultures (FIG. 62). The viability of cultures at pH 7.1 and pH 7.0 were 38% and 54% on day 10, respectively; while the viability of the cultures at lower pH (including pH 6.9, 6.8 and 6.7) was above 70% on the same day. Samples were taken in the last three days of the cultures and measured for titer. The titer of each tested condition increased corresponding to the decrease in pH, from 1.2 g/l in the pH 7.1 condition to 1.8 g/l in the pH 6.8 condition; however, product titer was not continued to increase at pH 6.7 (1.6 g/l) (FIG. 63). The cultures were harvested at <50% viability. The harvest was protein A purified, then analyzed using WCX-10. From the WCX-10 analysis, the lysine variant distribution was characterized and the relative proportion of Lys0, Lys1 and Lys2 variants were quantified as a fraction of the total Lysine sum. The relative fraction of Lys0 increased with decrease in pH from 82.0% in the pH 7.1 condition to 88.7% in the pH 6.7 condition, with corresponding 5.6% decrease in relative levels of Lys 1 and 1.1% decrease in Lys2 (FIG. 64).

Effect of Process pH in Media 2 with Cell Line 1

Three different pH conditions were assessed in this study: 7.0, 6.9, and 6.8. The cultures were started at pH of 7.1; then were ramped down to the target pH set points within 3 days of culture. The viable cell density and viability were comparable across the different pH set points until day 8. After day 8, the viable cell density and viability were slightly higher corresponding to lower pH set points (FIG. 65, FIG. 66). The cultures were harvested at ~50% viability. The product titer was slightly higher at pH 6.8 comparing to pH 6.9 and 7.0 (FIG. 67). The resulting peak areas from WCX-10 analysis were quantified (FIG. 68). The relative fraction of Lys0 increased with decrease in pH from 76.8% in the pH 7.0 condition to 80.5 in the pH6.8 condition, with corresponding 2.8% decrease in relative levels of Lys1 and 0.9% decrease in Lys2.

Effect of Process pH in Media 1 with Cell Line 3

Five different pH conditions were assessed in this study: 7.1 7.0, 6.9, 6.8, and 6.7. The cultures were started at pH set point of 7.1; then were ramped down to the target pH set points within 4 days of culture. The pH set points showed significant effect on the cell growth and viability with this cell line and media. Cell density was lower at higher pH and viability also dropped earlier at higher pH (FIG. 69, FIG. 70). The cells were harvested at an approximate viability of 50%. The titer was slightly increased as the pH was reduced, reached the highest titer at pH 6.8 condition (FIG. 71). The resulting peak areas from WCX-10 analysis were quantified (FIG. 72). The relative fraction of Lys0 increased with decrease in pH from 88.1% in the pH 7.1 condition to 93.9% in the pH 6.7 condition, with corresponding 4.6% decrease in relative levels of Lys1 and 1.7% decrease in Lys2.

Effect of Process Temperature in Media 1 with Cell Line 1

Three different temperature conditions were assessed: 33° C., 35° C. and 37° C. The cultures were harvested at the target viability of 50% for each condition. At a lower temperature, the culture duration was longer with higher viability through the culture (FIG. 73, FIG. 74). Samples were collected for titer analysis on harvest days. The titer for all conditions was comparable (FIG. 75). The harvest was taken through protein A purification before WCX-10 analysis. From the WCX-10 analysis, the lysine variant distribution was characterized and the relative proportion of Lys0, Lys1 and Lys2 variants were quantified as a fraction of the total Lysine sum (FIG. 76). The relative fraction of Lys0 increased with increase in temperature from 80.3% in the 33° C. condition to 86.6% in the 37° C. condition, with corresponding 5.3% decrease in relative levels of Lys1 and 1.0% decrease in Lys2. Thus, lowering the process temperature seems to provide an effective method to increase the relative proportion of the product antibody with C-terminal lysine on one or both the heavy chains (Lys 1/Lys 2).

Effect of Process Temperature in Media 1 with Cell Line 2

Three different temperature conditions were assessed: 33° C., 35° C., and 37° C. The cultures were harvested at the target viability of 50% for each condition. The VCD and viability profiles were similar for the 37° C. and 35° C. conditions, but the 33° C. condition took longer to drop to 50% (FIG. 77, FIG. 78). The product titers were comparable at different temperature conditions (FIG. 79). The harvest was taken through protein A purification before WCX-10 analysis. From the WCX-10 analysis, the lysine variant distribution was characterized and the relative proportion of Lys0, Lys1 and Lys2 variants were quantified as a fraction of the total Lysine sum (FIG. 80) The relative fraction of Lys0 increased with increase in temperature from 88.6% in the 33° C. condition to 93.1% in the 37° C. condition, with corresponding 3.8% decrease in relative levels of Lys1 and 0.7% decrease in Lys2. Thus, the results here are consistent with that observed for cell line 1.

6.13 Conclusion

The experiments outlined above demonstrate the different methods that can be used either by themselves or in suitable combinations to control the lysine variant distribution profile of a protein of interest, e.g., the antibody adalimumab. These experiments also indicate that altering cell culture process parameters on-line can be used to modulate the lysine variant distribution. Increasing pH set points or reducing temperature set points can lead to a relative shift in lysine variant distribution from Lys0 to Lys1 Lys2.

Patents, patent applications, publications, product descriptions, GenBank Accession Numbers, and protocols that may be cited throughout this application, the disclosures of which are incorporated herein by reference in their entireties for all purposes. For example, but not by way of limitation, patent applications designated by the following U.S. Application Serial numbers are incorporated herein by reference in their entireties for all purposes: Ser. Nos. 13/803,808; 13/830,583; 13/829,989; 13/831,181; and 13/804,220.

What is claimed is:

1. A method for producing a composition comprising adalimumab, comprising culturing a cell producing adalimumab in a cell culture media comprising an amount of one or more basic amino acids sufficient to produce a composition comprising adalimumab in which less than 62% of the lysine variant species of adalimumab have zero C-terminal lysines (Lys 0).

2. The method of claim 1, wherein the one or more basic amino acids in the cell culture media is selected from the group consisting of arginine, lysine, histidine, ornithine and combinations thereof.

3. The method of claim 2, wherein the one or more basic amino acids in the cell culture media is ornithine.

4. The method of claim 2, wherein the one or more basic amino acids in the cell culture media is lysine.

5. The method of claim 4, wherein the lysine concentration in the cell culture media is 4 to 10 g/L.

6. The method of claim 2, wherein the one or more basic amino acids in the cell culture media is histidine.

7. The method of claim 1, wherein 61% or less of the lysine variant species have zero C-terminal lysines (Lys 0).

8. The method of claim 1, wherein 60% or less of the lysine variant species have zero C-terminal lysines (Lys 0).

9. The method of claim 1, wherein 58% or less of the lysine variant species have zero C-terminal lysines (Lys 0).

10. The method of claim 1, wherein 55% or less of the lysine variant species have zero C-terminal lysines (Lys 0).

11. The method of claim 1, wherein 48% or less of the lysine variant species have zero C-terminal lysines (Lys 0).

12. The method of claim 2, wherein the one or more basic amino acids in the cell culture media is arginine.

13. The method of claim 12, wherein the arginine concentration in the cell culture media is 6 to 9 g/L.

14. The method of claim 6, wherein the histidine concentration in the cell culture media is 8 g/L or more.

15. The method of claim 12, wherein the arginine concentration in the cell culture media is 6 g/L or more.

16. The method of claim 12, wherein the arginine concentration in the cell culture media is 8 g/L or more.

17. The method of claim 12, wherein the arginine concentration in the cell culture media is 9 g/L or more.

18. The method of claim 4, wherein the lysine concentration in the cell culture media is 4 g/L or more.

19. The method of claim 4, wherein the lysine concentration in the cell culture media is 8 g/L or more.

20. The method of claim 4, wherein the lysine concentration in the cell culture media is 10 g/L or more.

21. A method for producing a composition comprising adalimumab, comprising culturing a cell producing adalimumab in a cell culture media comprising an amount of lysine sufficient to produce a composition comprising adalimumab in which less than 62% of the lysine variant species of adalimumab have zero C-terminal lysines (Lys 0).

22. The method of claim 21, wherein the lysine concentration in the cell culture media is 4 to 10 g/L.

23. The method of claim 21, wherein the lysine concentration in the cell culture media is 4 g/L or more.

24. The method of claim 21, wherein the lysine concentration in the cell culture media is 8 g/L or more.

25. The method of claim 21, wherein the lysine concentration in the cell culture media is 10 g/L or more.

26. The method of claim 21, wherein 61% or less of the lysine variant species have zero C-terminal lysines (Lys 0).

27. The method of claim 21, wherein 55% or less of the lysine variant species have zero C-terminal lysines (Lys 0).

28. The method of claim 21, wherein 48% or less of the lysine variant species have zero C-terminal lysines (Lys 0).

29. A method for producing a composition comprising adalimumab, comprising culturing a cell producing adalimumab in a cell culture media comprising an amount of one or more basic amino acids sufficient to produce a composition comprising adalimumab wherein the sum of lysine variant species of adalimumab having one C-terminal lysine (Lys 1) and lysine variant species of adalimumab having two C-terminal lysines (Lys 2) is greater than 35%.

30. The method of claim 29, wherein the one or more basic amino acids in the cell culture media is selected from the group consisting of arginine, lysine, histidine, ornithine and combinations thereof.

* * * * *